United States Patent
Mendel et al.

(10) Patent No.: US 12,109,264 B2
(45) Date of Patent: Oct. 8, 2024

(54) MOTILE SPERM DOMAIN CONTAINING PROTEIN 2 AND INFLAMMATION

(71) Applicant: ImmuneWalk Therapeutics, Inc., Pearl River, NY (US)

(72) Inventors: Itzhak Mendel, Rehovot (IL); Oshrat Propheta-Meiran, Petah Tikva (IL); Yaniv Salem, Kyriat Ono (IL); Anat Shoham, Hod Hasharon (IL); Eyal Breitbart, Hashmonaim (IL)

(73) Assignee: ImmuneWalk Therapeutics, Inc., Pearl River, NY (US)

(*) Notice: Subject to any disclaimer, the term of this patent is extended or adjusted under 35 U.S.C. 154(b) by 362 days.

(21) Appl. No.: 17/019,893

(22) Filed: Sep. 14, 2020

(65) Prior Publication Data

US 2021/0077622 A1    Mar. 18, 2021

Related U.S. Application Data

(63) Continuation of application No. 15/747,918, filed as application No. PCT/IB2016/054582 on Jul. 29, 2016, now abandoned.

(60) Provisional application No. 62/199,609, filed on Jul. 31, 2015.

(51) Int. Cl.
| | | |
|---|---|---|
| *C12N 15/11* | (2006.01) | |
| *A61K 31/7105* | (2006.01) | |
| *A61K 39/00* | (2006.01) | |
| *A61K 39/395* | (2006.01) | |
| *A61P 29/00* | (2006.01) | |
| *A61P 37/06* | (2006.01) | |
| *C07K 16/28* | (2006.01) | |
| *A61K 48/00* | (2006.01) | |
| *C12N 15/113* | (2010.01) | |

(52) U.S. Cl.
CPC ...... *A61K 39/3955* (2013.01); *A61K 31/7105* (2013.01); *A61K 39/0008* (2013.01); *A61K 39/001102* (2018.08); *A61P 29/00* (2018.01); *A61P 37/06* (2018.01); *C07K 16/28* (2013.01); *A61K 2039/505* (2013.01); *A61K 48/0016* (2013.01); *C12N 15/113* (2013.01); *C12N 2310/531* (2013.01); *Y02A 50/30* (2018.01)

(58) Field of Classification Search
CPC .................. C12N 15/113; C12N 2310/531
See application file for complete search history.

(56) References Cited

U.S. PATENT DOCUMENTS

| | | |
|---|---|---|
| 11,697,682 B2 | 7/2023 | Mendel et al. |
| 11,945,875 B2 | 4/2024 | Mendel et al. |
| 2004/0171009 A1 | 9/2004 | Tang et al. |
| 2011/0015865 A1 | 1/2011 | Rosenberg et al. |
| 2011/0257034 A1 | 10/2011 | Barany et al. |
| 2012/0020954 A1 | 1/2012 | Achiron et al. |
| 2014/0128277 A1 | 5/2014 | Moller et al. |
| 2021/0095044 A1 | 4/2021 | Mendel et al. |
| 2022/0127342 A1 | 4/2022 | Mendel et al. |

FOREIGN PATENT DOCUMENTS

| | | |
|---|---|---|
| JP | A-S63-096123 | 4/1988 |
| JP | A-H10-237093 | 9/1998 |
| WO | WO-01/87981 A2 | 11/2001 |
| WO | WO-03015494 A1 | 2/2003 |
| WO | WO-03053407 A1 | 7/2003 |
| WO | WO-2010052718 A1 | 5/2010 |
| WO | WO-2012121679 A1 | 9/2012 |
| WO | WO-2013088245 A1 | 6/2013 |
| WO | WO-2016/185016 A1 | 11/2016 |
| WO | WO-2017021857 A1 | 2/2017 |

OTHER PUBLICATIONS

Freshney, Culture of Animal Cells, A Manual of Basic Technique, Alan R. Liss, Inc., 1983, New York, pp. 1-4 (Year: 1983).*
Dermer, Another anniversary for the war on cancer, Bio/Technology, 1994, 12: 320 (Year: 1994).*
Zips et al, New anticancer agents: In vitro and in vivo evaluation, In vivo, 2005, 19:1-8 (Year: 2005).*
Kipp et al, Experimental in vivo and in vitro models of multiple sclerosis: EAE and beyond, Multiple Sclerosis and Related Disorders, 2012, 1: 15-28 (Year: 2012).*
Bar-Or et al, Analyses of all matrix metalloproteinase members in leukocytes emphasize monocytes as major inﬂammatory mediators in multiple sclerosis, Brain, 2003, 126: 2738-2749 (Year: 2003).*
Shi et al, Monocyte recruitment during infection and inflammation, Nature Reviews Immunology, 2011, 11: 762-774 (Year: 2011).*
Beurger, K. "Functional Analysis of the MOSPD Gene Family," Thesis Presented for the Degree of Doctor of Philosophy, University of Edinburgh, 2010.
Han, S.M., et al. "Sperm and Oocyte Communication Mechanisms Controlling *C. elegans* Fertility," *Dev. Dynamics* 239:1265-1281, 2010, Wiley-Liss, Inc.
Ru, Y., et al., "Transient receptor potential-canonical 3 modulates sperm motility and capacitation-associated protein tyrosine phosphorylation via [Ca2+]i mobilization," *Acta Biochim. Biophys. Sin.* (Shanghai) 47(6):404-413, 2015, Oxford Press.

(Continued)

*Primary Examiner* — Ekaterina Poliakova-Georgantas

(74) *Attorney, Agent, or Firm* — Sterne, Kessler, Goldstein & Fox P.L.L.C.

(57) ABSTRACT

Disclosed herein are methods of treating, preventing, or reducing the incidence of an inflammatory disease or disorder and methods of inhibiting, preventing, or reducing the incidence of one or more activities in a cell with an inhibitor of a Motile Sperm Domain containing Protein 2 (MOSPD2). Also disclosed are inhibitors of MOSPD2 and pharmaceutical compositions containing MOSPD2 inhibitors.

20 Claims, 23 Drawing Sheets

Specification includes a Sequence Listing.

(56) References Cited

OTHER PUBLICATIONS

International Search Report and Written Opinion of the International Searching Authority for Int'l Appl. No. PCT/IB16/54582, Filed: Jul. 29, 2016, Date of Mailing: Feb. 17, 2017.
Freshney, R.I., "Culture of Animal Cells: A Manual of Basic Technique," Alan R. Liss, Inc., 1983, New York, United States, pp. 3-4.
Dermer, G.B., "Another Anniversary for the War on Cancer," *Bio/Technology*, 12:320 (1994), Wiley Online Library, New Jersey, United States.
Zips, D., et al., "New Anticancer Agents: In Vitro and In Vivo Evaluation," *In Vivo*, 19:1-8 (2005), International Institute of Anticancer Research, Kapandriti, Greece.
Editorial: "Dishing out cancer treatment," *Nature Biotechnology*, 31:85 (2013), Nature Research, Berlin, Germany.
Al-Khamis, F.A., "The use of immune modulating drugs for the treatment of multiple sclerosis," *Neurosciences*, 21(1):4-9 (2016), Elsevier Publisher, Edinburgh, United Kingdom.
Stancovski, I., et al., "Mechanistic aspects of the opposing effects of monoclonal antibodies to the ERBB2 receptor on tumor growth," *Proc. Natl. Acad. Sci. USA*, 88:8691-8695 (1991), United States National Academy of Science, District of Columbia, United States.
Jiang, B., et al., "A Novel Peptide Isolated from a Phage Display Peptide Library with Trastuzumab Can Mimic Antigen Epitope HER-2," *J. Biol. Chem.*, 280:4656-4662 (2005), American Society for Biochemistry and Molecular Biology, Maryland, United States.
Bonatti, F., et al., "Genetic susceptibility to ANCA-associated vasculitis: state of the art," *Frontiers in Immunology*, 5:1-14 (2014), International Union of Immunological Societies, Berlin, Germany.
Mendel, I., et al., "Identification of Motile Sperm Domain-Containing Protein 2 as Regulator of Human Monocyte Migration," *J. Immunol.*, 198:2125-2132 (2017), American Association of Immunologists, Rockville, Maryland, United States.
English language translation of Document FP7, JP-A-S63-096123.
English language translation of Document FP8, JP-A-H10-237093.
Unpublished co-pending U.S. Appl. No. 17/068,959, Filed: Oct. 13, 2020, Inventors: Mendel et al.
Unpublished co-pending U.S. Appl. No. 16/980,659, Int'l Filing Date: Mar. 13, 2019, Inventors: Mendel et al.
Thaler, R., et al., "Mospd1, a New Player in Mesenchymal Versus Epidermal Cell Differentiation," *J. Cell. Physiol.* 226:2505-2515, 2011, Wiley-Liss, Inc., United States.
Khotskava, Y.B., et al., "S6K1 promotes invasiveness of breast cancer cells in a model of metastasis of triple-negative breast cancer," Am. J. Transl. Res. 6(4):361-376, e-Century Publishing Corporation, United States (2014).
Stephenson, S.A., et al., "Anti-tumour effects of antibodies targeting the extracellular cysteine-rich region of the receptor tyrosine kinase EphB4," Oncotarget 6(10):7554-7569, Impact Journals, United States (2015).
Salem, Y., et al., "Newly characterized motile sperm domain-containing protein 2 promotes human breast cancer metastasis," Intl. J. Cancer 144:125-135, Wiley, United States (2019).
Kurreck, J., "RNA Interference: From Basic Research to Therapeutic Applications," Angnew. Chem. Int. Ed. 48(8):1378-1398, Wiley, United States (2009).
Plagens, A., et al., "DNA and RNA interference mechanisms by CRISPR-Cas surveillance complexes," FEMS Microbiol. Rev. 39(3):442-463, Oxford Academic Press, United Kingdom (2015).
Kole, R., et al., "RNA therapeutics: beyond RNA interference and antisense oligonucleotides," Nature Rev. Drug Discov. 11(2):125-140, Nature Publishing Group, United States (2012).
Gavrilov, K., et al., "Therapeutic siRNA: principles, challenges, and strategies," Yale J. Biol. Med. 85:187-200, Yale University, United States (2012).
Co-pending U.S. Appl. No. 18/552,952, inventors Mendel et al., U.S. National Phase of Int'l Appl. No. PCT/IB2022/052854; Int'l Filing Date: Mar. 28, 2022 (Not yet Published).
Co-pending U.S. Appl. No. 18/432,355, inventors: Mendel et al., filed Feb. 5, 2024 (Not yet Published).
Co-pending U.S. Appl. No. 18/591,208, inventors: Mendel et al., filed Feb. 29, 2024 (Not yet Published).
Co-pending U.S. Appl. No. 18/672,252, inventors: Mendel et al., filed May 23, 2024 (Not yet Published).
Bajetto, A., et al., "Chemokines and Their Receptors in the Central Nervous System," *Front. Neuroendocrin.* 22(3):147-184, Elsevier Publishing, Amsterdam, Netherlands (Jul. 2001).
Meiron, M., et al., "CXCL12 (SDF-1α) suppresses ongoing experimental autoimmune encephalomyelitis by selecting antigen-specific regulatory T cells," *J. Exp. Med.* 205(11):147-184, The Rockefeller University Press, New York City, New York (Jul. 2021).
Zohar, Y., et al., "CXCL11-dependent induction of FOXP3-negative regulatory T cells suppresses autoimmune encephalomyelitis," *J. Clin. Invest.* 124(5):2009-2022, American Society for Clinical Investigation, Ann Arbor, Michigan (Apr. 2014).
"KD value: a quantitative measurement of antibody affinity: A guide to $K_D$ value and antibody affinity," Abcam Limited website, Cambridge, United Kingdom, https://www.abcam.com/primary-antibodies/kd-value-a-quantitive-measurement-of-antibody-affinity#:~ :text-High%2Daffinity%20antibodies%20are%20generally (accessed on May 28, 2024).
Chames, P., et al., "Bispecific antibodies for cancer therapy: The light at the end of the tunnel?" *mAbs* 1(6):539-547, Taylor and Francis Group, Abingdon, United Kingdom (Nov. 2009).

\* cited by examiner

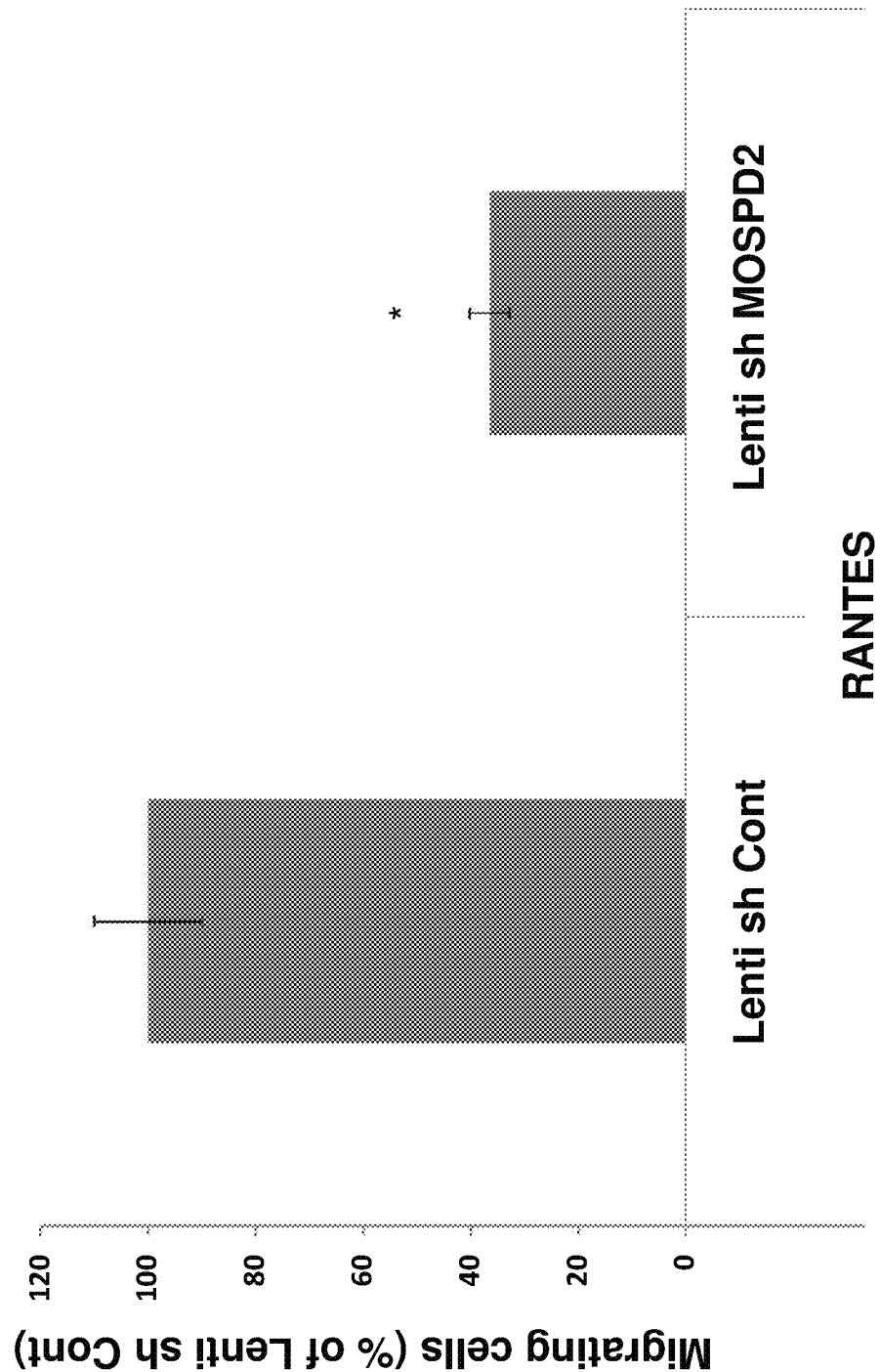

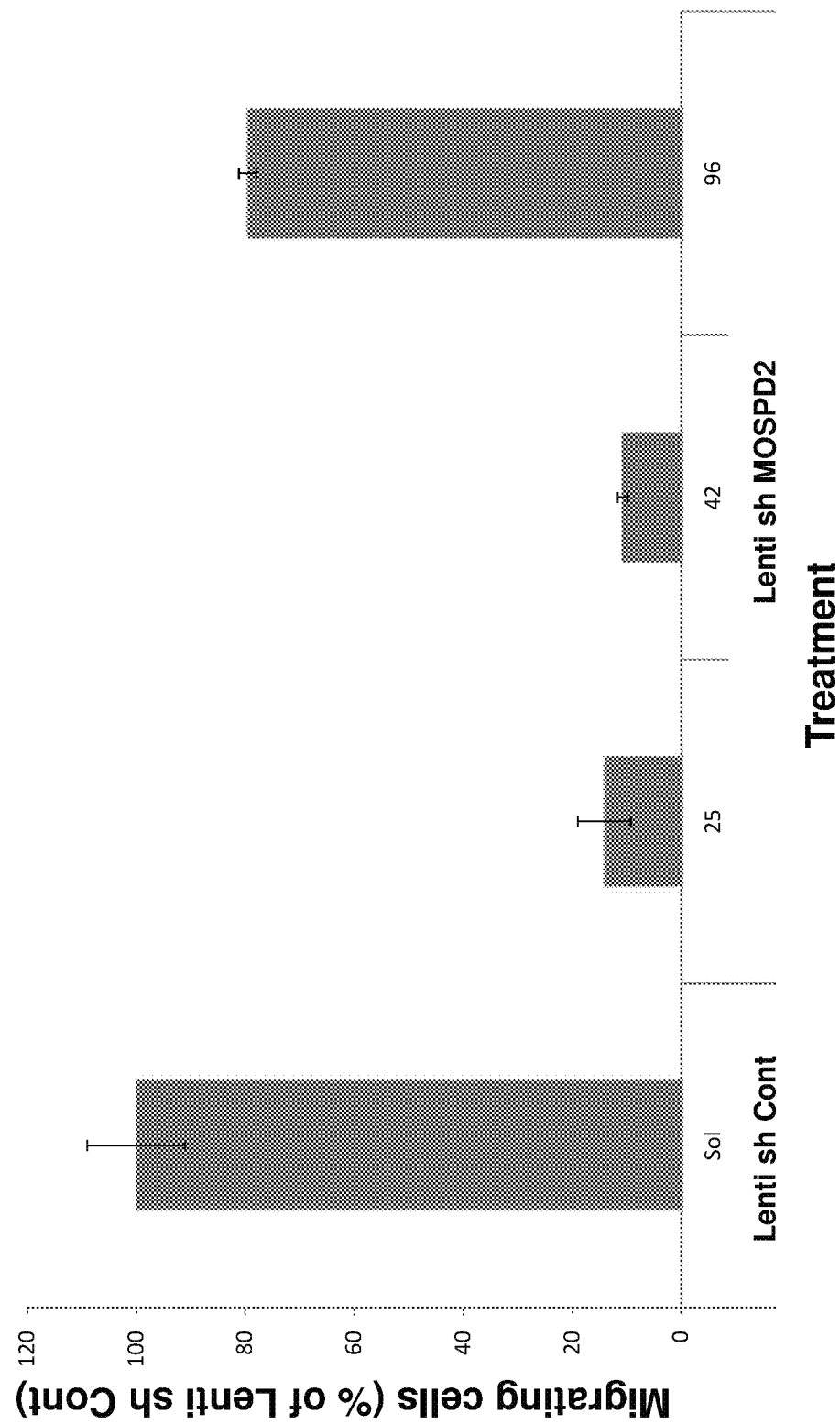

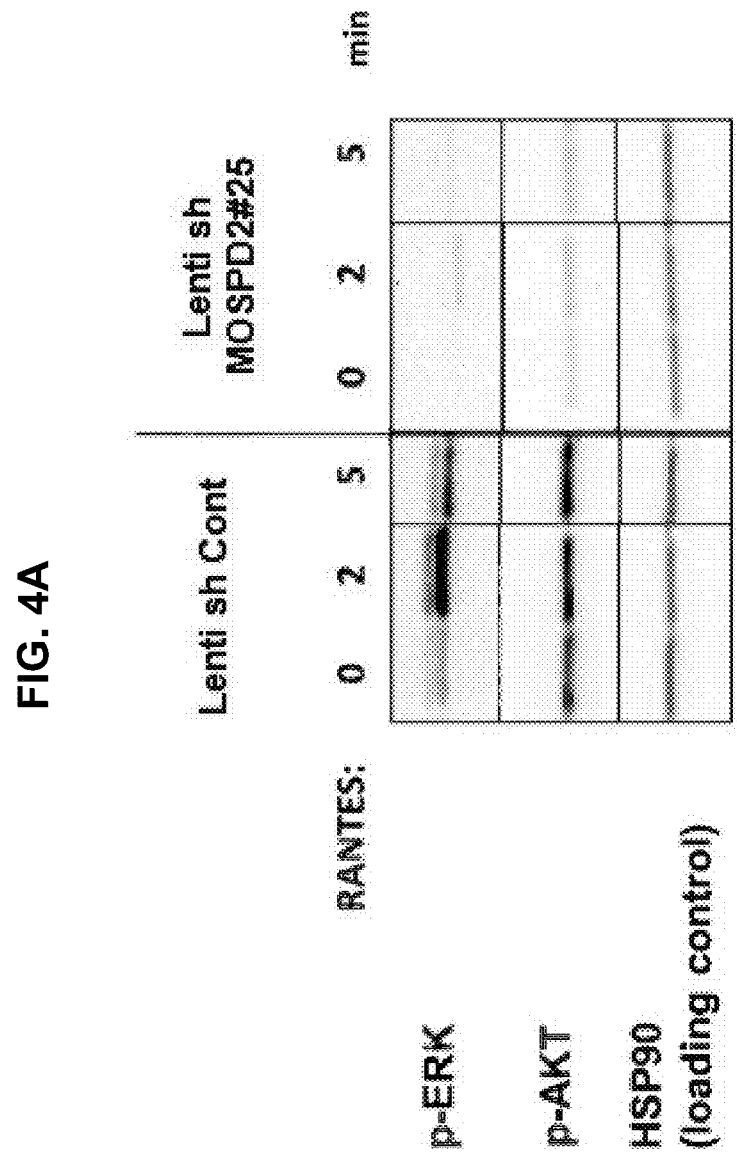

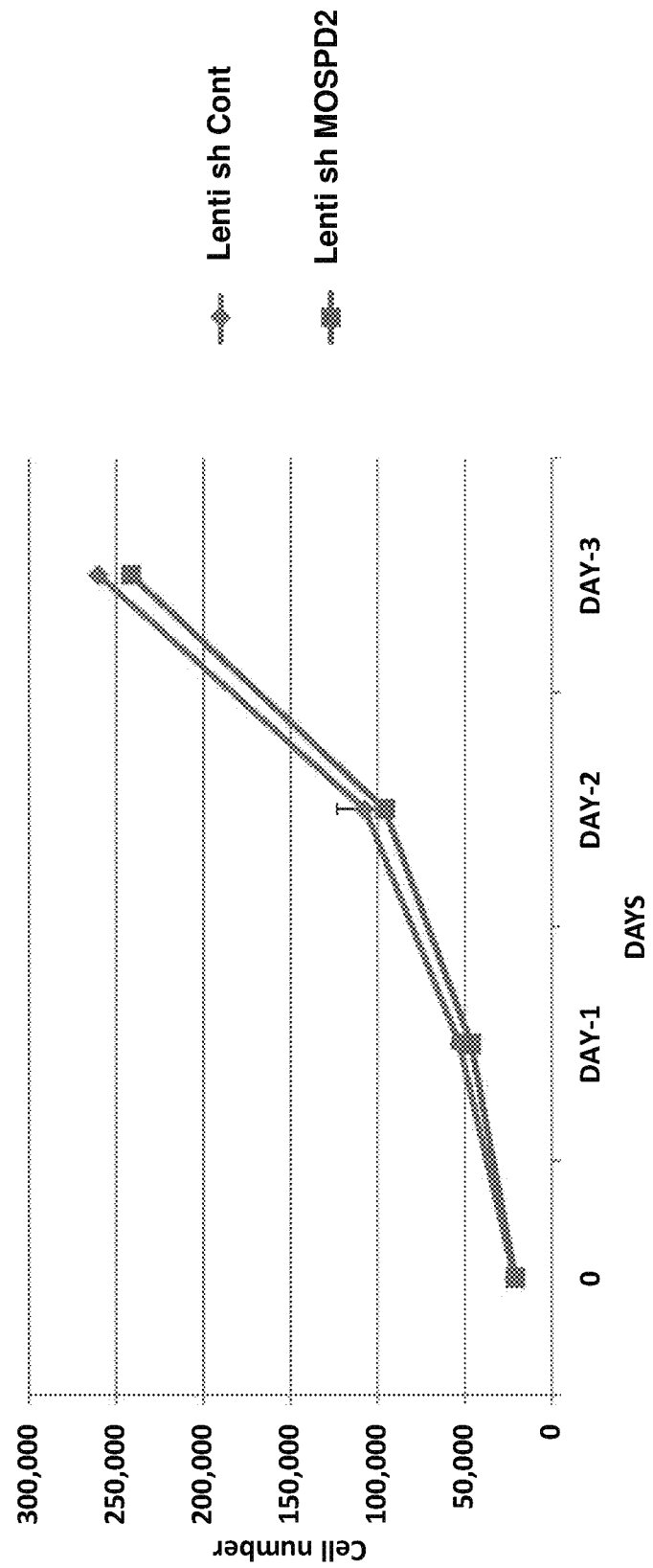

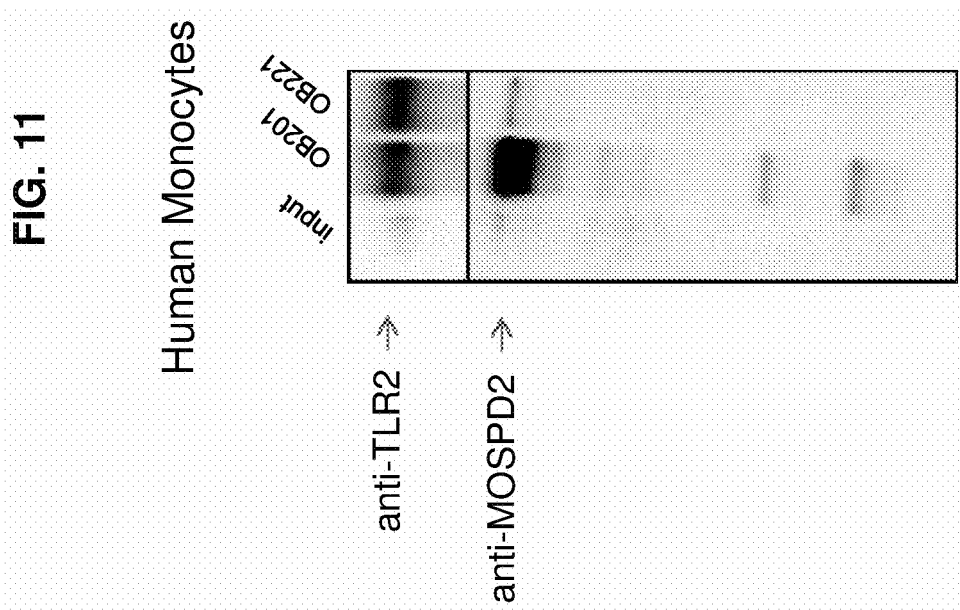

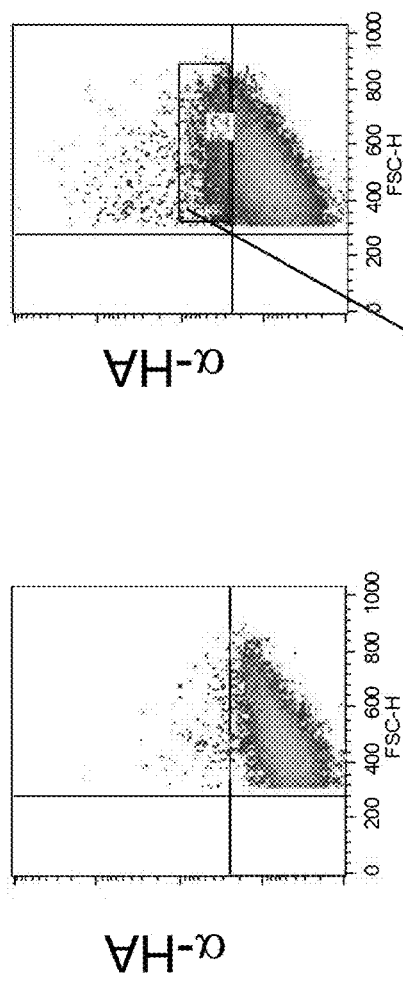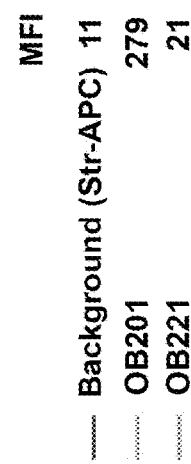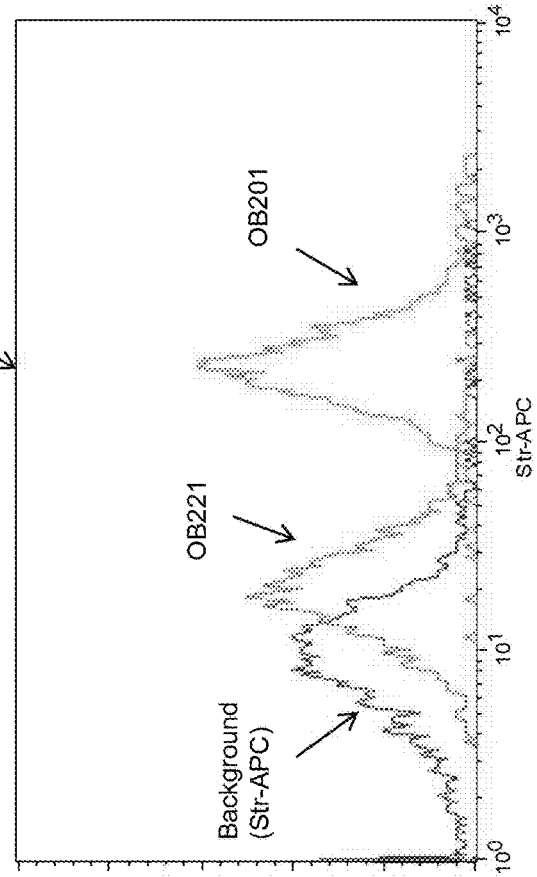

FIG. 13

|  | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| BSA | 1.5 | 0.8 | 1.1 | 0.8 | 0.7 | 1 | 1 | 0.8 | 0.7 | 1 | 0.9 | 0.8 | 0.8 | 0.9 | 0.9 | 0.7 |
| N1 CD33 His6 | 1.6 | 1 | 1.6 | 0.8 | 0.9 | 0.8 | 0.7 | 1 | 0.8 | 0.7 | 0.9 | 1.2 | 1.8 | 1 | 1.5 | 0.8 | 0.9 |
| GST | 1.1 | 0.8 | 1.4 | 1 | 0.8 | 0.8 | 0.7 | 1.5 | 0.7 | 0.7 | 0.6 | 1.1 | 1.1 | 0.8 | 1.1 | 0.8 | 0.8 |
| Fc-Control | 1.2 | 0.9 | 1.1 | 1.3 | 0.8 | 0.8 | 1.6 | 0.8 | 0.6 | 0.7 | 0.8 | 1.1 | | 1.1 | 0.9 | 0.7 | 0.9 |
| MOSPD2-FC | * | * | * |  | * | * | * | * |  |  | * | * |  |  | * | * |  |

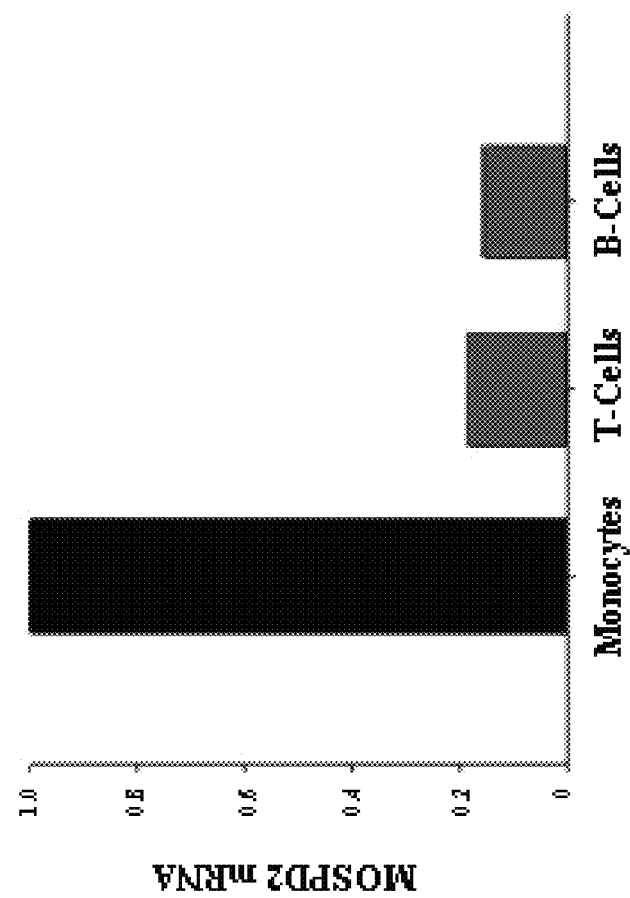

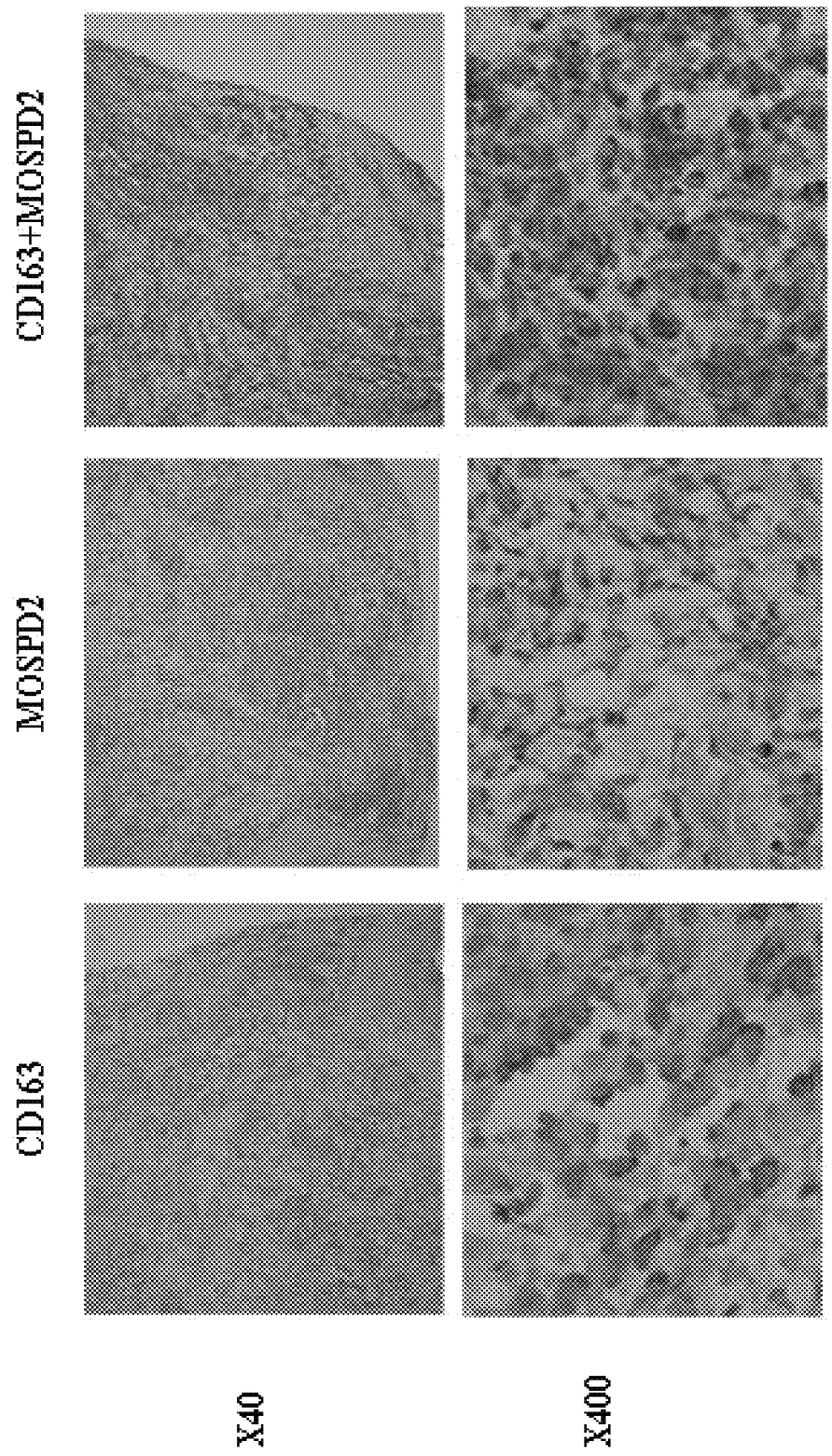

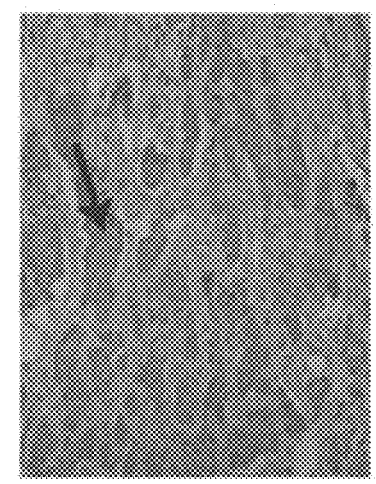 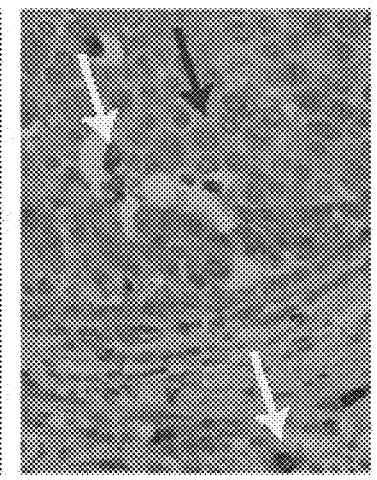
FIG. 16C
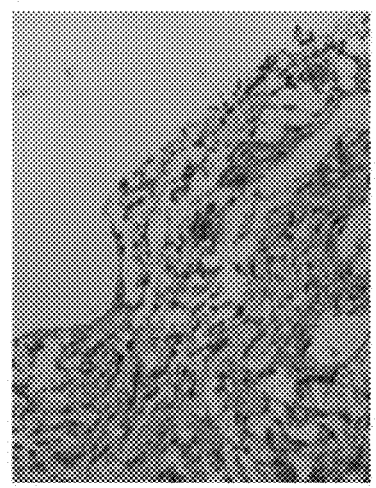 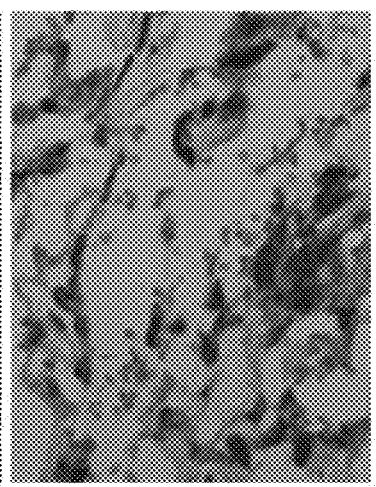
FIG. 16B

SEQUENCE LISTING

```
<160> NUMBER OF SEQ ID NOS: 15

<210> SEQ ID NO 1
<211> LENGTH: 518
<212> TYPE: PRT
<213> ORGANISM: Homo sapiens
<220> FEATURE:
<223> OTHER INFORMATION: motile sperm domain containing 2, protein
      variant 1

<400> SEQUENCE: 1

Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
                20                  25                  30

Asp Ala Arg Asp Val Glu Arg Leu Gln Gln Asp Asn Trp Val Glu
            35                  40                  45

Ser Tyr Leu Ser Trp Arg His Asn Ile Val Asp Glu Thr Leu Lys Met
    50                  55                  60

Leu Asp Glu Ser Phe Gln Trp Arg Lys Glu Ile Ser Val Asn Asp Leu
65                  70                  75                  80

Asn Glu Ser Ser Ile Pro Arg Trp Leu Leu Glu Ile Gly Val Ile Tyr
                85                  90                  95

Leu His Gly Tyr Asp Lys Glu Gly Asn Lys Leu Phe Trp Ile Arg Val
```

```
            100                 105                 110
Lys Tyr His Val Lys Asp Gln Lys Thr Ile Leu Asp Lys Lys Leu
            115                 120                 125
Ile Ala Phe Trp Leu Glu Arg Tyr Ala Lys Arg Glu Asn Gly Lys Pro
            130                 135                 140
Val Thr Val Met Phe Asp Leu Ser Glu Thr Gly Ile Asn Ser Ile Asp
145                 150                 155                 160
Met Asp Phe Val Arg Phe Ile Ile Asn Cys Phe Lys Val Tyr Tyr Pro
                    165                 170                 175
Lys Tyr Leu Ser Lys Ile Val Ile Phe Asp Met Pro Trp Leu Met Asn
            180                 185                 190
Ala Ala Phe Lys Ile Val Lys Thr Trp Leu Gly Pro Glu Ala Val Ser
            195                 200                 205
Leu Leu Lys Phe Thr Ser Lys Asn Glu Val Gln Asp Tyr Val Ser Val
210                 215                 220
Glu Tyr Leu Pro Pro His Met Gly Gly Thr Asp Pro Phe Lys Tyr Ser
225                 230                 235                 240
Tyr Pro Pro Leu Val Asp Asp Phe Gln Thr Pro Leu Cys Glu Asn
                    245                 250                 255
Gly Pro Ile Thr Ser Glu Asp Glu Thr Ser Ser Lys Glu Asp Ile Glu
            260                 265                 270
Ser Asp Gly Lys Glu Thr Leu Glu Thr Ile Ser Asn Glu Glu Gln Thr
            275                 280                 285
Pro Leu Leu Lys Lys Ile Asn Pro Thr Glu Ser Thr Ser Lys Ala Glu
            290                 295                 300
Glu Asn Glu Lys Val Asp Ser Lys Val Lys Ala Phe Lys Lys Pro Leu
305                 310                 315                 320
Ser Val Phe Lys Gly Pro Leu Leu His Ile Ser Pro Ala Glu Glu Leu
                    325                 330                 335
Tyr Phe Gly Ser Thr Glu Ser Gly Glu Lys Lys Thr Leu Ile Val Leu
                    340                 345                 350
Thr Asn Val Thr Lys Asn Ile Val Ala Phe Lys Val Arg Thr Thr Ala
            355                 360                 365
Pro Glu Lys Tyr Arg Val Lys Pro Ser Asn Ser Ser Cys Asp Pro Gly
            370                 375                 380
Ala Ser Val Asp Ile Val Val Ser Pro His Gly Gly Leu Thr Val Ser
385                 390                 395                 400
Ala Gln Asp Arg Phe Leu Ile Met Ala Ala Glu Met Glu Gln Ser Ser
                    405                 410                 415
Gly Thr Gly Pro Ala Glu Leu Thr Gln Phe Trp Lys Glu Val Pro Arg
            420                 425                 430
Asn Lys Val Met Glu His Arg Leu Arg Cys His Thr Val Glu Ser Ser
            435                 440                 445
Lys Pro Asn Thr Leu Thr Leu Lys Asp Asn Ala Phe Asn Met Ser Asp
            450                 455                 460
Lys Thr Ser Glu Asp Ile Cys Leu Gln Leu Ser Arg Leu Leu Glu Ser
465                 470                 475                 480
Asn Arg Lys Leu Glu Asp Gln Val Gln Arg Cys Ile Trp Phe Gln Gln
                    485                 490                 495
Leu Leu Leu Ser Leu Thr Met Leu Leu Leu Ala Phe Val Thr Ser Phe
            500                 505                 510
Phe Tyr Leu Leu Tyr Ser
            515
```

<210> SEQ ID NO 2
<211> LENGTH: 455
<212> TYPE: PRT
<213> ORGANISM: Homo sapiens
<220> FEATURE:
<223> OTHER INFORMATION: motile sperm domain containing 2, protein variant 2

<400> SEQUENCE: 2

```
Met Leu Asp Glu Ser Phe Gln Trp Arg Lys Glu Ile Ser Val Asn Asp
1               5                   10                  15

Leu Asn Glu Ser Ser Ile Pro Arg Trp Leu Glu Ile Gly Val Ile
            20                  25                  30

Tyr Leu His Gly Tyr Asp Lys Glu Gly Asn Lys Leu Phe Trp Ile Arg
        35                  40                  45

Val Lys Tyr His Val Lys Asp Gln Lys Thr Ile Leu Asp Lys Lys Lys
    50                  55                  60

Leu Ile Ala Phe Trp Leu Glu Arg Tyr Ala Lys Arg Glu Asn Gly Lys
65                  70                  75                  80

Pro Val Thr Val Met Phe Asp Leu Ser Glu Thr Gly Ile Asn Ser Ile
                85                  90                  95

Asp Met Asp Phe Val Arg Phe Ile Ile Asn Cys Phe Lys Val Tyr Tyr
            100                 105                 110

Pro Lys Tyr Leu Ser Lys Ile Val Ile Phe Asp Met Pro Trp Leu Met
        115                 120                 125

Asn Ala Ala Phe Lys Ile Val Lys Thr Trp Leu Gly Pro Glu Ala Val
130                 135                 140

Ser Leu Leu Lys Phe Thr Ser Lys Asn Glu Val Gln Asp Tyr Val Ser
145                 150                 155                 160

Val Glu Tyr Leu Pro Pro His Met Gly Gly Thr Asp Pro Phe Lys Tyr
                165                 170                 175

Ser Tyr Pro Pro Leu Val Asp Asp Phe Gln Thr Pro Leu Cys Glu
            180                 185                 190

Asn Gly Pro Ile Thr Ser Glu Asp Glu Thr Ser Ser Lys Glu Asp Ile
        195                 200                 205

Glu Ser Asp Gly Lys Glu Thr Leu Glu Thr Ile Ser Asn Glu Glu Gln
210                 215                 220

Thr Pro Leu Leu Lys Lys Ile Asn Pro Thr Glu Ser Thr Ser Lys Ala
225                 230                 235                 240

Glu Glu Asn Glu Lys Val Asp Ser Lys Val Lys Ala Phe Lys Lys Pro
                245                 250                 255

Leu Ser Val Phe Lys Gly Pro Leu Leu His Ile Ser Pro Ala Glu Glu
            260                 265                 270

Leu Tyr Phe Gly Ser Thr Glu Ser Gly Glu Lys Lys Thr Leu Ile Val
        275                 280                 285

Leu Thr Asn Val Thr Lys Asn Ile Val Ala Phe Lys Val Arg Thr Thr
290                 295                 300

Ala Pro Glu Lys Tyr Arg Val Lys Pro Ser Asn Ser Ser Cys Asp Pro
305                 310                 315                 320

Gly Ala Ser Val Asp Ile Val Val Ser Pro His Gly Gly Leu Thr Val
                325                 330                 335

Ser Ala Gln Asp Arg Phe Leu Ile Met Ala Ala Glu Met Glu Gln Ser
            340                 345                 350

Ser Gly Thr Gly Pro Ala Glu Leu Thr Gln Phe Trp Lys Glu Val Pro
```

```
                355                 360                 365
Arg Asn Lys Val Met Glu His Arg Leu Arg Cys His Thr Val Glu Ser
370                 375                 380

Ser Lys Pro Asn Thr Leu Thr Leu Lys Asp Asn Ala Phe Asn Met Ser
385                 390                 395                 400

Asp Lys Thr Ser Glu Asp Ile Cys Leu Gln Leu Ser Arg Leu Leu Glu
                405                 410                 415

Ser Asn Arg Lys Leu Glu Asp Gln Val Gln Arg Cys Ile Trp Phe Gln
            420                 425                 430

Gln Leu Leu Leu Ser Leu Thr Met Leu Leu Leu Ala Phe Val Thr Ser
                435                 440                 445

Phe Phe Tyr Leu Leu Tyr Ser
450                 455

<210> SEQ ID NO 3
<211> LENGTH: 486
<212> TYPE: PRT
<213> ORGANISM: Homo sapiens
<220> FEATURE:
<223> OTHER INFORMATION: motile sperm domain containing 2, protein
      variant X1

<400> SEQUENCE: 3

Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
                20                  25                  30

Asp Ala Arg Asp Val Glu Arg Leu Gln Gln Asp Asp Asn Trp Val Glu
            35                  40                  45

Ser Tyr Leu Ser Trp Arg His Asn Ile Val Asp Glu Thr Leu Lys Met
        50                  55                  60

Leu Asp Glu Ser Phe Gln Trp Arg Lys Glu Ile Ser Val Asn Asp Leu
65              70                  75                  80

Asn Glu Ser Ser Ile Pro Arg Trp Leu Leu Glu Ile Gly Val Ile Tyr
                85                  90                  95

Leu His Gly Tyr Asp Lys Glu Gly Asn Lys Leu Phe Trp Ile Arg Val
            100                 105                 110

Lys Tyr His Val Lys Asp Gln Lys Thr Ile Leu Asp Lys Lys Lys Leu
        115                 120                 125

Ile Ala Phe Trp Leu Glu Arg Tyr Ala Lys Arg Glu Asn Gly Lys Pro
130                 135                 140

Val Thr Val Met Phe Asp Leu Ser Glu Thr Gly Ile Asn Ser Ile Asp
145                 150                 155                 160

Met Asp Phe Val Arg Phe Ile Ile Asn Cys Phe Lys Val Tyr Tyr Pro
                165                 170                 175

Lys Tyr Leu Ser Lys Ile Val Ile Phe Asp Met Pro Trp Leu Met Asn
            180                 185                 190

Ala Ala Phe Lys Ile Val Lys Thr Trp Leu Gly Pro Glu Ala Val Ser
        195                 200                 205

Leu Leu Lys Phe Thr Ser Lys Asn Glu Val Gln Asp Tyr Val Ser Val
    210                 215                 220

Glu Tyr Leu Pro Pro His Met Gly Gly Thr Asp Pro Phe Lys Tyr Ser
225                 230                 235                 240

Tyr Pro Pro Leu Val Asp Asp Asp Phe Gln Thr Pro Leu Cys Glu Asn
                245                 250                 255
```

-continued

```
Gly Pro Ile Thr Ser Glu Asp Glu Thr Ser Ser Lys Glu Asp Ile Glu
            260                 265                 270

Ser Asp Gly Lys Glu Thr Leu Glu Thr Ile Ser Asn Glu Glu Gln Thr
        275                 280                 285

Pro Leu Leu Lys Lys Ile Asn Pro Thr Glu Ser Thr Ser Lys Ala Glu
    290                 295                 300

Glu Asn Glu Lys Val Asp Ser Lys Val Lys Ala Phe Lys Lys Pro Leu
305                 310                 315                 320

Ser Val Phe Lys Gly Pro Leu His Ile Ser Pro Ala Glu Glu Leu
                325                 330                 335

Tyr Phe Gly Ser Thr Glu Ser Gly Glu Lys Lys Thr Leu Ile Val Leu
            340                 345                 350

Thr Asn Val Thr Lys Asn Ile Val Ala Phe Lys Val Arg Thr Thr Ala
        355                 360                 365

Pro Glu Lys Tyr Arg Val Lys Pro Ser Asn Ser Ser Cys Asp Pro Gly
    370                 375                 380

Ala Ser Val Asp Ile Val Val Ser Pro His Gly Gly Leu Thr Val Ser
385                 390                 395                 400

Ala Gln Asp Arg Phe Leu Ile Met Ala Ala Glu Met Glu Gln Ser Ser
                405                 410                 415

Gly Thr Gly Pro Ala Glu Leu Thr Gln Phe Trp Lys Glu Val Pro Arg
            420                 425                 430

Asn Lys Val Met Glu His Arg Leu Arg Cys His Thr Val Glu Ser Ser
        435                 440                 445

Lys Pro Asn Thr Leu Thr Leu Lys Asp Asn Ala Phe Asn Met Ser Asp
    450                 455                 460

Lys Thr Ser Glu Asp Ile Cys Leu Gln Phe Ala Thr Ser Ser Cys Glu
465                 470                 475                 480

Met Asp Cys Ser Pro Pro
                485

<210> SEQ ID NO 4
<211> LENGTH: 475
<212> TYPE: PRT
<213> ORGANISM: Homo sapiens
<220> FEATURE:
<223> OTHER INFORMATION: motile sperm domain containing 2, protein
      variant X2

<400> SEQUENCE: 4

Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
            20                  25                  30

Asp Ala Arg Asp Val Glu Arg Leu Gln Gln Asp Asn Trp Val Glu
        35                  40                  45

Ser Tyr Leu Ser Trp Arg His Asn Ile Val Asp Glu Thr Leu Lys Met
    50                  55                  60

Leu Asp Glu Ser Phe Gln Trp Arg Lys Glu Ile Ser Val Asn Asp Leu
65                  70                  75                  80

Asn Glu Ser Ser Ile Pro Arg Trp Leu Leu Glu Ile Gly Val Ile Tyr
                85                  90                  95

Leu His Gly Tyr Asp Lys Glu Gly Asn Lys Leu Phe Trp Ile Arg Val
            100                 105                 110

Lys Tyr His Val Lys Asp Gln Lys Thr Ile Leu Asp Lys Lys Lys Leu
        115                 120                 125
```

```
Ile Ala Phe Trp Leu Glu Arg Tyr Ala Lys Arg Glu Asn Gly Lys Pro
        130                 135                 140
Val Thr Val Met Phe Asp Leu Ser Glu Thr Gly Ile Asn Ser Ile Asp
145                 150                 155                 160
Met Asp Phe Val Arg Phe Ile Ile Asn Cys Phe Lys Val Tyr Tyr Pro
                165                 170                 175
Lys Tyr Leu Ser Lys Ile Val Ile Phe Asp Met Pro Trp Leu Met Asn
            180                 185                 190
Ala Ala Phe Lys Ile Val Lys Thr Trp Leu Gly Pro Glu Ala Val Ser
        195                 200                 205
Leu Leu Lys Phe Thr Ser Lys Asn Glu Val Gln Asp Tyr Val Ser Val
    210                 215                 220
Glu Tyr Leu Pro Pro His Met Gly Gly Thr Asp Pro Phe Lys Tyr Ser
225                 230                 235                 240
Tyr Pro Pro Leu Val Asp Asp Phe Gln Thr Pro Leu Cys Glu Asn
                245                 250                 255
Gly Pro Ile Thr Ser Glu Asp Glu Thr Ser Ser Lys Glu Asp Ile Glu
                260                 265                 270
Ser Asp Gly Lys Glu Thr Leu Gly Thr Ile Ser Asn Glu Glu Gln Thr
            275                 280                 285
Pro Leu Leu Lys Lys Ile Asn Pro Thr Glu Ser Thr Ser Lys Ala Glu
        290                 295                 300
Glu Asn Glu Lys Val Asp Ser Lys Val Lys Ala Phe Lys Lys Pro Leu
305                 310                 315                 320
Ser Val Phe Lys Gly Pro Leu Leu His Ile Ser Pro Ala Glu Glu Leu
                325                 330                 335
Tyr Phe Gly Ser Thr Glu Ser Gly Glu Lys Lys Thr Leu Ile Val Leu
            340                 345                 350
Thr Asn Val Thr Lys Asn Ile Val Ala Phe Lys Val Arg Thr Thr Ala
        355                 360                 365
Pro Glu Lys Tyr Arg Val Lys Pro Ser Asn Ser Ser Cys Asp Pro Gly
    370                 375                 380
Ala Ser Val Asp Ile Val Val Ser Pro His Gly Gly Leu Thr Val Ser
385                 390                 395                 400
Ala Gln Asp Arg Phe Leu Ile Met Ala Ala Glu Met Glu Gln Ser Ser
                405                 410                 415
Gly Thr Gly Pro Ala Glu Leu Thr Gln Phe Trp Lys Glu Val Pro Arg
            420                 425                 430
Asn Lys Val Met Glu His Arg Leu Arg Cys His Thr Val Glu Ser Ser
        435                 440                 445
Lys Pro Asn Thr Leu Thr Leu Lys Asp Asn Ala Phe Asn Met Ser Asp
    450                 455                 460
Lys Thr Ser Glu Asp Ile Cys Leu Gln Tyr Ser
465                 470                 475

<210> SEQ ID NO 5
<211> LENGTH: 3219
<212> TYPE: DNA
<213> ORGANISM: Homo sapiens
<220> FEATURE:
<223> OTHER INFORMATION: motile sperm domain containing 2, transcript
      variant 1, mRNA, coding region 125-1678

<400> SEQUENCE: 5
accgcctccc cctcccaccc ttctctgtct acctctgggc gggactgccg ggtgatgaga    60
```

-continued

```
tactcggtcg gcgacggtag aacgggcgac ggcgacaacc gcaatcacat ccacgacggt    120
gatcatggca gagaatcacg cccagaataa agccaagctc atctctgaga cccggaggag    180
gttcgaagct gagtatgtga cagataagtc agataaatat gatgcacgtg atgttgaaag    240
gctacaacaa gatgataact gggttgaaag ttacttatct tggagacata atattgtaga    300
tgaaacactg aagatgctcg atgagagttt tcagtggagg aaagaaattt ctgtcaatga    360
ccttaatgaa tcctccattc ccagatggtt attggaaatt ggtgttattt atctccatgg    420
ttatgacaaa gaaggtaaca aattgttctg gatcagggtg aagtatcatg taaaagacca    480
gaaaaccata ttggacaaaa agaagctcat agcattctgg ttggaacgtt atgctaagag    540
ggaaaatggg aaacctgtaa cagtgatgtt tgacctgtca gaaactggaa taaatagcat    600
tgacatggac tttgtacgct ttatcatcaa ctgctttaag gtttattacc ctaaatacct    660
ctcaaaaata gtgatctttg atatgccttg gttaatgaat gctgctttca aaattgtgaa    720
aacctggctt ggtccagaag cagtgagctt gttgaagttt acaagcaaaa atgaagtcca    780
ggactatgtc agtgtagaat acctgcctcc ccacatgggt ggaactgatc ctttcaagta    840
tagctatcca ccactagtag atgatgactt ccagacccca ctgtgtgaga atgggcctat    900
taccagtgag gatgaaactt caagtaaaga agacatagaa agtgatggca agaaacatt    960 ggaaacaatt tctaatgaag aacaaacacc tcttcttaaa aagattaacc caaccgaatc   1020
tacttccaaa gcagaagaaa atgaaaaagt tgattcaaaa gtgaaagctt tcaagaaacc   1080
attgagtgta tttaaaggcc ccttactaca catcagccca gcagaagaac tgtactttgg   1140
aagtacagaa tccggagaga agaaaacctt aatagtgttg acaaatgtaa ctaaaaatat   1200
agtggcattt aaggtgagaa caacagctcc agaaaaatac agagtcaagc caagcaatag   1260
cagctgtgac ccgggtgcat cagtggatat agttgtgtct ccccatgggg gtttaacagt   1320
ctctgcccaa gaccgttttc tgataatggc tgcagaaatg gaacagtcat ctggcacagg   1380
cccagcagaa ttaactcagt tttggaaaga agttcccaga aacaaagtga tggaacatag   1440
gttaagatgc catactgttg aaagcagtaa accaaacact cttacgttaa agacaatgc   1500 tttcaatatg tcagataaaa ccagtgaaga tatatgtcta caactcagtc gtttactaga   1560
aagcaatagg aagcttgaag accaagttca gcgttgtatc tggttccagc agctgctgct   1620
ttccttaaca atgctcttgc ttgcttttgt cacctctttc ttctatttat tgtacagtta   1680
aagaagtggt gccgggtagg aaccacggtt ccttcgtcca ttagttggaa aaagtaacag   1740
acctaaaact ctaccaagct actaaaaaca ttgcacatct gtgcttccta aaggaaata   1800 tgcagcacgt ggagggaac acatacatgt cttgaaaata aactgctaga ataaagaaat   1860
gctggagaaa ttgattataa gagactatag ctatttagta aagtaagtaa aggcatatcc   1920
attgtgtaaa ttaatagttt aaatataatt tattttttcc ttttgatctg aatactttta   1980
aagcttaagt tttatcgtgt aaatacatta gctaaactga aaagtataag taacatgctt   2040
tgttgcagcc aaaaaatgta atctgctttt ttatgacaga attattatag ctgagctgac   2100
ttactagctt ttctatacta tgtatataga agaacatgta tattgagaaa gaaaacatac   2160
ttatatagag gaatttatgt aaccatgact ttgtaatttt gagaattcct cccagtgatg   2220
gtcagtattc ttttggaatg taaaccgatt taatgccaaa ccaccttaac ctttgtttct   2280
cagtgttcct taacagcctg ccttttatta atctcaggct tttttatgaa cactctcatt   2340
tcagtagaat ttggaaaact aagcgtggtt ggaatttctt tgaattctgt tagtaatgcc   2400
```

-continued

| | |
|---|---|
| caaaagaaaa gtctcaagca gtcccccctat ccagtcattt ttatggagtt tcatgttgtc | 2460 |
| cactatagct ggacactgaa ccttttgcct aatttattat aaaggcctga ccctctattg | 2520 |
| tcccatcttc accccccattc cagagcagag gagtctctgt ggaccatgaa ttgcactgtc | 2580 |
| tccctcctca tttctaaatg aaaggtatta gatataaatt tttttgaaag gttagttgtt | 2640 |
| tgagatgcta agcaggataa taaatttaga ttttaaaatg ttccctgtaa aagtcagccc | 2700 |
| atgacaagga aatttacaaa atactagagt atctagaagg gtgaaaacaa aaaaaaataa | 2760 |
| aaagaaacac agacgcccag gtgtcagctc tccgtttaaa gaatgaaaaa tgtaactcat | 2820 |
| gatgatctgt gaaaccttca aactaggacc aattgactta cttgatattc tgcctttgat | 2880 |
| atggtagtac ccacccggta ttcctaaaat cctaaaaaga tacaccttgc agtagcagag | 2940 |
| gcaatgacat gagtttgttt tctcattaat atgaccagtt tgggtctatg ttggttcaca | 3000 |
| tgtacatcta ctttatatga aagaaaaaac agttgtctgc ctgtaaaatg ttgagtttcg | 3060 |
| attgagccat gtttggagat tttattacta ttctgaaggg tagtgttgtt ggttttcatc | 3120 |
| ttcaagaagt tgattccaaa actgagttat gaagaatgat ataacagttc cttcaaaatt | 3180 |
| ggcctaggaa ataaaacctt aaaaggacaa aaaaaaaaa | 3219 |

<210> SEQ ID NO 6
<211> LENGTH: 3183
<212> TYPE: DNA
<213> ORGANISM: Homo sapiens
<220> FEATURE:
<223> OTHER INFORMATION: motile sperm domain containing 2, transcript
      variant 2, mRNA, coding region 278-1642

<400> SEQUENCE: 6

| | |
|---|---|
| agtcacaata ataggtactt aaaaacatgt catatgatag gaaactagaa taacacacct | 60 |
| ctaaataatc catggattac caacttctca gcaatggtgt aaattcttct gctaaataac | 120 |
| ccgtgggtta aagaggacat cacattggaa attccagagt acttaaaata agtcagataa | 180 |
| atatgatgca cgtgatgttg aaaggctaca acaagatgat aactgggttg aaagttactt | 240 |
| atcttggaga cataatattg tagatgaaac actgaagatg ctcgatgaga gttttcagtg | 300 |
| gaggaaagaa atttctgtca atgaccttaa tgaatcctcc attcccagat ggttattgga | 360 |
| aattggtgtt atttatctcc atggttatga caaagaaggt aacaaattgt tctggatcag | 420 |
| ggtgaagtat catgtaaaag accagaaaac catattggac aaaaagaagc tcatagcatt | 480 |
| ctggttggaa cgttatgcta agagggaaaa tgggaaacct gtaacagtga tgtttgacct | 540 |
| gtcagaaact ggaataaata gcattgacat ggactttgta cgctttatca tcaactgctt | 600 |
| taaggtttat taccctaaat acctctcaaa aatagtgatc tttgatatgc cttggttaat | 660 |
| gaatgctgct ttcaaaattg tgaaaacctg gcttggtcca gaagcagtga gcttgttgaa | 720 |
| gtttacaagc aaaaatgaag tccaggacta tgtcagtgta gaatacctgc ctccccacat | 780 |
| gggtggaact gatcctttca gtatagcta tccaccacta gtagatgatg acttccagac | 840 |
| cccactgtgt gagaatgggc ctattaccag tgaggatgaa acttcaagta agaagacat | 900 |
| agaaagtgat ggcaaagaaa cattggaaac aatttctaat gaagaacaaa cacctcttct | 960 |
| taaaaagatt aacccaaccg aatctacttc caaagcagaa gaaaatgaaa aagttgattc | 1020 |
| aaaagtgaaa gctttcaaga aaccattgag tgtatttaaa ggccccttac tacacatcag | 1080 |
| cccagcagaa gaactgtact ttggaagtac agaatccgga gagaagaaaa ccttaatagt | 1140 |
| gttgacaaat gtaactaaaa atatagtggc atttaaggtg agaacaacag ctccagaaaa | 1200 |

| | |
|---|---|
| atacagagtc aagccaagca atagcagctg tgacccgggt gcatcagtgg atatagttgt | 1260 |
| gtctccccat gggggtttaa cagtctctgc ccaagaccgt tttctgataa tggctgcaga | 1320 |
| aatggaacag tcatctggca caggcccagc agaattaact cagttttgga agaagttcc | 1380 |
| cagaaacaaa gtgatggaac ataggttaag atgccatact gttgaaagca gtaaaccaaa | 1440 |
| cactcttacg ttaaaagaca atgctttcaa tatgtcagat aaaaccagtg aagatatatg | 1500 |
| tctacaactc agtcgtttac tagaaagcaa taggaagctt gaagaccaag ttcagcgttg | 1560 |
| tatctggttc cagcagctgc tgcttttcctt aacaatgctc ttgcttgctt ttgtcacctc | 1620 |
| tttcttctat ttattgtaca gttaaagaag tggtgccggg taggaaccac ggttccttcg | 1680 |
| tccattagtt ggaaaaagta acagacctaa aactctacca agctactaaa acattgcac | 1740 |
| atctgtgctt cctaaaagga aatatgcagc acgtggaggg gaacacatac atgtcttgaa | 1800 |
| aataaactgc tagaataaag aaatgctgga gaaattgatt ataagagact atagctattt | 1860 |
| agtaaagtaa gtaaaggcat atccattgtg taaattaata gtttaaatat aatttatttt | 1920 |
| ttccttttga tctgaatact tttaaagctt aagtttatc gtgtaaatac attagctaaa | 1980 |
| ctgaaaagta taagtaacat gctttgttgc agccaaaaaa tgtaatctgc ttttttatga | 2040 |
| cagaattatt atagctgagc tgacttacta gcttttctat actatgtata tagaagaaca | 2100 |
| tgtatattga gaaagaaaac atacttatat agaggaattt atgtaaccat gactttgtaa | 2160 |
| ttttgagaat tcctcccagt gatggtcagt attcttttgg aatgtaaacc gatttaatgc | 2220 |
| caaaccacct taacctttgt ttctcagtgt tccttaacag cctgcctttt attaatctca | 2280 |
| ggcttttta tgaacactct catttcagta gaatttggaa actaagcgt ggttggaatt | 2340 |
| tctttgaatt ctgttagtaa tgcccaaaag aaaagtctca agcagtcccc ctatccagtc | 2400 |
| attttatgg agtttcatgt tgtccactat agctggacac tgaaccttttt gcctaattta | 2460 |
| ttataaaggc ctgaccctct attgtcccat cttcaccccc attccagagc agaggagtct | 2520 |
| ctgtggacca tgaattgcac tgtctccctc ctcatttcta aatgaaaggt attagatata | 2580 |
| aatttttttg aaaggttagt tgtttgagat gctaagcagg ataataaatt tagattttaa | 2640 |
| aatgttccct gtaaaagtca gcccatgaca aggaaattta caaaatacta gagtatctag | 2700 |
| aagggtgaaa acaaaaaaaa ataaaaagaa acacagacgc ccaggtgtca gctctccgtt | 2760 |
| taaagaatga aaaatgtaac tcatgatgat ctgtgaaacc ttcaaactag gaccaattga | 2820 |
| cttacttgat attctgcctt tgatatggta gtacccaccc ggtattccta aaatcctaaa | 2880 |
| aagatacacc ttgcagtagc agaggcaatg acatgagttt gttttctcat taatatgacc | 2940 |
| agtttgggtc tatgttggtt cacatgtaca tctactttat atgaaagaaa aaacagttgt | 3000 |
| ctgcctgtaa aatgttgagt ttcgattgag ccatgtttgg agattttatt actattctga | 3060 |
| agggtagtgt tgttggtttt catcttcaag aagttgattc caaaactgag ttatgaagaa | 3120 |
| tgatataaca gttccttcaa aattggccta ggaaataaaa ccttaaaagg acaaaaaaaa | 3180 |
| aaa | 3183 |

<210> SEQ ID NO 7
<211> LENGTH: 2330
<212> TYPE: DNA
<213> ORGANISM: Homo sapiens
<220> FEATURE:
<223> OTHER INFORMATION: motile sperm domain containing 2, transcript
      variant X1, mRNA, coding region 125-1582

<400> SEQUENCE: 7

-continued

```
accgcctccc cctcccaccc ttctctgtct acctctgggc gggactgccg ggtgatgaga    60
tactcggtcg cgacggtag aacgggcgac ggcgacaacc gcaatcacat ccacgacggt    120
gatcatggca gagaatcacg cccagaataa agccaagctc atctctgaga cccggaggag    180
gttcgaagct gagtatgtga cagataagtc agataaatat gatgcacgtg atgttgaaag    240
gctacaacaa gatgataact gggttgaaag ttacttatct tggagacata atattgtaga    300
tgaaacactg aagatgctcg atgagagttt tcagtggagg aaagaaattt ctgtcaatga    360
ccttaatgaa tcctccattc ccagatggtt attggaaatt ggtgttattt atctccatgg    420
ttatgacaaa gaaggtaaca aattgttctg gatcagggtg aagtatcatg taaaagacca    480
gaaaaccata ttggacaaaa agaagctcat agcattctgg ttggaacgtt atgctaagag    540
ggaaaatggg aaacctgtaa cagtgatgtt tgacctgtca gaaactggaa taaatagcat    600
tgacatggac tttgtacgct ttatcatcaa ctgctttaag gtttattacc ctaaataccct   660
ctcaaaaata gtgatctttg atatgccttg gttaatgaat gctgctttca aaattgtgaa    720
aacctggctt ggtccagaag cagtgagctt gttgaagttt acaagcaaaa atgaagtcca    780
ggactatgtc agtgtagaat acctgcctcc ccacatgggt ggaactgatc ctttcaagta    840
tagctatcca ccactagtag atgatgactt ccagaccccca ctgtgtgaga atgggcctat    900
taccagtgag gatgaaactt caagtaaaga agacatagaa agtgatggca agaaacatt    960
ggaaacaatt tctaatgaag aacaaacacc tcttcttaaa aagattaacc caaccgaatc   1020
tacttccaaa gcagaagaaa atgaaaaagt tgattcaaaa gtgaaagctt tcaagaaacc   1080
attgagtgta tttaaaggcc ccttactaca catcagccca gcagaagaac tgtactttgg   1140
aagtacagaa tccggagaga agaaaaacctt aatagtgttg acaaatgtaa ctaaaaatat   1200
agtggcattt aaggtgagaa caacagctcc agaaaaatac agagtcaagc caagcaatag   1260
cagctgtgac ccgggtgcat cagtggatat agttgtgtct ccccatgggg gtttaacagt   1320
ctctgcccaa gaccgttttc tgataatggc tgcagaaatg gaacagtcat ctggcacagg   1380
cccagcagaa ttaactcagt tttggaaaga agttcccaga aacaaagtga tggaacatag   1440
gttaagatgc catactgttg aaagcagtaa accaaacact cttacgttaa agacaatgc    1500
tttcaatatg tcagataaaa ccagtgaaga tatatgtcta caatttgcca cctccagctg   1560
tgaaatggac tgcagtccac cctaagtact gtgcacagta tctccctgtg tgtgtgcaca   1620
gtggcttccc cttacatggt agatttttgg ccttaatata atctaatccc aaagtagttg   1680
tgtatgtttt ctgttccttg gcaaataaat gaagaaataa ttagccaaga ttgaaaatgt   1740
attgtcctaa cggtgtccct ttaatgtttc atatgaaaaa ttatgttgac ccactaaaat   1800
atccttgctc aatgtctggt cagttgaatt taataacata tcttgttaat gtttgtgtgt   1860
ctattaaatg tgactaagca ggattactga aaattcacta taaaatcaaa ggcatctaaa   1920
cgtttgtact tgtcttgatt aatcatatat ttacacttga ttttttttctg tcttcatttg   1980
tttttattta atcataattg catgattttt ttggtactct aatcagtaat tttattttta   2040
atcatgtcat tacctattca tgaccaaatt accaaggaac caacatttag atttagatat   2100
ttgttttcac ttaggaatgg aaattaatag atttttccatg aaagcattag tgaaatatca   2160
ttaccttgat ctgcaagtag cctaaaaatg cgattgctgg taaacctggc ctcaaatttc   2220
atactaccat aactgttttt atatattgcc actaattttg actggattta atagcacttt   2280
attgtacaac tacaaaaaaa aatatattcc tagaattgtt gccagtgtaa               2330
```

<210> SEQ ID NO 8
<211> LENGTH: 3909
<212> TYPE: DNA
<213> ORGANISM: Homo sapiens
<220> FEATURE:
<223> OTHER INFORMATION: motile sperm domain containing 2, transcript
      variant X2, mRNA, coding region 125-1549

<400> SEQUENCE: 8

| | | | | | |
|---|---|---|---|---|---|
| accgcctccc | cctcccaccc | ttctctgtct | acctctgggc | gggactgccg | ggtgatgaga | 60 |
| tactcggtcg | gcgacggtag | aacgggcgac | ggcgacaacc | gcaatcacat | ccacgacggt | 120 |
| gatcatggca | gagaatcacg | cccagaataa | agccaagctc | atctctgaga | cccggaggag | 180 |
| gttcgaagct | gagtatgtga | cagataagtc | agataaatat | gatgcacgtg | atgttgaaag | 240 |
| gctacaacaa | gatgataact | gggttgaaag | ttacttatct | tggagacata | atattgtaga | 300 |
| tgaaacactg | aagatgctcg | atgagagttt | tcagtggagg | aaagaaattt | ctgtcaatga | 360 |
| ccttaatgaa | tcctccattc | ccagatggtt | attggaaatt | ggtgttattt | atctccatgg | 420 |
| ttatgacaaa | gaaggtaaca | aattgttctg | gatcagggtg | aagtatcatg | taaaagacca | 480 |
| gaaaaccata | ttggacaaaa | agaagctcat | agcattctgg | ttgaacgtt | atgctaagag | 540 |
| ggaaaatggg | aaacctgtaa | cagtgatgtt | tgacctgtca | gaaactggaa | taaatagcat | 600 |
| tgacatggac | tttgtacgct | ttatcatcaa | ctgctttaag | gtttattacc | ctaaatacct | 660 |
| ctcaaaaata | gtgatctttg | atatgccttg | gttaatgaat | gctgctttca | aaattgtgaa | 720 |
| aacctggctt | ggtccagaag | cagtgagctt | gttgaagttt | acaagcaaaa | atgaagtcca | 780 |
| ggactatgtc | agtgtagaat | acctgcctcc | ccacatgggt | ggaactgatc | ctttcaagta | 840 |
| tagctatcca | ccactagtag | atgatgactt | ccagacccca | ctgtgtgaga | atgggcctat | 900 |
| taccagtgag | gatgaaactt | caagtaaaga | agacatagaa | agtgatggca | agaaacatt | 960 |
| ggaaacaatt | tctaatgaag | aacaaacacc | tcttcttaaa | aagattaacc | caaccgaatc | 1020 |
| tacttccaaa | gcagaagaaa | atgaaaaagt | tgattcaaaa | gtgaaagctt | tcaagaaacc | 1080 |
| attgagtgta | tttaaaggcc | ccttactaca | catcagccca | gcagaagaac | tgtactttgg | 1140 |
| aagtacagaa | tccggagaga | agaaaaacctt | aatagtgttg | acaaatgtaa | ctaaaaatat | 1200 |
| agtggcattt | aaggtgagaa | caacagctcc | agaaaaatac | agagtcaagc | caagcaatag | 1260 |
| cagctgtgac | ccgggtgcat | cagtggatat | agttgtgtct | ccccatgggg | gtttaacagt | 1320 |
| ctctgcccaa | gaccgttttc | tgataatggc | tgcagaaatg | gaacagtcat | ctggcacagg | 1380 |
| cccagcagaa | ttaactcagt | tttggaaaga | agttcccaga | aacaaagtga | tggaacatag | 1440 |
| gttaagatgc | catactgttg | aaagcagtaa | accaaacact | cttacgttaa | aagacaatgc | 1500 |
| tttcaatatg | tcagataaaa | ccagtgaaga | tatatgtcta | caatacagtt | aaagaagtgg | 1560 |
| tgccgggtag | gaaccacggt | tccttcgtcc | attagttgga | aaagtaaca | gacctaaaac | 1620 |
| tctaccaagc | tactaaaaac | attgcacatc | tgtgcttcct | aaaaggaaat | atgcagcacg | 1680 |
| tggagggaa | cacatacatg | tcttgaaaat | aaactgctag | aataaagaaa | tgctggagaa | 1740 |
| attgattata | agagactata | gctatttagt | aaagtaagta | aaggcatatc | cattgtgtaa | 1800 |
| attaatagtt | taaatataat | ttattttttc | cttttgatct | gaatactttt | aaagcttaag | 1860 |
| ttttatcgtg | taaatacatt | agctaaactg | aaaagtataa | gtaacatgct | tgttgcagc | 1920 |
| caaaaaatgt | aatctgcttt | tttatgacag | aattattata | gctgagctga | cttactagct | 1980 |
| tttctatact | atgtatatag | aagaacatgt | atattgagaa | agaaaacata | cttatataga | 2040 |
| ggaatttatg | taaccatgac | tttgtaattt | tgagaattcc | tcccagtgat | ggtcagtatt | 2100 |

```
cttttggaat gtaaaccgat ttaatgccaa accaccttaa cctttgtttc tcagtgttcc    2160
ttaacagcct gccttttatt aatctcaggc ttttttatga acactctcat ttcagtagaa    2220
tttggaaaac taagcgtggt tggaatttct ttgaattctg ttagtaatgc caaaagaaa     2280
agtctcaagc agtcccccta tccagtcatt tttatggagt ttcatgttgt ccactatagc    2340
tggacactga accttttgcc taatttatta taaaggcctg accctctatt gtcccatctt    2400
caccccatt ccagagcaga ggagtctctg tggaccatga attgcactgt ctccctcctc     2460
atttctaaat gaaaggtatt agatataaat ttttttgaaa ggttagttgt ttgagatgct    2520
aagcaggata taaatttag attttaaaat gttccctgta aaagtcagcc catgacaagg     2580
aaatttacaa atactagag tatctagaag ggtgaaaaca aaaaaaata aaagaaaca       2640
cagacgccca ggtgtcagct ctccgtttaa agaatgaaaa atgtaactca tgatgatctg    2700
tgaaaccttc aaactaggac caattgactt acttgatatt ctgcctttga tatggtagta    2760
cccacccggt attcctaaaa tcctaaaaag atacaccttg cagtagcaga ggcaatgaca    2820
tgagtttgtt ttctcattaa tatgaccagt ttgggtctat gttggttcac atgtacatct    2880
actttatatg aaagaaaaaa cagttgtctg cctgtaaaat gttgagtttc gattgagcca    2940
tgtttggaga ttttattact attctgaagg gtagtgttgt tggttttcat cttcaagaag    3000
ttgattccaa aactgagtta tgaagaatga tataacagtt ccttcaaaat tggcctagga    3060
aataaaacct taaaggaca ctggtgtgct actttgtctt aatttgggct ttctgtttc      3120
agtttgccac ctccagctgt gaaatggact gcagtccacc ctaagtactg tgcacagtat    3180
ctccctgtgt gtgtgcacag tggcttcccc ttacatggta gattttggc cttaatataa     3240
tctaatccca agtagttgt gtatgttttc tgttccttgg caaataaatg aagaaataat     3300
tagccaagat tgaaaatgta ttgtcctaac ggtgtccctt taatgtttca tatgaaaaat    3360
tatgttgacc cactaaaata tccttgctca atgtctggtc agttgaattt aataacatat    3420
cttgttaatg tttgtgtgtc tattaaatgt gactaagcag gattactgaa aattcactat    3480
aaaatcaaag gcatctaaac gtttgtactt gtcttgatta atcatatatt tacacttgat    3540
tttttctgt cttcatttgt ttttatttaa tcataattgc atgattttt tggtactcta     3600
atcagtaatt ttatttttaa tcatgtcatt acctattcat gaccaaatta ccaaggaacc    3660
aacatttaga tttagatatt tgttttcact taggaatgga aattaataga ttttccatga    3720
aagcattagt gaaatatcat taccttgatc tgcaagtagc ctaaaaatgc gattgctggt    3780
aaacctggcc tcaaatttca tactaccata actgtttta tatattgcca ctaattttga    3840
ctggatttaa tagcactttta ttgtacaact acaaaaaaaa atatattcct agaattgttg    3900
ccagtgtaa                                                            3909

<210> SEQ ID NO 9
<211> LENGTH: 58
<212> TYPE: DNA
<213> ORGANISM: Artificial Sequence
<220> FEATURE:
<223> OTHER INFORMATION: shRNA hairpin sequence #1 for MOSPD2

<400> SEQUENCE: 9
ccggcccaga tggttattgg aaattctcga gatttccaat aaccatctgg gtttttg        58

<210> SEQ ID NO 10
<211> LENGTH: 21
<212> TYPE: DNA
```

```
<213> ORGANISM: Artificial Sequence
<220> FEATURE:
<223> OTHER INFORMATION: target sequence on MOSPD2 for shRNA hairpin
      sequence #1

<400> SEQUENCE: 10
cccagatggt tattggaaat t                                              21

<210> SEQ ID NO 11
<211> LENGTH: 59
<212> TYPE: DNA
<213> ORGANISM: Artificial Sequence
<220> FEATURE:
<223> OTHER INFORMATION: shRNA hairpin sequence #2 for MOSPD2

<400> SEQUENCE: 11
ccgggccata ctgttgaaag cagtactcga gtactgcttt caacagtatg gctttttg     59

<210> SEQ ID NO 12
<211> LENGTH: 21
<212> TYPE: DNA
<213> ORGANISM: Artificial Sequence
<220> FEATURE:
<223> OTHER INFORMATION: MOSPD2 target sequence for shRNA hairpin
      sequence #2

<400> SEQUENCE: 12
gccatactgt tgaaagcagt a                                              21

<210> SEQ ID NO 13
<211> LENGTH: 59
<212> TYPE: DNA
<213> ORGANISM: Artificial Sequence
<220> FEATURE:
<223> OTHER INFORMATION: shRNA hairpin sequence #3 for MOSPD2

<400> SEQUENCE: 13
ccggccctcc tcatttctaa atgaactcga gttcatttag aaatgaggag gttttttg     59

<210> SEQ ID NO 14
<211> LENGTH: 21
<212> TYPE: DNA
<213> ORGANISM: Artificial Sequence
<220> FEATURE:
<223> OTHER INFORMATION: MOSPD2 target sequence for shRNA hairpin
      sequence #3

<400> SEQUENCE: 14
ccctcctcat ttctaaatga a                                              21

<210> SEQ ID NO 15
<211> LENGTH: 9
<212> TYPE: PRT
<213> ORGANISM: Artificial Sequence
<220> FEATURE:
<223> OTHER INFORMATION: Hemagglutinin tag for MOSPD2

<400> SEQUENCE: 15

Tyr Pro Tyr Asp Val Pro Asp Tyr Ala
1               5
```

MOTILE SPERM DOMAIN CONTAINING PROTEIN 2 AND INFLAMMATION

RELATED APPLICATIONS

This application is a continuation of U.S. application Ser. No. 15/747,918, § 371(c) date Jan. 26, 2018, which is the U.S. national phase entry of Int'l Appl. No. PCT/IB2016/054582, filed Jul. 29, 2016, which claims priority to U.S. Provisional Appl. No. 62/199,609, filed Jul. 31, 2015. These applications are incorporated herein by reference in their entireties.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Sep. 8, 2020, is named "31820620003 Sequence-Listing.txt", and is 36,120 bytes in size.

FIELD OF THE INVENTION

This invention relates to anti-inflammatory processes, for example, methods of treating, preventing, or reducing the incidence of one or more activities in a cell, or one or more inflammatory diseases or disorders with an inhibitor of Motile Sperm Domain containing Protein 2 (MOSPD2). The invention also relates to pharmaceutical compositions comprising one or more inhibitors of MOSPD2.

BACKGROUND OF THE INVENTION

Leukocytes are the cells of the immune system that are involved in defending the body against infectious disease and foreign materials. Monocytes are a type of leukocytes and have critical roles in innate and adaptive immunity, immune surveillance, and particle scavenging. While a subset of monocytes is "resident" and recruited to tissues independently of inflammatory stimuli to assist in steady-state surveillance, wound-healing and resolution of inflammation, the majority (80-90%) of human circulating monocytes are classified as "inflammatory." Circulating monocytes can sense inflammatory stimuli and quickly migrate through the vascular or lymphatic endothelium to the periphery, where they can differentiate into macrophages and dendritic cells (DCs) which cooperate with additional cell subsets to promote inflammation. While playing a necessary role in host defense, monocytes are nonetheless identified as critical mediators of several inflammatory disorders, including atherosclerosis, rheumatoid arthritis (RA), and multiple sclerosis (MS).

Chemokine receptors and adhesion molecules play a key role in regulation of leukocyte trafficking. A complex array of chemokine receptors, G-protein coupled receptors (GPCRs) that are differentially expressed on leukocyte lineages and subsets, regulates which cell types would migrate and to which tissue, under different conditions. Chemokines or chemotactic cytokines are secreted proteins that regulate migration and activation of leukocytes and stromal cells. Binding of chemokines to chemokine receptors activates signaling pathways such as the MAPK/ERK and PI3K/AKT pathways, resulting in phosphorylation of ERK and AKT, respectively. In the case of inflammatory monocytes, exit from the bone marrow across a monolayer of endothelial cells (diapedesis) to enter the circulatory system (intravasation) and to migrate to the inflamed tissue is dependent on C-C motif receptor 2 (CCR2) signaling, in response to activation by chemokine C-C motif ligand (CCL) 2 (also known as monocyte chemotactic protein-1; MCP-1) and CCL7 (MCP-3). On the other hand, constitutive migration of resident monocytes to non-inflamed tissues is mostly dependent on CCL3 (also known as Macrophage inflammatory protein-1a; MIP-1a) and chemokine (C-X3-C motif) ligand 1 (CX3CL1).

Inhibition of inflammatory cell migration (e.g., leukocyte chemotaxis) towards inflammatory sites is an attractive anti-inflammatory approach to treat chronic diseases. Suppressing the accumulation of unwanted monocytes and/or macrophages in chronically inflamed tissue has therapeutic potential, and migration inhibitors have accordingly demonstrated beneficial therapeutic results in animal models and clinical trials. Nevertheless, there have been several phase II clinical trial failures with chemokine and chemokine receptor antagonists, possibly due to redundancy of the target receptor and the complexity of heterogeneous diseases such as multiple sclerosis and rheumatoid arthritis.

Furthermore, inhibition of inflammation is also relevant to the treatment of osteoporosis, because inflammation exerts influence on bone turnover, inducing osteoporosis.

Motile Sperm Domain containing Protein 2 (MOSPD2) is a 518-amino acid long, highly conserved protein with 90% homology between human and mouse. Bioinformatic analyses indicate that MOSPD2 contains a CRAL-TRIO region, named after the cellular retinaldehyde-binding protein (CRALBP) and the TRIO protein. MOSPD2 also contains a structurally related region to the nematode major sperm protein and one transmembrane region. A biological function for MOSPD2 has not yet been described.

SUMMARY OF THE INVENTION

The present invention, in some embodiments, relates to methods of treating, preventing, or reducing the incidence of an inflammatory disease or disorder with an inhibitor of Motile Sperm Domain containing Protein 2 (MOSPD2), and to methods of inhibiting or preventing one or more activities in a cell with an inhibitor of MOSPD2. In some embodiments, the invention relates to various methods of treatment or prevention, including methods of treating, preventing, or reducing the incidence of an inflammatory disease or disorder, comprising administering to a subject in need thereof a therapeutically effective amount of an inhibitor of MOSPD2. In other embodiments, the invention relates to a method of inhibiting, preventing, or reducing the incidence of one or more activities in a cell, comprising administering to a subject in need thereof a therapeutically effective amount of an inhibitor of MOSPD2, wherein the one or more activities is one or more of: MOSPD2 expression, inflammatory cell migration (e.g., leukocyte or monocyte migration), chemotaxis (e.g., leukocyte or monocyte chemotaxis), a chemokine signaling pathway, ERK phosphorylation and AKT phosphorylation. In some embodiments, the inhibitor of MOSPD2 is an antibody or antigen binding fragment thereof. In other embodiments, the antibody is a polyclonal, monoclonal, murine, human, humanized, or chimeric antibody. In some embodiments, the invention relates to various methods of inhibiting MOSPD2 in a cell, comprising contacting the cell with an effective amount of an inhibitor of MOSPD2.

In some embodiments, the inhibitor of MOSPD2 is a small molecule, such as an oxidized phospholipid. In one preferred embodiment, the inhibitor of MOSPD2 is VB-201.

In some embodiments, the inhibitor of MOSPD2 is an inhibitor of MOSPD2 that is not an oxidized phospholipid. In some embodiments, the inhibitor of MOSPD2 is an inhibitor of MOSPD2 that is not VB-201. In some embodiments, the inhibitor of MOSPD2 binds to MOSPD2 expressed on a cell surface (e.g., an inflammatory cell surface).

In other embodiments, the invention also relates to polypeptides that inhibit MOSPD2 and pharmaceutical compositions containing a polypeptide that inhibits MOSPD2. In some embodiments, the polypeptide is an antibody or antigen binding fragment thereof.

In some embodiments, the antibody or antigen binding fragment thereof specifically binds to MOSPD2. In other embodiments, the antibody or antigen binding fragment thereof binds to MOSPD2 with an equilibrium dissociation constant ($K_D$) of from about $10^{-6}$ M to about $10^{-12}$ M. In other embodiments, the MOSPD2 is human MOSPD2. In other embodiments, the antibody or antigen binding fragment thereof specifically binds to one or more of the following amino acid regions of human MOSPD2, numbered according to SEQ ID NO:1: about 508 to about 517, about 501 to about 514, about 233 to about 241, about 509 to about 517, about 212 to about 221, about 13 to about 24, about 505 to about 517, about 505 to about 514, about 89 to about 100, about 506 to about 517, about 233 to about 245, about 504 to about 514, about 128 to about 136, about 218 to about 226, about 15 to about 24, about 83 to about 96, about 42 to about 50, about 462 to about 474, about 340 to about 351, about 504 to about 517, about 462 to about 470, about 327 to about 337, about 21 to about 32, about 217 to about 226, about 510 to about 517, about 178 to about 190, about 497 to about 509, about 504 to about 516, about 64 to about 77, about 504 to about 515, about 147 to about 159, about 503 to about 515, about 88 to about 97, about 208 to about 218, about 178 to about 191, about 502 to about 515, about 503 to about 516, about 497 to about 505, about 500 to about 509, about 189 to about 202, about 189 to about 197, about 505 to about 516, about 1 to about 63, about 82 to about 239, about 93 to about 234, about 327 to about 445, about 327 to about 431, and about 497 to about 517.

In some embodiments, the antibody or antigen binding fragment thereof specifically binds to one or more of the following amino acid regions of human MOSPD2, numbered according to SEQ ID NO:1: about 505 to about 515, about 500 to about 515, about 230 to about 240, about 510 to about 520, about 210 to about 220, about 15 to about 25, about 505 to about 520, about 505 to about 515, about 90 to about 100, about 505 to about 525, about 230 to about 245, about 505 to about 510, about 130 to about 140, about 220 to about 230, about 15 to about 30, about 80 to about 95, about 40 to about 50, about 460 to about 475, about 340 to about 350, about 500 to about 515, about 460 to about 470, about 325 to about 335, about 20 to about 35, about 215 to about 225, about 510 to about 520, about 175 to about 190, about 500 to about 510, about 505 to about 530, about 60 to about 75, about 500 to about 520, about 145 to about 160, about 502 to about 515, about 85 to about 100, about 205 to about 220, about 175 to about 190, about 500 to about 505, about 500 to about 525, about 495 to about 505, about 495 to about 510, about 190 to about 200, about 190 to about 198, about 502 to about 515, about 1 to about 60, about 80 to about 240, about 90 to about 235, about 330 to about 445, about 330 to about 430, and about 495 to about 515.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

FIG. 2 shows the effect of MOSPD2 inhibition on RANTES-induced U937 cell migration. U937 cells transduced with control Lenti-virus particles (Lenti sh-Cont) or sh-MOSPD2 (Lenti sh-MOSPD2 were tested for migration towards RANTES in a trans-well assay. The results shown are mean percentages of migrating cells±standard deviation of triplicate wells. *$p<0.05$.

FIG. 3 shows further effects of MOSPD2 inhibition on RANTES-induced U937 cell migration. U937 cells transduced with control Lenti-virus particles (Lenti sh-Cont) or sh-MOSPD2 (Lenti sh-MOSPD2) directed against different regions on the gene transcript (Lenti sh #25 or Lenti sh #42 or Lenti #96) were treated with solvent (Sol), and then tested for migration towards RANTES in a trans-well assay. The results shown are the mean percentages of migrating cells±standard deviation of triplicate wells.

FIG. 4A and FIG. 4B present images of Western blots showing the effect of MOSPD2 inhibition on phosphorylated ERK (p-ERK) and phosphorylated AKT (p-AKT) levels after activation with RANTES. U937 cells transduced with control Lenti-virus particles (Lenti sh-Cont) or sh-MOSPD2 (Lenti sh-MOSPD2 #25 or Lenti sh-MOSPD2 #42) were treated with RANTES for 2 or 5 minutes. FIG. 4A shows results with Lenti sh-MOSPD2 #25. FIG. 4B shows results with Lenti sh-MOSPD2 #42. Expression of heat shock protein 90 (HSP90) is also shown as a loading control.

FIG. 7 shows the effect of MOSPD2 inhibition on U937 cell proliferation. U937 cells transduced with control Lenti-virus particles (Lenti sh-Cont, -♦-) or sh-MOSPD2 Lenti-virus particles (Lenti sh-MOSPD2, -■-) were seeded and counted every 24 hours for three consecutive days (DAY-1, DAY-2 and DAY-3). The results shown are the mean cell numbers per day±standard deviation of triplicates.

In FIG. 8A, cell lysate was prepared from U937 cells transduced with control or sh-MOSPD2 Lenti-virus particles (Lenti sh-Control or Lenti sh-MOSPD2, respectively). Samples were loaded on a gel and blotted with the isolated α-MOSPD2 antibodies. Expression of HSP90 was also determined as a loading control. In FIG. 8B, U937 cell lysate was immunoprecipitated with the isolated α-MOSPD2 antibodies or rabbit IgG as a control. The resulting precipitates were analyzed by immunoblot with the isolated α-MOSPD2 antibodies, followed by incubation with goat anti-rabbit antibody-HRP.

FIG. 10 is based on an analysis of subcellular protein fractions of human CD14 monocytes and membrane (M) and cytoplasmic (C) fractions, using anti-MOSPD2 antibody. Anti-ERK or anti-MHC Class I antibodies were used to evaluate fractionation purity of cytoplasmic and membrane proteins, respectively.

FIG. 11 presents images of Western blots showing that VB-201 binds to MOSPD2 from cell lysate of human CD14 monocytes. Labelled VB-201 or VB-221 (OB201 or OB221) was added to the cell lysate and proteins were precipitated. Samples were run on a gel and blotted against TLR2 and MOSPD2 with the results shown in FIG. 11.

FIGS. 12A-12C show that HEK293 cells positively stained for hemagglutinin (HA) have a strong binding to OB201, but not OB221. FIGS. 12A-12B show that VB-201 binds to MOSPD2 on the cell surface of HEK293 cells transfected with HA-tagged MOSPD2 expression vector (FIG. 12B), but not cells transfected with empty vector (FIG. 12A). In FIG. 12C, the HEK293 cells were incubated with labelled VB-201 or VB-221 (OB201 or OB221) followed by streptavidin-APC stain (Str-APC).

FIG. 13 lists 17 anti-MOSPD2 F(ab')2 monoclonal antibody (mAb) clones that were identified following a primary screen for binding to cells over-expressing MOSPD2. Further analysis of the clones for MOSPD2 binding with enzyme-linked immunosorbent assay (ELISA) identified 12 clones having O.D. values greater than 5 times over background (* in FIG. 13).

FIGS. 15A-15D show the cellular expression specificity and localization of MOSPD2.

FIGS. 16A-16C show MOSPD2 is expressed on monocytes that have infiltrated into inflamed tissues.

DETAILED DESCRIPTION OF THE INVENTION

Figure 1:
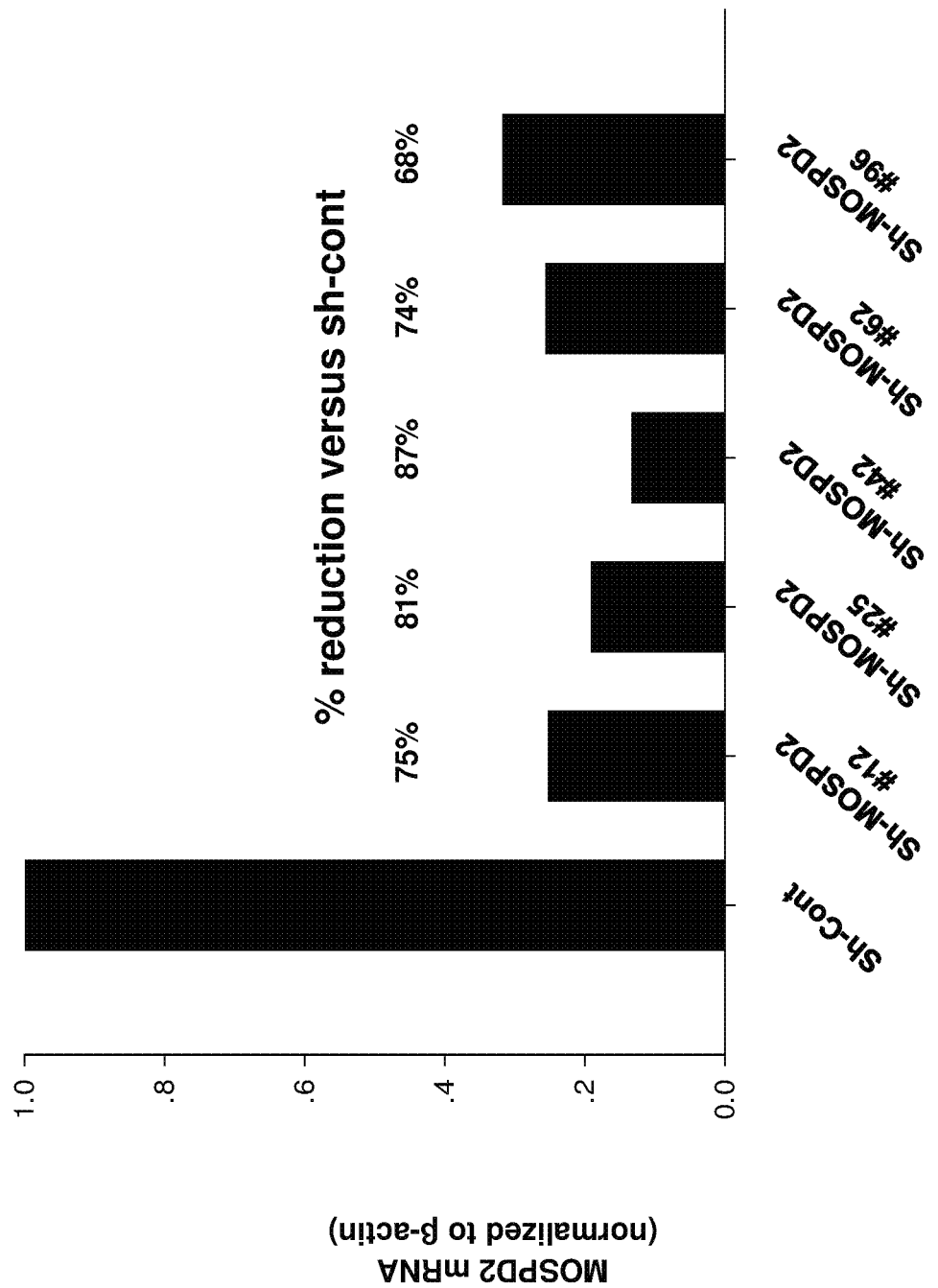
FIG. 1 shows the inhibition of Motile Sperm Domain containing Protein 2 (MOSPD2) mRNA expression obtained with small hairpin RNA (sh-RNA) against MOSPD2 (sh-MOSPD2). U937 cells were transduced with control Lenti-virus particles (sh-Cont) or Lenti-virus particles directed against three different mRNA regions of MOSPD2 (marked as Sh-MOSPD2 #12, #25, #42, #62, and #96). MOSPD2 mRNA expression in the cells was assessed using quantitative polymerase chain reaction (PCR) and normalized using β-actin expression. The percentage decrease of MOSPD2 expression with sh-MOSPD2 compared to sh-control is indicated.

Before explaining embodiments of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

General Definitions

The terms "comprises", "comprising", "includes", "including", "having", and their conjugates mean "including but not limited to."

The term "consisting of" means "including and limited to."

The term "consisting essentially of" means the specified material of a composition, or the specified steps of a method, and those additional materials or steps that do not materially affect the basic characteristics of the material or method.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention can include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. Whether or not modified by the term "about", the claims include equivalents of the recited quantities. In one embodiment, the term "about" means within 10% of the reported numerical value. In another embodiment, the term "about" means within 5% of the reported numerical value.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, "MOSPD2" refers to any polypeptide classified as Motile Sperm Domain containing Protein 2. Examples of MOSPD2 include, but are not limited to, the polypeptides of SEQ ID NOs:1-4, or any variant thereof (e.g., having a sequence at least 75%, at least 80%, at least 85%, at least 90%, at least 95%, at least 96%, at least 97%, at least 98%, or at least 99% identical to any one of SEQ ID NOs:1-4). Other examples of MOSPD2 include, but are not limited to, a polypeptide encoded by a polynucleotide of any one of SEQ ID NOs:5-8, or any variant thereof (e.g., a polynucleotide having at least 75%, at least 80%, at least 85%, at least 90%, at least 95%, at least 96%, at least 97%, at least 98%, or at least 99% identical to any one of SEQ ID NOs:5-8). Polynucleotide sequences encoding MOSPD2 can be codon optimized for expression in a particular organism by methods known in the art. Other examples of MOSPD2 can be identified by searching public databases (e.g., BLAST), as well known to one skilled in the art.

As used herein, "an activity of MOSPD2" or "a MOSPD2 activity" include any known or herein described function of Motile Sperm Domain containing Protein 2. Such activities include, for example, regulation of inflammatory cell migration (e.g., leukocyte or monocyte migration), chemotaxis, chemokine-induced leukocyte migration or chemotaxis, chemokine receptor signaling pathways, growth factor signaling pathways, EGF receptor phosphorylation, ERK phosphorylation, AKT phosphorylation, FAK phosphorylation, or inflammation.

As used herein, "an inflammatory cell" includes, but is not limited to a leukocyte, granulocyte, neutrophil, basophil, eosinophil, monocyte, macrophage, or mast cell.

As used herein, "chemotaxis" refers to the movement of a cell in response to a chemical stimulus. Chemotaxis includes, but is not limited to, the movement of an inflammatory cell such as a monocyte to a chemokine.

As used herein, "an inhibitor of MOSPD2" and "a MOSPD2 inhibitor" refer to any compound which downregulates an activity of MOSPD2. The inhibitor can be, for example, a polypeptide, DNA, or RNA Inhibition of MOSPD2 can also occur, for example, by ectopic overexpression of MOSPD2 by infection, and it is intended that an inhibitor of MOSPD2 or a MOSPD2 inhibitor encompasses this type of inhibition. The inhibitor can also be, for example, a molecule that specifically binds to a MOSPD2 polypeptide, a molecule that specifically binds to a ligand of a MOSPD2 polypeptide, an antisera raised against a MOSPD2 polypeptide, a soluble MOSPD2 polypeptide, or a soluble MOSPD2 polypeptide comprising, consisting essentially of, or consisting of an extracellular domain of a MOSPD2 polypeptide. The inhibitor can also be, for example, an antibody that specifically binds to a MOSPD2 polypeptide or an antigen binding fragment of an antibody that specifically binds to a MOSPD2 polypeptide. The inhibitor can also be, for example, an RNAi, miRNA, siRNA, shRNA, antisense RNA, antisense DNA, decoy molecule, decoy DNA, double-stranded DNA, single-stranded DNA, complexed DNA, encapsulated DNA, viral DNA, plasmid DNA, naked RNA, encapsulated RNA, viral RNA, double-stranded RNA, molecule capable of generating RNA interference, or combinations thereof, that hybridizes to a nucleotide sequence encoding a MOSPD2 polypeptide. The inhibitor can also be a small molecule chemical compound which downregulates an activity of MOSPD2.

The inhibitor can also be, for example, a clustered regularly interspaced short palindromic repeats CRISPR-CAS9 system. CRISPR-CAS9 systems have been described in the literature and can include, for example, CAS9 and a guide RNA. Other gene editing techniques have also been described in the literature and can also be used.

An "antibody" or an "antigen binding fragment" of an antibody include, but are not limited to, polyclonal, monoclonal, murine, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), a light chain variable region (VL) or a heavy chain variable region (VH) domain, fragments comprising either a VL or VH domain, and fragments produced by a Fab expression library. An antibody or antigen binding fragment of an antibody can be of any type (e.g., IgG, IgE, IgM, IgD, IgA, and IgY), class (e.g., IgG1, IgG2, IgG3, IgG4, IgA1 and IgA2) or subclass of immunoglobulin molecule. Methods for making an antigen binding fragment of an antibody are known and include, for example, chemical or protease digestion of an antibody.

A "constant region" of an antibody refers to the constant region of the antibody light chain or the constant region of the antibody heavy chain, either alone or in combination.

The term "Fc region" is used to define a C-terminal region of an immunoglobulin heavy chain. The "Fc region" can be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3.

By "specifically binds," it is generally meant that an antibody or fragment, variant, or derivative thereof binds to an epitope by its antigen-binding domain, and that the binding entails some complementarity between the antigen binding domain and the epitope. According to this definition, an antibody or fragment, variant, or derivative thereof is said to "specifically bind" to an epitope when it binds to that epitope via its antigen-binding domain more readily than it would bind to a random, unrelated epitope.

As used herein, an "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by methods described in the literature and herein, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping).

The term "percent identity," as known in the art, is a relationship between two or more polypeptide sequences or two or more polynucleotide sequences, as determined by comparing the sequences. In the art, "identity" and "sequence identity" also mean the degree of sequence relatedness between polypeptide or polynucleotide sequences, as the case may be, as determined by the match between strings of such sequences. "Identity" and "similarity" can be readily calculated by known methods and publicly available resources, including but not limited to those described in: (1) Computational Molecular Biology (Lesk, A. M., Ed.) Oxford University: NY (1988); (2) Biocomputing: Informatics and Genome Projects (Smith, D. W., Ed.) Academic: NY (1993); (3) Computer Analysis of Sequence Data, Part I (Griffin, A. M., and Griffin, H. G., Eds.) Humania: NJ (1994); (4) Sequence Analysis in Molecular Biology (von Heinje, G., Ed.) Academic (1987); and (5) Sequence Analysis Primer (Gribskov, M. and Devereux, J., Eds.) Stockton: NY (1991).

A polynucleotide can "hybridize" to another polynucleotide, when a single-stranded form of the nucleic acid fragment can anneal to the other nucleic acid fragment under the appropriate conditions of temperature and solution ionic strength. Hybridization and washing conditions are well known and exemplified, for example, in Sambrook et al., Molecular Cloning: A Laboratory Manual, 2nd ed., Cold Spring Harbor Laboratory: Cold Spring Harbor, N.Y. (1989), particularly Chapter 11 and Table 11.1 therein (incorporated herein by reference in its entirety). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One exemplary set of stringent conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of exemplary stringent conditions uses higher temperatures in which the washes are identical to those above except for the temperature of the final two 30 min washes in 0.2×SSC, 0.5% SDS was increased to 60° C. This set of stringent conditions can be modified to a "highly stringent condition" by adding two final washes in 0.1×SSC, 0.1% SDS at 65° C. An additional exemplary set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA: RNA, DNA:RNA, DNA:DNA. For hybrids of greater than 100 nucleotides in length, equations for calculating Tm have been derived (see Sambrook et al., 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment, the length for a hybridizable nucleic acid is at least about 10 nucleotides. In other embodiments, a minimum length for a hybridizable nucleic acid is at least about 15 nucleotides, or at least about 20 nucleotides.

As used herein throughout, the term "alkyl" refers to a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. In some embodiments, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, 0-carbamyl, N-carbamyl, 0-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, 0-carbamyl, N-carbamyl, 0-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, 0-carbamyl, N-carbamyl, 0-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, 0-carbamyl, N-carbamyl, 0-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, 0-carbamyl, N-carbamyl, 0-thiocarbamyl, N-thiocarbamyl, C-amido, N-amido, C-carboxy, O-carboxy, sulfonamido, and amino, as these terms are defined herein. Representative examples are piperidine, piperazine, tetrahydro furane, tetrahydropyrane, morpholino and the like.

An "alkoxy" group refers to both an —O-alkyl and an —O-cycloalkyl group, as defined herein.

An "aryloxy" group refers to both an —O-aryl and an —O-heteroaryl group, as defined herein.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R group, where R is hydrogen, alkyl, alkenyl, cycloalkyl, aryl, heteroaryl (bonded through a ring carbon) or heteroalicyclic (bonded through a ring carbon) as defined herein.

An "aldehyde" group refers to a carbonyl group, where R is hydrogen.

A "thiocarbonyl" group refers to a —C(=S)—R group, where R is as defined herein.

A "C-carboxy" group refers to a —C(=O)—O—R groups, where R is as defined herein.

An "O-carboxy" group refers to an RC(=O)—O— group, where R is as defined herein.

An "oxo" group refers to a =O group.

A "carboxylic acid" group refers to a C-carboxyl group in which R is hydrogen.

A "halo" group refers to fluorine, chlorine, bromine or iodine.

A "trihalomethyl" group refers to a —CX$_3$ group wherein X is a halo group as defined herein.

A "sulfinyl" group refers to an —S(=O)—R group, where R is as defined herein.

A "sulfonyl" group refers to an —S(=O)$_2$—R group, where R is as defined herein.

An "S-sulfonamido" group refers to a —S(=O)$_2$—NR$_2$ group, with each of R as is defined herein.

An "N-sulfonamido" group refers to an RS(=O)$_2$—NR group, where each of R is as defined herein.

An "O-carbamyl" group refers to an —OC(=O)—NR$_2$ group, where each of R is as defined herein.

An "N-carbamyl" group refers to an ROC(=O)—NR— group, where each of R is as defined herein.

An "O-thiocarbamyl" group refers to an —OC(=S)—NR$_2$ group, where each of R is as defined herein.

An "N-thiocarbamyl" group refers to an ROC(=S)NR— group, where each of R is as defined herein.

An "amino" group refers to an —NR$_2$ group where each of R is as defined herein.

A "C-amido" group refers to a —C(=O)—NR$_2$ group, where each of R is as defined herein.

An "N-amido" group refers to an RC(=O)—NR— group, where each of R is as defined herein.

An "urea" group refers to an —NRC(=O)—NR$_2$ group, where each of R is as defined herein.

A "guanidino" group refers to an —RNC(=N)—NR$_2$ group, where each of R is as defined herein.

A "guanyl" group refers to an R$_2$NC(=N)— group, where each of R is as defined herein.

The term "phosphonyl" or "phosphonate" describes a —P(=O)(OR)$_2$ group, with each of R as defined herein.

The term "phosphate" describes an —O—P(=O)(OR)$_2$ group, with each of R as defined herein.

A "phosphoric acid" is a phosphate group in which each of R is hydrogen.

The term "phosphinyl" describes a —PR$_2$ group, with each of R as defined herein.

The term "thiourea" describes a —NR—C(=S)—NR— group, each of R is as defined herein.

The term "saccharide" refers to one or more sugar unit, either an open-chain sugar unit or a cyclic sugar unit (e.g., pyranose- or furanose-based units), and encompasses any monosaccharide, disaccharide and oligosaccharide, unless otherwise indicated.

The term "salt" includes both internal salt or external salt. In some embodiments, the salt is an internal salt, i.e., a zwitterion structure. In some embodiments, the salt is an external salt. In some embodiments, the external salt is a pharmaceutically acceptable salt having a suitable counter ion. Suitable counterions for pharmaceutical use are known in the art.

The term "VB-201" refers to 1-hexadecyl-2-(4'-carboxy)butyl-glycero-3-phosphocholine. According to embodiments of the present invention, VB-201 may be a chiral enantiomer of 1-hexadecyl-2-(4'-carboxy)butyl-glycero-3-phosphocholine, i.e., either the (R)-enantiomer ((R)-1-hexadecyl-2-(4'-carboxy)butyl-sn-glycero-3-phosphocholine) or the (S)-enantiomer ((S)-1-hexadecyl-2-(4'-carboxy)butyl-sn-glycero-3-phosphocholine), or a mixture thereof (e.g., a racemate). According to exemplary embodiments, VB-201 is (R)-1-hexadecyl-2-(4'-carboxy)butyl-sn-glycero-3-phosphocholine. As understood by those skilled in the art, designating VB-201 as the (R)-enantiomer or the (S)-enantiomer does not require 100% enantiomeric purity, but instead refers to a substantially enriched single enantiomer either as an R or S isomer (e.g., having an enantiomeric excess of at least 80%, at least 85%, at least 90%, at least 95%, at least 98%, at least 99%, or higher). In some embodiments, VB-201 is (R)-1-hexadecyl-2-(4'-carboxy)butyl-sn-glycero-3-phosphocholine having at least 90% enantiomeric excess. The term OB201 refers to ovalbumin bound VB-201 as described in the Examples section.

The term "VB-221" refers to 1-(2'-octyl)dodecyl-2-(4'-carboxy)butyl-glycero-3-phosphocholine. According to embodiments of the present invention, VB-221 may be a chiral enantiomer of 1-(2'-octyl)dodecyl-2-(4'-carboxy)butyl-glycero-3-phosphocholine, i.e., either the (R)-enantiomer or the (S)-enantiomer, or any mixtures thereof (e.g., a racemate). According to exemplary embodiments, VB-221 is (I)-1-(2'-octyl)dodecyl-2-(4'-carboxy)butyl-sn-glycero-3-phosphocholine. Similarly, as understood by those skilled in the art, designating VB-221 as the (R)-enantiomer or the (S)-enantiomer does not require 100% enantiomeric purity, but instead refers to a substantially enriched single enantiomer either as an R or S isomer (e.g., having an enantiomeric excess of at least 80%, at least 85%, at least 90%, at least 95%, at least 98%, at least 99%, or higher). In some embodiments, VB-221 is (R)-1-1-(2'-octyl)dodecyl-2-(4'-carboxy)butyl-sn-glycero-3-phosphocholine having at least 90% enantiomeric excess. The term OB221 refers to ovalbumine bound VB-221 as described in the Examples section.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

MOSPD2 and Inhibitors of MOSPD2

The present application is based, in part, on the identification of a biological function for Motile Sperm Domain containing Protein 2 (MOSPD2) Inhibition of MOSPD2 has been found to inhibit migration of monocytes towards different chemokines and block activation of chemokine receptor signaling pathways. These results indicate that MOSPD2 is pivotal for leukocyte and monocyte migration and that blocking its activity inhibits inflammation and has therapeutic benefit in inflammatory diseases and disorders.

Some embodiments of the invention relate to an inhibitor of MOSPD2 or to methods and compositions comprising an inhibitor of MOSPD2. In some embodiments, the inhibitor is an isolated binding molecule that inhibits MOSPD2. In other embodiments, the inhibitor is a polypeptide, DNA, or RNA. In other embodiments, the inhibitor is a polypeptide that specifically binds to MOSPD2. In other embodiments, the inhibitor is an antibody or antigen binding fragment thereof that specifically binds to MOSPD2. In other embodiments, the inhibitor is an RNA silencing agent.

In other embodiments, an inhibitor of MOSPD2 is an antibody or antigen binding fragment thereof that specifically binds to a MOSPD2 polypeptide. In other embodiments, the antibody is a polyclonal, monoclonal, murine, human, humanized, chimeric, or single chain antibody. In other embodiments, the antigen binding fragment is a Fab, Fab', F(ab')$_2$, Fv, scFv, sdFv fragment, VH domain, or VL domain.

In some embodiments, the invention relates to an isolated antibody or antigen binding fragment thereof that specifically binds to MOSPD2. In some embodiments, an antibody or antigen binding fragment thereof described herein, which specifically binds to MOSPD2 (e.g., human MOSPD2), comprises a VH, a VL, or a VH and VL. In other embodiments, the antibody or antigen binding fragment thereof comprises a constant region.

In some embodiments, the VH, VL, or VH and VL comprise one or more complementarity determining regions (CDRs). In some embodiments, the VH comprises CDR1, CDR2, CDR3, or any combination thereof. In some embodiments, the VL comprises CDR1, CDR2, CDR3, or any combination thereof.

In some embodiments, the VH, VL, or VH and VL comprise one or more framework regions (FRs). In some embodiments, the VH comprises FR1, FR2, FR3, FR4, or any combination thereof. In some embodiments, the VL comprises FR1, FR2, FR3, FR4, or any combination thereof.

In a particular embodiment, an antibody or antigen binding fragment thereof described herein, which specifically binds to MOSPD2 (e.g., human MOSPD2), comprises a VH comprising CDR1, CDR2, and CDR3, and a VL comprising CDR1, CDR2, and CDR3.

In other embodiments, the antibodies or antigen binding fragments thereof comprise a constant region. In some embodiments, the constant region of the light chain comprises the amino acid sequence of a human kappa light chain constant region or a human lambda light chain constant region. In some embodiments, the constant region of the heavy chain comprises the amino acid sequence of a human gamma heavy chain constant region. Non-limiting examples of human constant region sequences have been described, e.g., see U.S. Pat. No. 5,693,780 and Kabat, E A et al., (1991). In some embodiments, the constant region amino acid sequence has been modified (e.g., one, two or more amino acid substitutions) such that it has at least 90%, at least 95%, at least 96%, at least 97%, at least 98%, or at least 99% sequence identity to a native human sequence.

In another aspect, provided herein are antibodies or antigen binding fragments thereof that recognize or bind to an epitope of MOSPD2 (e.g., an epitope of human MOSPD2). In another aspect, provided herein are antibodies or antigen binding fragments thereof that recognize or bind to the same epitope or an overlapping epitope of MOSPD2 (e.g., human MOSPD2) as an antibody described herein (e.g., an antibody described in Example 5 or 8). In another aspect, the antibodies or antigen binding fragments thereof recognize more than one epitope of MOSPD2 (e.g., two, three, four, five or six epitopes).

In certain embodiments, an epitope of MOSPD2 can be determined by one or more methods described in the literature, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization can be accomplished using methods described in the literature (e.g., Giegé R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303). Antibody: antigen crystals can be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323). Mutagenesis mapping studies can be accomplished using methods described in the literature. See, e.g., Champe M et al., (1995) szpra and Cunningham B C & Wells J A (1989) szpra for a description of mutagenesis techniques, including alanine scanning mutagenesis techniques. In a specific embodiment, an epitope of an antibody or antigen binding fragment thereof is determined using alanine scanning mutagenesis studies. Epitope characterization of an antibody can also be determined by the methods provided in Ravn et al., Journal of Biological Chemistry 288: 19760-19772 (2013).

In addition, antibodies or antigen binding fragments thereof that recognize or bind to the same or overlapping epitopes of MOSPD2 (e.g., human MOSPD2) can be identified using routine techniques such as an immunoassay, for example, by showing the ability of one antibody to block the binding of another antibody to a target antigen, i.e., a competitive binding assay. Competitive binding can be determined in an assay in which the immunoglobulin under test inhibits specific binding of a reference antibody to a common antigen, such as MOSPD2. Numerous types of competitive binding assays have been described, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (Cheung R C et al., (1990) Virology 176: 546-52); and direct labeled RIA (Moldenhauer G et al., (1990) Scand J Immunol 32: 77-82). Typically, such an assay involves the use of purified antigen (e.g., MOSPD2 such as human MOSPD2) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors szpra, pp. 386-389.

In one embodiment, a competition assay is performed using surface plasmon resonance (BIAcore®), e.g., by an "in tandem approach" such as that described by Abdiche Y N et al., (2009) Analytical Biochem 386: 172-180, whereby MOSPD2 antigen is immobilized on the chip surface, for example, a CMS sensor chip and the anti-MOSPD2 antibodies are then run over the chip. To determine if an antibody or antigen binding fragment thereof competes with an anti-MOSPD2 antibody or antigen binding fragment thereof described herein, the anti-MOSPD2 antibody or antigen binding fragment thereof is first run over the chip surface to achieve saturation and then the potential, competing antibody is added. Binding of the competing antibody can then be determined and quantified relative to a non-competing control.

In certain aspects, competition binding assays can be used to determine whether an antibody or antigen binding fragment thereof is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody or antigen binding fragment thereof can be tested in competition binding assays with an antibody described herein (e.g., those in Example 5 or 8), or a chimeric or Fab antibody thereof, or an antibody comprising VH CDRs and VL CDRs of an antibody described herein (e.g., those in Example 5 or 8).

Accordingly, in a certain aspect, provided herein are antibodies or antigen binding fragments thereof that compete (e.g., in a dose dependent manner) for binding to MOSPD2 (e.g., human MOSPD2) with an antibody described herein (e.g., Example 5 or 8), as determined using assays known to one of skill in the art or described herein (e.g., ELISA competitive assays, surface plasmon resonance or Scatchard analysis).

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): 508-517, 501-514, 233-241, 509-517, 212-221, 13-24, 505-517, 505-514, 89-100, 506-517, 233-245, 504-514, 128-136, 218-226, 15-24, 83-96, 42-50, 462-474, 340-351, 504-517, 462-470, 327-337, 21-32, 217-226, 510-517, 178-190, 497-509, 504-516, 64-77, 504-515, 147-159, 503-315, 88-97, 208-218, 178-191, 502-515, 503-516, 497-505, 500-509, 189-202, 189-197, 505-516, 1-63, 82-239, 93-234, 327-445, 327-431, and 497-517.

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): about 508 to about 517, about 501 to about 514, about 233 to about 241, about 509 to about 517, about 212 to about 221, about 13 to about 24, about 505 to about 517, about 505 to about 514, about 89 to about 100, about 506 to about 517, about 233 to about 245, about 504 to about 514, about 128 to about 136, about 218 to about 226, about 15 to about 24, about 83 to about 96, about 42 to about 50, about 462 to about 474, about 340 to about 351, about 504 to about 517, about 462 to about 470, about 327 to about 337, about 21 to about 32, about 217 to about 226, about 510 to about 517, about 178 to about 190, about 497 to about 509, about 504 to about 516, about 64 to about 77, about 504 to about 515, about 147 to about 159, about 503 to about 515, about 88 to about 97, about 208 to about 218, about 178 to about 191, about 502 to about 515, about 503 to about 516, about 497 to about 505, about 500 to about 509, about 189 to about 202, about 189 to about 197, about 505 to about 516, about 1 to about 63, about 82 to about 239, about 93 to about 234, about 327 to about 445, about 327 to about 431, and about 497 to about 517.

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): about 505 to about 515, about 500 to about 515, about 230 to about 240, about 510 to about 520, about 210 to about 220, about 15 to about 25, about 505 to about 520, about 505 to about 515, about 90 to about 100, about 505 to about 525, about 230 to about 245, about 505 to about 510, about 130 to about 140, about 220 to about 230, about 15 to about 30, about 80 to about 95, about 40 to about 50, about 460 to about 475, about 340 to about 350, about 500 to about 515, about 460 to about 470, about 325 to about 335, about 20 to about 35, about 215 to about 225, about 510 to about 520, about 175 to about 190, about 500 to about 510, about 505 to about 530, about 60 to about 75, about 500 to about 520, about 145 to about 160, about 502 to about 515, about 85 to about 100, about 205 to about 220, about 175 to about 190, about 500 to about 505, about 500 to about 525, about 495 to about 505, about 495 to about 510, about 190 to about 200, about 190 to about 198, about 502 to about 515, about 1 to about 60, about 80 to about 240, about 90 to about 235, about 330 to about 445, about 330 to about 430, and about 495 to about 515.

In some embodiments, antibodies or antigen binding fragments of the invention bind to MOSPD2 with an antibody-antigen equilibrium dissociation constant ($K_D$) of from about $10^{-6}$ M to about $10^{-12}$ M, or any range of values thereof (e.g., from about $10^{-7}$ M to about $10^{-12}$, from $10^{-8}$ M to about $10^{-12}$ M, from about $10^{-7}$ M to about $10^{-12}$ M, from about $10^{-10}$ M to about $10^{-12}$ M, from about $10^{-11}$ M to about $10^{-12}$ M, from about $10^{-6}$ M to about $10^{-11}$ M, from about $10^{-7}$ M to about $10^{-11}$ M, from about $10^{-8}$ M to about $10^{-11}$ M, from about $10^{-7}$ M to about $10^{-11}$ M, from about $10^{-10}$ M to about $10^{-11}$ M, from about $10^{-7}$ M to about $10^{-10}$ M, from about $10^{-7}$ M to about $10^{-10}$ M, from about $10^{-8}$ M to about $10^{-10}$ M, from about $10^{-7}$ M to about $10^{-10}$ M, from about $10^{-7}$ M to about $10^{-7}$ M, from about $10^{-7}$ M to about $10^{-7}$ M, from about $10^{-8}$ M to about $10^{-7}$ M, from about $10^{-7}$ M to about $10^{-8}$ M, or from about $10^{-7}$ M to about $10^{-8}$). In other embodiments, the antibody or antigen binding fragment thereof has a $K_D$ of about $10^{-7}$ M, about $10^{-7}$ M, about $10^{-8}$ M, about $10^{-7}$ M, about $10^{-10}$ M, about $10^{-11}$ M, or about $10^{-12}$ M. In some embodiments, the antibody or antigen binding fragment binds to one or more epitopes on MOSPD2. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with an antibody-antigen $K_{on}$ constant of from about $10^3$ 1/Ms to about $10^6$ 1/Ms, or any range of values thereof (e.g., from about $10^4$ 1/Ms to about $10^6$ 1/Ms, or from $10^5$ 1/Ms to about $10^6$ 1/Ms). In other embodiments, the antibody or antigen binding fragment thereof has a $K_{on}$ of about $10^3$ 1/Ms, about $10^4$ 1/Ms, about $10^5$ 1/Ms, or about $10^6$ 1/Ms.

In some embodiments, antibodies or antigen binding fragments of the invention bind to MOSPD2 with an antibody-antigen $K_{off}$ constant of from about $10^{-3}$ 1/s to about $10^{-6}$ 1/s, or any range of values thereof (e.g., from about $10^{-4}$ 1/s to about 10' 1/s, or from $10^{-5}$ 1/s to about 10' 1/s). In other embodiments, the antibody or antigen binding fragment thereof has a $K_{off}$ of about $10^{-3}$ 1/s, about $10^{-4}$ 1/s, about $10^{-5}$ 1/s, or about $10^{-6}$ 1/s.

In some embodiments, the antibody is an IgG, IgM, IgE, IgA or IgD molecule, or is derived therefrom. In other embodiments, the antibody comprises an Fc region.

In some embodiments, the invention relates to a pharmaceutical composition comprising an antibody or antigen binding fragment described herein, and a pharmaceutically acceptable carrier. In other embodiments, the invention relates to a method of treating, preventing, or reducing the incidence of a disease or disorder described herein, comprising administering to a subject in need thereof a therapeutically effective amount of an antibody or antigen binding fragment thereof described herein or a pharmaceutical composition described herein.

In additional embodiments of the invention, inhibition of MOSPD2 and downregulation of MOSPD2 activity can be effected on the genomic and/or the transcription level using a variety of molecules which interfere with transcription and/or translation [e.g., RNA silencing agents (e.g., antisense, siRNA, shRNA, micro-RNA), Ribozyme and DNAzyme], or on the protein level using e.g., antagonists, enzymes that cleave the polypeptide, small molecules that interfere with the protein's activity (e.g., competitive ligands) and the like.

Following is an exemplary list of agents capable of downregulating expression level and/or activity of a target such as MOSPD2.

Inhibition of MOSPD2 can occur, for example, by ectopic overexpression of MOSPD2 by infection, and it is intended that an inhibitor of MOSPD2 or a MOSPD2 inhibitor encompasses this type of inhibition.

Downregulation of MOSPD2 can also be achieved by gene editing. Gene editing can be performed, for example, with a clustered regularly interspaced short palindromic repeats CRISPR-CAS9 system. CRISPR-CAS9 systems have been described in the literature and can include, for example, CAS9 and a guide RNA. Other gene editing techniques have also been described in the literature and can also be used.

Downregulation of MOSPD2 can also be achieved by RNA silencing. As used herein, the phrase "RNA silencing" refers to a group of regulatory mechanisms [e.g., RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In some embodiments, the RNA silencing agent is capable of preventing complete processing (e.g., the full translation and/or expression) of an mRNA molecule through a post-transcriptional silencing mechanism. RNA silencing agents include non-coding RNA molecules, for example, RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

Some embodiments of the invention contemplate use of dsRNA to downregulate protein expression from mRNA.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

The strands of a double-stranded interfering RNA (e.g., an siRNA) may be connected to form a hairpin or stem-loop structure (e.g., an shRNA or sh-RNA). Thus, as mentioned, the RNA silencing agent of some embodiments of the invention may also be a short hairpin RNA (shRNA).

The terms "shRNA" or "sh-RNA", as used herein, refer to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell.

According to another embodiment, the RNA silencing agent may be a miRNA or a mimic thereof.

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA can also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA can be the first 13-33 nucleotides of the pre-miRNA. The sequence of the miRNA can also be the last 13-33 nucleotides of the pre-miRNA.

Another agent capable of downregulating a target is a DNAzyme molecule capable of specifically cleaving an mRNA transcript or DNA sequence of the target. DNAzymes are single-stranded polynucleotides which are capable of cleaving both single and double stranded target sequences. (Breaker et al., Chemistry and Biology 1995; 2:655; Santoro et al., Proc. Natl. Acad. Sci. USA 1997; 943:4262.) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions. (Santoro et al.; Khachigian, Curr. Cpin. Mol. Ther. 2002; 4:119-121.)

Downregulation of a target can also be effected by using an antisense polynucleotide capable of specifically hybridizing with an mRNA transcript encoding the target.

Another agent capable of downregulating a target is a ribozyme molecule capable of specifically cleaving an mRNA transcript encoding a target. Ribozymes are being increasingly used for the sequence-specific inhibition of gene expression by the cleavage of mRNAs encoding proteins of interest. (Welch et al., Curr. Cpin. Biotechnol. 1998; 9:486-96.)

Another agent capable of downregulating a target is any molecule which binds to and/or cleaves the target. Such molecules can be antagonists of the target, or inhibitory peptides of the target.

It will be appreciated that a non-functional analogue of at least a catalytic or binding portion of a target can be also used as an agent which downregulates the target.

Another agent which can be used along with some embodiments of the invention to downregulate a target is a molecule which prevents target activation or substrate binding.

In some embodiments, an inhibitor of a given protein target inhibits the protein by binding to the protein, by binding to a compound which binds to the protein (e.g., a substrate, a regulatory protein), and/or by binding to an oligonucleotide (e.g., mRNA) encoding the protein.

In some embodiments, the inhibitor of MOSPD2 is a small molecule (e.g., characterized by a molecular weight of less than 800 Da). In some embodiments, the small molecule MOSPD2 inhibitor is a tocopherol or a derivative thereof (e.g., alpha-tocopherol, beta-tocopherol, gamma-tocopherol, delta-tocopherol), a triterpene (e.g., squalene), a vitamin A or a derivative thereof (e.g., retinaldehyde), a phosphatidylglyceride (e.g., phosphatidylinositol), or a phospholipid (e.g., phosphatidylcholine, an oxidized phospholipid).

In some embodiments, the small molecule MOSPD2 inhibitor is an oxidized phospholipid having a structure according to Formula I:

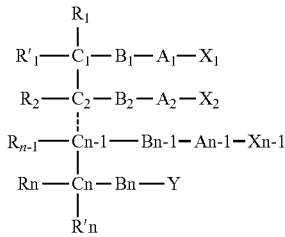

Formula I or a pharmaceutically acceptable salt, a hydrate or a solvate thereof, wherein:

n is an integer from 1 to 6, wherein when n is 1, Cn, Bn, Rn, and Y are absent, and Ci is attached to R'n;

each of $B_1, B_2, \ldots Bn-1$ and Bn is independently selected from the group consisting of oxygen, sulfur, nitrogen, phosphorus and silicon, whereby each of said nitrogen, phosphorus and silicon is optionally substituted by one substituent selected from the group consisting of alkyl, halo, cycloalkyl, aryl, hydroxy, thiohydroxy, alkoxy, aryloxy, thioaryloxy, thioalkoxy and oxo;

each of $A_1, A_2, \ldots An-1$ and An is independently selected from the group consisting of CR"R'", C=O and C=S, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-biphosphonate, phosphoinositol-4,5-bisphosphate, pyrophosphate, phosphoethanolamine-diethylenetriamine-pentaacetate, dinitrophenyl-phosphoethanolamine, phosphoglycerol and a moiety having the general formula:

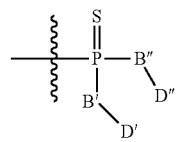

wherein:

each of B' and B" is independently selected from the group consisting of sulfur and oxygen; and each of D' and D" is independently selected from the group consisting of hydrogen, alkyl, amino substituted alkyl, cycloalkyl, phosphonate and thiophosphonate; and each of $X_1, X_2, \ldots Xn-1$ is independently a saturated or unsaturated hydrocarbon having the general Formula II:

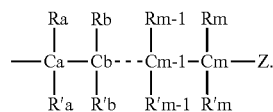

Formula II wherein m is an integer from 1 to 26; and
Z is selected from the group consisting of:
H,

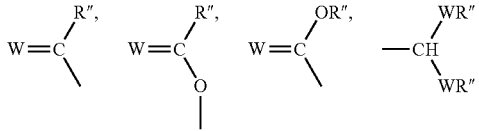

and —OR", wherein W is selected from the group consisting of oxygen and sulfur;

wherein at least one of $X_1, X_2, \ldots Xn-1$ comprises a Z other than hydrogen, and wherein:

each of $R_1, R'_1, R_2, \ldots Rn-1, Rn, R'n$, each of R" and R'" and each of Ra, R'a, Rb, R'b, \ldots Rm-1, R'm-1, Rm and R'm is independently selected from the group consisting of a bond, hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1, R'_1, R_2, \ldots Rn-1, Rn$ and R'n and/or at least two of Ra, R'a, Rb, R'b, \ldots Rm-1, R'm-1, Rm and R'm form at least one four-, five- or six-membered aromatic, heteroaromatic, alicyclic or heteroalicyclic ring, or a pharmaceutically acceptable salt, a hydrate or a solvate thereof. In any of the embodiments described herein, the oxidized phospholipid can exist as a stereoisomeric mixture of any ratio, for example, as a substantially enriched single enantiomer such as an R or S isomer (e.g., having an enantiomeric excess of at least 80%, at least 85%, at least 90%, at least 95%, at least 98%, at least 99%, or higher), or as a mixture of two enantiomers (e.g., a racemic mixture); and/or as a substantially enriched single diastereomer (e.g., having an diastereomeric excess of at least 80%, at least 85%, at least 90%, at least 95%, at least 98%, at least 99%, or higher), or as a mixture of two or more diastereomers.

In one embodiment, the oxidized phospholipid useful in any of the methods of the present disclosure has a structure according to Formula III:

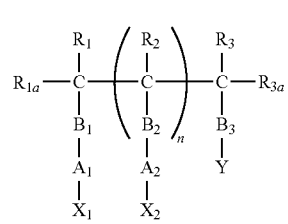

Formula III or a pharmaceutically acceptable salt, hydrate or solvate thereof.

In Formula III, n is an integer selected from 1 to 4.

In Formula III, $B_1$, each $B_2$, and $B_3$ are independently selected from the group consisting of oxygen, sulfur, and $NR_4$, wherein $R_4$ is selected from hydrogen, alkyl, cycloalkyl, aryl, and acyl.

In Formula III, $A_1$ and each $A_2$ are independently selected from the group consisting of $CR_eR_{ee}$, $CR_e=CR_{ee}$, C=O and C=S, wherein $R_e$ and $R_{ee}$ are independently selected from hydrogen, alkyl, alkenyl, alkynyl, cycloalkyl, aryl, and heteroaryl.

In Formula III, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol, and a moiety having the general formula:

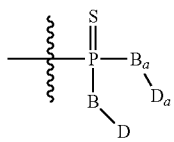

wherein:

each of B and Ba is independently selected from the group consisting of sulfur and oxygen; and D and Da are independently selected from the group consisting of hydrogen, alkyl, aminoalkyl, cycloalkyl, phosphonate and thiophosphonate.

In Formula III, $X_1$ and each $X_2$ are independently a saturated or unsaturated, linear or branched hydrocarbon, wherein at least one of $X_1$ and $X_2$ is substituted with an oxidized moiety Z selected from the group consisting of:

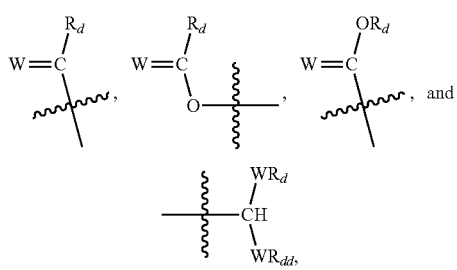

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula III, $X_1$ and each $X_2$ independently have the general Formula IV:

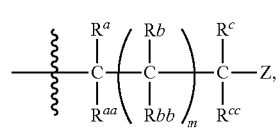

Formula IV

In Formula IV, m is an integer selected from 1 to 26.
In Formula IV, Z is selected from the group consisting of: H,

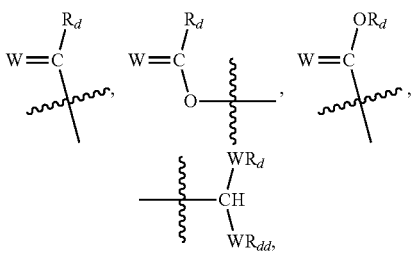

and OH, wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In Formula III and Formula IV, $R_1$, $R_{1a}$, each $R_2$, $R_3$, $R_{3a}$, $R_a$, $R_{aa}$, each $R_b$, each $R_{bb}$, $R_e$ and $R_{ee}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In one embodiment in Formula III, n is 1 or 2. In another embodiment in Formula III, n is 1.

In one embodiment in Formula III, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In another embodiment in Formula III, Y is selected from the group consisting of hydrogen, phosphoryl choline, and phosphoryl ethanolamine.

In another embodiment in Formula III, Y is selected from the group consisting of phosphoryl choline, and phosphoryl ethanolamine.

In one embodiment in Formula III, Y is phosphoryl choline.

In one embodiment in Formula III, Z is

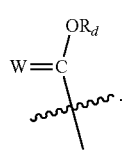

In another embodiment in Formula III, Z is a carboxylic acid group.

In a further embodiment in Formula III, n is 1 and Y is phosphoryl choline.

In a further embodiment in Formula III, each of $B_1$, $B_2$, and $B_3$ is oxygen.

In a further embodiment in Formula III, n is 1, Y is phosphoryl choline, and each of $B_1$, $B_2$, and $B_3$ is oxygen.

In one embodiment, the oxidized phospholipid useful in any of the methods of the present disclosure has a structure according to Formula IIIa:

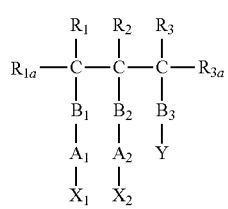

Formula IIIa or a pharmaceutically acceptable salt, hydrate or solvate thereof.

In Formula IIIa, $B_1$, $B_2$, and $B_3$ are independently selected from oxygen and sulfur.

In Formula IIIa, $A_1$ and $A_2$ are independently selected from the group consisting of $CH_2$, $CH=CH$, $C=O$ and $C=S$.

In Formula IIIa, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In Formula IIIa, $R_1$, $R_{1a}$, $R_2$, $R_3$, and $R_{3a}$ are independently selected from the group consisting of hydrogen, alkyl, alken, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five-or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five-or six-membered aromatic, heteroaromatic, alicyclic or heteroalicyclic ring.

In Formula IIIa, $X_1$ and $X_2$ are independently a saturated or unsaturated, linear or branched hydrocarbon, wherein at least one of $X_1$ and $X_2$ is substituted with an oxidized moiety Z having a formula selected from:

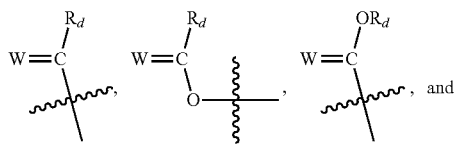, and

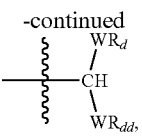

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula IIIa, $X_1$ and $X_2$ independently have a structure according to Formula IVa:

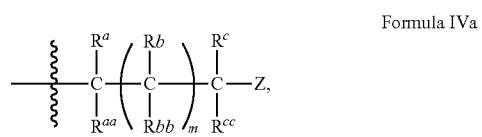

Formula IVa

In Formula IVa, m is an integer selected from 1 to 26.

In Formula IVa, $R_a$, $R_{aa}$, each $R_b$, each $R_{bb}$, $R_c$, and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In Formula IVa, Z is selected from the group consisting of:
H,

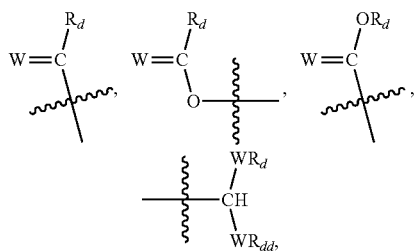

and $OR_d$,
wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In one embodiment in Formula IIIa, Z is

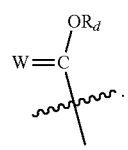

In another embodiment in Formula IIIa, Z is a carboxylic acid group.

In one embodiment in Formula IIIa, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, phosphoethanolamine-diethylenetriamine-pentaacetate, dinitrophenyl-phosphoethanolamine, and phosphoglycerol.

In one embodiment in Formula IIIa, Y is selected from the group consisting of hydrogen, phosphoryl choline, and phosphoryl ethanolamine.

In another embodiment in Formula IIIa, Y is selected from the group consisting of phosphoryl choline, and phosphoryl ethanolamine.

In one embodiment in Formula IIIa, Y is phosphoryl choline.

In a further embodiment in Formula IIIa, each of $B_1$, $B_2$, and $B_3$ is oxygen.

In a further embodiment in Formula IIIa, Y is phosphoryl choline, and each of $B_1$, $B_2$, and $B_3$ is oxygen.

In one embodiment in Formula IIIa, the oxidized phospholipid has a structure according to Formula V:

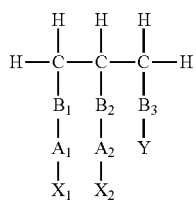

Formula V wherein $B_1$, $B_2$, $B_3$, $A_1$, $A_2$, $X_1$, $X_2$, and Y are defined as for Formula IIIa.

In one embodiment, each of $B_1$, $B_2$, $B_3$ in Formula V is oxygen and the oxidized phospholipid has a structure according to the Formula VI:

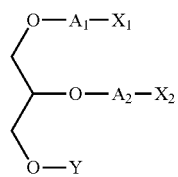

Formula VI

In Formula VI, $A_1$ is selected from the group consisting of $CH_2$, CH=CH and C=O. In one example, $A_1$ in Formula VI is $CH_2$.

In Formula VI, $A_2$ is absent or $CH_2$.

In Formula VI, $X_1$ is an alkyl having from 1 to 30 carbon atoms.

In Formula VI, $X_2$ is

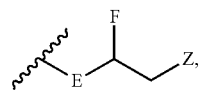

wherein
E is absent or is an alkyl chain having from 1 to 24 carbon atoms;
F is selected from the group consisting of hydrogen, hydroxy, alkyl, alkoxy, halide, acetoxy and aryl; and
Z is selected from the group consisting of:

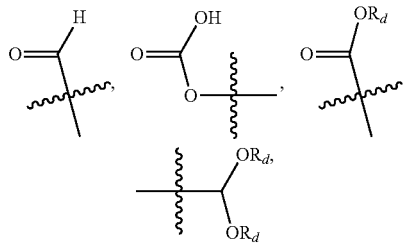

and $-OR_d$,
wherein $R_d$ is selected from H, alkyl and aryl.

In Formula VI, Y is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol.

In one embodiment in Formula VI, $X_1$ is alkyl having from 10 to 30 carbon atoms, or from 8 to 30 carbon atoms.

In one embodiment in Formula VI, E is alkyl having from 1 to 10 carbon atoms, or from 1 to 4 carbon atoms.

In one embodiment in Formula VI, Y is phosphoryl choline.

Each carbon atom in Formula I, II, III, IIIa, V, and VI is a chiral or non-chiral carbon atom, wherein each chiral carbon atom can have an S-configuration or R-configuration.

In one preferred embodiment, the oxidized phospholipid is 1-hexadecyl-2-(4'-carboxy)butyl-glycero-3-phosphocholine. In another preferred embodiment, the oxidized phospholipid is (R)-1-hexadecyl-2-(4'-carboxy)butyl-sn-glycero-3-phosphocholine.

In one preferred embodiment, the oxidized phospholipid is

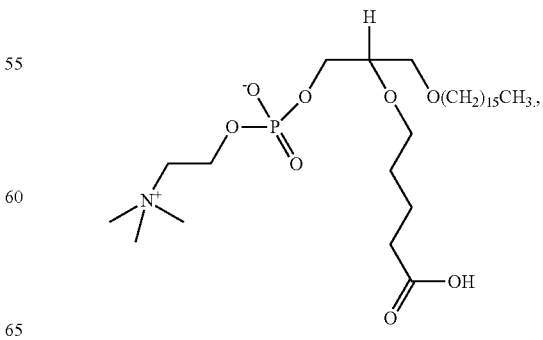

or a pharmaceutically acceptable salt thereof.

In one preferred embodiment, the oxidized phospholipid is

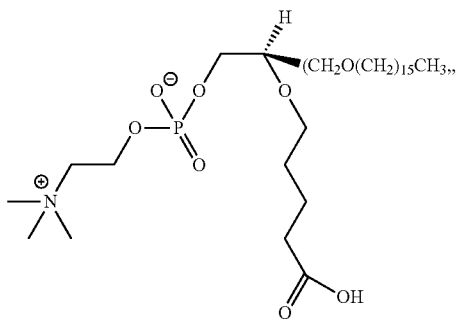

or a pharmaceutically acceptable salt thereof.

The small molecule MOSPD2 inhibitor described herein can be used alone, as a single agent, in any of the methods described herein or it can be used in combination with another agent (e.g., another MOSPD2 inhibitor). In any of the embodiments described herein, useful small molecule MOSPD2 inhibitors include those that are more potent inhibitors of MOSPD2 (e.g., human MOSPD2 on the cell surface of a monocyte) when compared to VB-221, e.g., those having a lower $IC_{50}$ value compared to that of VB-221. More preferably, useful small molecule MOSPD2 inhibitors include those that are equal or more potent inhibitors of MOSPD2 (e.g., human MOSPD2 on the cell surface of a monocyte) when compared to VB-201, e.g., those having a lower $IC_{50}$ value compared to that of VB-201. As understood by those skilled in the art, an $IC_{50}$ value indicates how much of a particular drug or other substance (inhibitor) is needed to inhibit a given biological process (or component of a process, i.e. an enzyme, cell, cell receptor or microorganism) by half. Methods for determining $IC_{50}$ values are known in the art.

When a small molecule MOSPD2 inhibitor (as described herein) in a pharmaceutical composition is administered to a subject alone as a single agent or in combination with another agent, the small molecule MOSPD2 inhibitor (e.g., VB-201) is present in an amount such that the administration causes at least 10% (e.g., at least 20%, at least 30%, at least 40%, at least 50%, at least 60%, at least 70%, at least 80%, at least 90%, at least 95%, at least 99%, or higher) inhibition of one or more activities of MOSPD2 (e.g., human MOSPD2) (e.g., MOSPD2 expression, inflammatory cell migration (e.g., leukocyte or monocyte migration), chemotaxis (e.g., leukocyte or monocyte chemotaxis), a chemokine signaling pathway, EGF receptor phosphorylation, ERK phosphorylation, AKT phosphorylation. In some embodiments, administration of the small molecule MOSPD2 inhibitor to a human subject causes at least 10% (e.g., at least 20%, at least 30%, at least 40%, at least 50%, at least 60%, at least 70%, at least 80%, at least 90%, at least 95%, at least 99%, or higher) inhibition of one or more activities of a human MOSPD2. In one aspect, administration of the small molecule MOSPD2 inhibitor causes from about 10% to 100%, from about 10% to about 99%, from about 10% to about 95%, from about 10% to about 90%, from about 10% to about 85%, from about 10% to about 80%, from about 10% to about 70%, from about 20% to about 99%, from about 20% to about 95%, from about 20% to about 90%, from about 20% to about 85%, from about 20% to about 80%, from about 30% to about 95%, from about 30% to about 90%, from about 30% to about 85%, from about 30% to about 80%, from about 40% to about 95%, from about 40% to about 90%, from about 40% to about 85%, from about 40% to about 80%, from about 50% to about 95%, from about 50% to about 90%, from about 50% to about 85%, from about 50% to about 80%, from about 60% to about 95%, from about 60% to about 90%, from about 60% to about 85%, or from about 60% to about 80% inhibition of one or more activities of MOSPD2, e.g., regulation of inflammatory cell migration, chemokine signaling pathways, growth factor signaling pathways, EGF receptor phosphorylation, ERK phosphorylation, AKT phosphorylation, and/or FAK phosphorylation. Preferably, the small molecule MOSPD2 inhibitor is VB-201.

In some embodiments, an inhibitor of a given protein inhibits the protein by binding to the protein and/or to an oligonucleotide (e.g., mRNA) encoding the protein.

In other embodiments, the MOSPD2 inhibitor is (i) an isolated binding molecule that specifically binds to a MOSPD2 polypeptide, (ii) an isolated binding molecule that specifically binds to a ligand of a MOSPD2 polypeptide, (iii) an antisera raised against a MOSPD2 polypeptide, (iv) a soluble MOSPD2 polypeptide, or (v) a soluble MOSPD2 polypeptide comprising, consisting essentially of, or consisting of an extracellular domain of a MOSPD2 polypeptide.

In still other embodiments, the inhibitor is an antibody that specifically binds to a MOSPD2 polypeptide. In other embodiments, the inhibitor is an antigen binding fragment of an antibody that specifically binds to a MOSPD2 polypeptide. In other embodiments, the antibody is a polyclonal, monoclonal, murine, human, humanized, chimeric, or single chain antibody. In other embodiments, the antigen binding fragment is a Fab, Fab', F(ab')$_2$, Fv, scFv, sdFv fragment, VH domain, or VL domain.

In some embodiments, the inhibitor is an antibody or antigen binding fragment thereof described herein, which specifically binds to MOSPD2 (e.g., human MOSPD2), comprises a VH, a VL, or a VH and VL. In other embodiments, the antibody or antigen binding fragment thereof comprises a constant region.

In some embodiments, the VH, VL, or VH and VL comprise one or more complementarity determining regions (CDRs). In some embodiments, the VH comprises CDR1, CDR2, CDR3, or any combination thereof. In some embodiments, the VL comprises CDR1, CDR2, CDR3, or any combination thereof.

In some embodiments, the VH, VL, or VH and VL comprise one or more framework regions (FRs). In some embodiments, the VH comprises FR1, FR2, FR3, FR4, or any combination thereof. In some embodiments, the VL comprises FR1, FR2, FR3, FR4, or any combination thereof.

In a particular embodiment, the antibody or antigen binding fragment thereof described herein, which specifically binds to MOSPD2 (e.g., human MOSPD2), comprises a VH comprising CDR1, CDR2, and CDR3, and a VL comprising CDR1, CDR2, and CDR3.

In other embodiments, the antibodies or antigen binding fragments thereof comprise a constant region. In some embodiments, the constant region of the light chain comprises the amino acid sequence of a human kappa light chain constant region or a human lambda light chain constant region. In some embodiments, the constant region of the heavy chain comprises the amino acid sequence of a human gamma heavy chain constant region. Non-limiting examples of human constant region sequences have been described, e.g., see U.S. Pat. No. 5,693,780 and Kabat, E A et al., (1991). In some embodiments, the constant region amino acid sequence has been modified (e.g., one, two or more amino acid substitutions) such that it has at least 90%, at least 95%, at least 96%, at least 97%, at least 98%, or at least 99% sequence identity to a native human sequence. In another aspect, provided herein are antibodies or antigen binding fragments thereof that recognize or bind to an epitope of MOSPD2 (e.g., an epitope of human MOSPD2). In another aspect, provided herein are antibodies or antigen binding fragments thereof that recognize or bind to the same epitope or an overlapping epitope of MOSPD2 (e.g., human MOSPD2) as an antibody described herein (e.g., an antibody described in Example 1 or 8). In another aspect, the antibodies or antigen binding fragments thereof recognize more than one epitope of MOSPD2 (e.g., two, three, four, five or six epitopes).

In certain embodiments, an epitope of MOSPD2 can be determined by one or more methods described in the literature, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization can be accomplished using methods described in the literature (e.g., Giegé R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303). Antibody: antigen crystals can be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al., U.S. Patent Application No. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323). Mutagenesis mapping studies can be accomplished using methods described in the literature. See, e.g., Champe M et al., (1995) sipra and Cunningham B C & Wells J A (1989) sipra for a description of mutagenesis techniques, including alanine scanning mutagenesis techniques. In a specific embodiment, an epitope of an antibody or antigen binding fragment thereof is determined using alanine scanning mutagenesis studies. Epitope characterization of an antibody can also be determined by the methods provided in Ravn et al., Journal of Biological Chemistry 288: 19760-19772 (2013).

In addition, antibodies or antigen binding fragments thereof that recognize or bind to the same or overlapping epitopes of MOSPD2 (e.g., human MOSPD2) can be identified using routine techniques such as an immunoassay, for example, by showing the ability of one antibody to block the binding of another antibody to a target antigen, i.e., a competitive binding assay. Competitive binding can be determined in an assay in which the immunoglobulin under test inhibits specific binding of a reference antibody to a common antigen, such as MOSPD2. Numerous types of competitive binding assays have been described, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (Cheung R C et al., (1990) Virology 176: 546-52); and direct labeled RIA (Moldenhauer G et al., (1990) Scand J Immunol 32: 77-82). Typically, such an assay involves the use of purified antigen (e.g., MOSPD2 such as human MOSPD2) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors szpra, pp. 386-389.

In one embodiment, a competition assay is performed using surface plasmon resonance (BIAcore®), e.g., by an "in tandem approach" such as that described by Abdiche Y N et al., (2009) Analytical Biochem 386: 172-180, whereby MOSPD2 antigen is immobilized on the chip surface, for example, a CMS sensor chip and the anti-MOSPD2 antibodies are then run over the chip. To determine if an antibody or antigen binding fragment thereof competes with an anti-MOSPD2 antibody or antigen binding fragment thereof described herein, the anti-MOSPD2 antibody or antigen binding fragment thereof is first run over the chip surface to achieve saturation and then the potential, competing antibody is added. Binding of the competing antibody can then be determined and quantified relative to a non-competing control.

In certain aspects, competition binding assays can be used to determine whether an antibody or antigen binding fragment thereof is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody or antigen binding fragment thereof can be tested in competition binding assays with an antibody described herein (e.g., those in the examples), or a chimeric or Fab antibody thereof, or an antibody comprising VH CDRs and VL CDRs of an antibody described herein (e.g., those in the examples).

Accordingly, in a certain aspect, provided herein are antibodies or antigen binding fragments thereof that compete (e.g., in a dose dependent manner) for binding to MOSPD2 (e.g., human MOSPD2) with an antibody described herein (e.g., those in the examples), as determined using assays known to one of skill in the art or described herein (e.g., ELISA competitive assays, surface plasmon resonance or Scatchard analysis).

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): 508-517, 501-514, 233-241, 509-517, 212-221, 13-24, 505-517, 505-514, 89-100, 506-517, 233-245, 504-514, 128-136, 218-226, 15-24, 83-96, 42-50, 462-474, 340-351, 504-517, 462-470, 327-337, 21-32, 217-226, 510-517, 178-190, 497-509, 504-516, 64-77, 504-515, 147-159, 503-315, 88-97, 208-218, 178-191, 502-515, 503-516, 497-505, 500-509, 189-202, 189-197, 505-516, 1-63, 82-239, 93-234, 327-445, 327-431, and 497-517.

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): about 508 to about 517, about 501 to about 514, about 233 to about 241, about 509 to about 517, about 212 to about 221, about 13 to about 24, about 505 to about 517, about 505 to about 514, about 89 to about 100, about 506 to about 517, about 233 to about 245, about 504 to about 514, about 128 to about 136, about 218 to about 226, about 15 to about 24, about 83 to about 96, about 42 to about 50, about 462 to about 474, about 340 to about 351, about 504 to about 517, about 462 to about 470, about 327 to about 337, about 21 to about 32, about 217 to about 226, about 510 to about 517, about 178 to about 190, about 497 to about 509, about 504 to about 516, about 64 to about 77, about 504 to about 515, about 147 to about 159, about 503 to about 515, about 88 to about 97, about 208 to about 218, about 178 to about 191, about 502 to about 515, about 503 to about 516, about 497 to about 505, about 500 to about 509, about 189 to about 202, about 189 to about 197, about 505 to about 516, about 1 to about 63, about 82 to about 239, about 93 to about 234, about 327 to about 445, about 327 to about 431, and about 497 to about 517.

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): about 505 to about 515, about 500 to about 515, about 230 to about 240, about 510 to about 520, about 210 to about 220, about 15 to about 25, about 505 to about 520, about 505 to about 515, about 90 to about 100, about 505 to about 525, about 230 to about 245, about 505 to about 510, about 130 to about 140, about 220 to about 230, about 15 to about 30, about 80 to about 95, about 40 to about 50, about 460 to about 475, about 340 to about 350, about 500 to about 515, about 460 to about 470, about 325 to about 335, about 20 to about 35, about 215 to about 225, about 510 to about 520, about 175 to about 190, about 500 to about 510, about 505 to about 530, about 60 to about 75, about 500 to about 520, about 145 to about 160, about 502 to about 515, about 85 to about 100, about 205 to about 220, about 175 to about 190, about 500 to about 505, about 500 to about 525, about 495 to about 505, about 495 to about 510, about 190 to about 200, about 190 to about 198, about 502 to about 515, about 1 to about 60, about 80 to about 240, about 90 to about 235, about 330 to about 445, about 330 to about 430, and about 495 to about 515.

In some embodiments, antibodies or antigen binding fragments of the invention bind to MOSPD2 with an antibody-antigen equilibrium dissociation constant ($K_D$) of from about $10^{-7}$ M to about $10^{-12}$ M, or any range of values thereof (e.g., from about $10^{-7}$ M to about $10^{-12}$, from $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-6}$ M to about $10^{-11}$ M, from about $10^{-7}$ M to about $10^{-11}$ M, from about $10^{-8}$ M to about $10^{-11}$ M, from about $10^{-9}$ M to about $10^{-11}$ M, from about $10^{-10}$ M to about $10^{-11}$ M, from about $10^{-7}$ M to about $10^{-10}$ M, from about $10^{-7}$ M to about $10^{-10}$ M, from about $10^{-8}$ M to about $10^{-10}$ M, from about $10^{-9}$ M to about $10^{-10}$ M, from about $10^{-7}$ M to about $10^{-9}$ M, from about $10^{-7}$ M to about $10^{-9}$ M, from about $10^{-8}$ M to about $10^{-9}$ M, from about $10^{-7}$ M to about $10^{-8}$ M, or from about $10^{-7}$ M to about $10^{-8}$). In other embodiments, the antibody or antigen binding fragment thereof has a $K_D$ of about $10^{-7}$ M, about $10^{-7}$ M, about $10^{-8}$ M, about $10^{-9}$ M, about $10^{-10}$ M, about $10^{-11}$ M, or about $10^{-12}$ M. In some embodiments, the antibody or antigen binding fragment binds to one or more epitopes on MOSPD2. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with a $K_{on}$ of from about $10^3$ 1/Ms to about $10^6$ 1/Ms, or any range of values thereof (e.g., from about $10^3$ 1/Ms to about $10^5$ 1/Ms, from about $10^4$ 1/Ms to about $10^5$ 1/Ms, from about $10^4$ 1/Ms to about $10^6$ 1/Ms, from about $10^5$ 1/Ms to about $10^6$ 1/Ms, or from about $10^3$ 1/Ms to about $10^4$ 1/Ms). In other embodiments, the antibody or antigen binding fragment has a $K_{on}$ of about $10^3$ 1/Ms, about $10^4$ 1/Ms, about $10^5$ 1/Ms, or about $10^6$ 1/Ms.

In some embodiments, antibodies or antigen binding fragments of the invention bind to MOSPD2 with a $K_{off}$ of from about $10^{-3}$ 1/s to about $10^{-6}$ 1/s, or any range of values thereof (e.g., from about $10^{-3}$ 1/s to about $10^{-5}$ 1/s, from about $10^{-4}$ 1/s to about $10^{-5}$ 1/s, from about $10^{-4}$ 1/s to about $10^{-6}$ 1/s, from about $10^{-5}$ 1/s to about $10^{-6}$ 1/s, or from about $10^{-3}$ 1/s to about $10^{-4}$ 1/s). In other embodiments, the antibody or antigen binding fragment has a $K_{off}$ of about $10^{-3}$ 1/s, about $10^{-4}$ 1/s, about $10^{-5}$ 1/s, or about $10^{-6}$ 1/s.

In still other embodiments, the inhibitor is an RNAi, miRNA, siRNA, shRNA, an antisense RNA, an antisense DNA, a decoy molecule, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof. In some embodiments, the inhibitor hybridizes to a nucleotide sequence encoding a MOSPD2 polypeptide. In some embodiments, the hybridization is under a stringent condition or under a highly stringent condition.

In some embodiments, the inhibitor is a clustered regularly interspaced short palindromic repeats CRISPR-CAS9 system.

In further embodiments, a MOSPD2 polypeptide has a sequence at least about 75%, at least about 80%, at least about 85%, at least about 90%, at least about 95%, at least about 96%, at least about 97%, at least about 98%, at least about 99%, or 100% identical to any one of SEQ ID NOs:1-4. In other embodiments, the MOSPD2 polypeptide has a sequence at least 75%, at least 80%, at least 85%, at least 90%, at least 95%, at least 96%, at least 97%, at least 98%, or at least 99% identical to any one of SEQ ID NOs:1-4. In other embodiments, the MOSPD2 polypeptide has a sequence of about 75%, about 80%, about 85%, about 90%, about 95%, about 96%, about 97%, about 98%, or about 99% identical to any one of SEQ ID NOs:1-4. In other embodiments, the MOSPD2 polypeptide has a sequence with 75%, 80%, 85%, 90%, 95%, 96%, 97%, 98%, or 99% identity to any one of SEQ ID NOs:1-4. In other embodiments, the MOSPD2 polypeptide has a sequence with from about 75% to 100% identity to any one of SEQ ID NOs:1-4, or any range of values thereof, for example, from about 80% to 100% identity, from about 85% to 100% identity, from about 90% to 100% identity, from about 95% to 100% identity, from about 96% to 100% identity, from about 97% to 100% identity, from about 98% to 100% identity, from about 99% to about 100% identity, from about 75% to about 99% identity, from about 80% to about 99% identity, from about 85% to about 99% identity, from about 90% to about 99% identity, from about 95% to about 99% identity, from about 96% to about 99% identity, from about 97% to about 99% identity, from about 98% to about 99% identity, from about 99% to about 100% identity, from about 75% to about 95% identity, from about 80% to about 95% identity, from about 85% to about 95% identity, or from about 90% to about 95% identity to any one of SEQ ID NOs:1-4.

In further embodiments of the invention, the MOSPD2 polypeptide is encoded by a polynucleotide sequence having at least about 75%, at least about 80%, at least about 85%, at least about 90%, at least about 95%, at least about 96%, at least about 97%, at least about 98%, at least about 99%, or 100% identity to any one of SEQ ID NOs:5-8. In other embodiments, the MOSPD2 polypeptide is encoded by a polynucleotide sequence having at least 75%, at least 80%, at least 85%, at least 90%, at least 95%, at least 96%, at least 97%, at least 98%, or at least 99% identity to any one of SEQ ID NOs:5-8. In other embodiments, the MOSPD2 polypeptide is encoded by a polynucleotide sequence having about 75%, about 80%, about 85%, about 90%, about 95%, about 96%, about 97%, about 98%, or about 99% identity to any one of SEQ ID NOs:5-8. In other embodiments, the MOSPD2 polypeptide is encoded by a polynucleotide sequence 75%, 80%, 85%, 90%, 95%, 96%, 97%, 98%, or 99% identical to any one of SEQ ID NOs:1-4. In other embodiments, the MOSPD2 polypeptide is encoded by a polynucleotide sequence having from about 75% to 100% identity to any one of SEQ ID NOs:5-8, or any range of values thereof, for example, from about 80% to 100% identity, from about 85% to 100% identity, from about 90% to 100% identity, from about 95% to 100% identity, from about 96% to 100% identity, from about 97% to 100% identity, from about 98% to 100% identity, from about 99% to about 100% identity, from about 75% to about 99% identity, from about 80% to about 99% identity, from about 85% to about 99% identity, from about 90% to about 99% identity, from about 95% to about 99% identity, from about 96% to about 99% identity, from about 97% to about 99% identity, from about 98% to about 99% identity, from about 99% to about 100% identity, from about 75% to about 95% identity, from about 80% to about 95% identity, from about 85% to about 95% identity, or from about 90% to about 95% identity to any one of SEQ ID NOs:5-8.

Pharmaceutical Compositions

Other embodiments of the invention relate to a pharmaceutical composition comprising an inhibitor of MOSPD2. In some embodiments, the pharmaceutical composition comprises an inhibitor of MOSPD2 and a pharmaceutically acceptable carrier. In other embodiments, the pharmaceutical composition comprises a therapeutically effective amount of the inhibitor of MOSPD2 (e.g., an antibody or antigen binding fragment of an antibody described herein).

In other embodiments, the inhibitor of MOSPD2 is an antibody or antigen binding fragment of an antibody, and the therapeutically effective amount is from about 1 µg/ml to about 10 µg/ml, or any range of values thereof (e.g., from about 2 µg/ml to about 10 µg/ml, from about 3 µg/ml to about 10 µg/ml, from about 4 µg/ml to about 10 µg/ml, from about 5 µg/ml to about 10 µg/ml, from about 6 µg/ml to about 10 µg/ml, from about 7 µg/ml to about 10 µg/ml, from about 8 µg/ml to about 10 µg/ml, from about 9 µg/ml to about 10 µg/ml, from about 1 µg/ml to about 9 µg/ml, from about 2 µg/ml to about 9 µg/ml, from about 3 µg/ml to about 9 µg/ml, from about 4 µg/ml to about 9 µg/ml, from about 5 µg/ml to about 9 µg/ml, from about 6 µg/ml to about 9 µg/ml, from about 7 µg/ml to about 9 µg/ml, from about 8 µg/ml to about 9 µg/ml, from about 1 µg/ml to about 8 µg/ml, from about 2 µg/ml to about 8 µg/ml, from about 3 µg/ml to about 8 µg/ml, from about 4 µg/ml to about 8 µg/ml, from about 5 µg/ml to about 8 µg/ml, from about 6 µg/ml to about 8 µg/ml, from about 7 µg/ml to about 8 µg/ml, from about 1 µg/ml to about 7 µg/ml, from about 2 µg/ml to about 7 µg/ml, from about 3 µg/ml to about 7 µg/ml, from about 4 µg/ml to about 7 µg/ml, from about 5 µg/ml to about 7 µg/ml, from about 6 µg/ml to about 7 µg/ml, from about 1 µg/ml to about 6 µg/ml, from about 2 µg/ml to about 6 µg/ml, from about 3 µg/ml to about 6 µg/ml, from about 4 µg/ml to about 6 µg/ml, from about 5 µg/ml to about 6 µg/ml, from about 1 µg/ml to about 5 µg/ml, from about 2 µg/ml to about 5 µg/ml, from about 3 µg/ml to about 5 µg/ml, from about 4 µg/ml to about 5 µg/ml, from about 1 µg/ml to about 4 µg/ml, from about 2 µg/ml to about 4 µg/ml, from about 3 µg/ml to about 4 µg/ml, from about 1 µg/ml to about 3 µg/ml, from about 2 µg/ml to about 3 µg/ml, or from about 1 µg/ml to about 2 µg/ml). In other embodiments, the inhibitor of MOSPD2 is an antibody or antigen binding fragment of an antibody, and the therapeutically effective amount is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml.

In some embodiments, the inhibitor of MOSPD2 is an antibody or antigen binding fragment of an antibody, and the therapeutically effective amount is from about 10 mg/kg to about 40 mg/kg, or any range of values thereof (e.g., from about 15 mg/kg to about 40 mg/kg, from about 20 mg/kg to about 40 mg/kg, from about 25 mg/kg to about 40 mg/kg, from about 30 mg/kg to about 40 mg/kg, from about 35 mg/kg to about 40 mg/kg, from about 10 mg/kg to about 35 mg/kg, from about 15 mg/kg to about 35 mg/kg, from about 20 mg/kg to about 35 mg/kg, from about 25 mg/kg to about 35 mg/kg, from about 30 mg/kg to about 35 mg/kg, from about 10 mg/kg to about 30 mg/kg, from about 15 mg/kg to about 30 mg/kg, from about 20 mg/kg to about 30 mg/kg, from about 25 mg/kg to about 30 mg/kg, from about 10 mg/kg to about 25 mg/kg, from about 15 mg/kg to about 25 mg/kg, from about 20 mg/kg to about 25 mg/kg, from about 10 mg/kg to about 20 mg/kg, from about 15 mg/kg to about 20 mg/kg, or from about 10 mg/kg to about 15 mg/kg). In other embodiments, the inhibitor of MOSPD2 is an antibody or antigen binding fragment of an antibody, and the therapeutically effective amount is about 10 mg/kg, about 15 mg/kg, about 20 mg/kg, about 25 mg/kg, about 30 mg/kg, about 35 mg/kg, or about 40 mg/kg.

In some embodiments, the inhibitor of MOSPD2 (e.g., an antibody or antigen binding fragment thereof) is present in an amount such that administration of the MOSPD2 inhibitor causes at least 10% (e.g., at least 20%, at least 30%, at least 40%, at least 50%, at least 60%, at least 70%, at least 80%, at least 90%, at least 95%, at least 99%, or higher) inhibition of one or more activities of MOSPD2 (e.g., human MOSPD2) (e.g., MOSPD2 expression, inflammatory cell migration (e.g., leukocyte or monocyte migration), chemotaxis (e.g., leukocyte or monocyte chemotaxis), a chemokine signaling pathway, EGF receptor phosphorylation, ERK phosphorylation and AKT phosphorylation. In some embodiments, administration of the MOSPD2 inhibitor to a human subject causes at least 10% (e.g., at least 20%, at least 30%, at least 40%, at least 50%, at least 60%, at least 70%, at least 80%, at least 90%, at least 95%, at least 99%, or higher) inhibition of one or more activities of a human MOSPD2.

In another aspect, administration of the MOSPD2 inhibitor (e.g., an anti-MOSPD2 antibody or antigen binding fragment thereof) causes from about 10% to 100%, from about 10% to about 99%, from about 10% to about 95%, from about 10% to about 90%, from about 10% to about 85%, from about 10% to about 80%, from about 10% to about 70%, from about 20% to about 99%, from about 20% to about 95%, from about 20% to about 90%, from about 20% to about 85%, from about 20% to about 80%, from about 30% to about 95%, from about 30% to about 90%, from about 30% to about 85%, from about 30% to about 80%, from about 40% to about 95%, from about 40% to about 90%, from about 40% to about 85%, from about 40% to about 80%, from about 50% to about 95%, from about 50% to about 90%, from about 50% to about 85%, from about 50% to about 80%, from about 60% to about 95%, from about 60% to about 90%, from about 60% to about 85%, or from about 60% to about 80% inhibition of one or more activities of MOSPD2, e.g., regulation of inflammatory cell migration, chemokine signaling pathways, growth factor signaling pathways, EGF receptor phosphorylation, ERK phosphorylation, AKT phosphorylation, and/or FAK phosphorylation.

As used herein, a "pharmaceutical composition" refers to a preparation of one or more agents as described herein (e.g., a MOSPD2 inhibitor, or a MOSPD2 inhibitor with one or more other agents described herein), or physiologically acceptable salts or prodrugs thereof, with other chemical components, including, but not limited to, pharmaceutically acceptable carriers, excipients, lubricants, buffering agents, antibacterial agents, bulking agents (e.g., mannitol), antioxidants (e.g., ascorbic acid or sodium bisulfite), and the like. The purpose of the pharmaceutical composition is to facilitate administration of the agent(s) to a subject.

As used herein, "administration" or "administering" to a subject includes, but is not limited to, the act of a physician or other medical professional prescribing a pharmaceutical composition of the invention for a subject.

Herein, the phrase "pharmaceutically acceptable carrier" refers to a carrier or a diluent that does not cause significant irritation to the subject and does not abrogate the biological activity and properties of the agent(s) described herein.

As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient.

In some embodiments, a pharmaceutical composition comprising a MOSPD2 inhibitor further comprises one or more additional active agents.

When two or more agents are administered as a pharmaceutical composition, each agent may optionally be administered in a separate composition and/or via a different route of administration. Possible routes of administration for each agent independently include, but are not limited to, parenteral administration, transmucosal administration, rectal administration, buccal administration and/or inhalation (e.g., as described herein).

In some embodiments, the pharmaceutical composition is suitable for systemic or local administration. In other embodiments, the pharmaceutical composition is suitable for nasal, oral, or intra-peritoneal administration. In other embodiments, the pharmaceutical composition is suitable for intravenous administration, intramuscular administration or subcutaneous administration.

Methods of Treating, Preventing, or Reducing the Incidence of Inflammation and Inflammatory Diseases or Disorders Embodiments of the invention relate to a method for treating, preventing, or reducing the incidence of inflammation comprising administering an inhibitor of MOSPD2. In some embodiments, the invention relates to a method for treating, preventing, or reducing the incidence of an inflammatory disease or disorder comprising administering an inhibitor of MOSPD2. In other embodiments, the method comprises administering a therapeutically effective amount of an inhibitor of MOSPD2 to a subject in need thereof.

In some embodiments of the methods, the inhibitor of MOSPD2 is an antibody or antigen binding fragment of an antibody described herein. For example, the antibody or antigen binding fragment thereof can have an antibody-antigen equilibrium dissociation constant ($K_D$) of from $10^{-7}$ M to about $10^{-12}$ M, or any range of values thereof (e.g., from about $10^{-7}$ M to about $10^{-12}$, from $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-6}$ M to about $10^{-11}$ M, from about $10^{-7}$ M to about $10^{-11}$ M, from about $10^{-8}$ M to about $10^{-11}$ M, from about $10^{-7}$ M to about $10^{-11}$ M, from about $10^{-10}$ M to about $10^{-11}$ M, from about $10^{-7}$ M to about $10^{-10}$ M from about $10^{-7}$ M to about $10^{-10}$ M, from about $10^{-8}$ M to about $10^{-10}$ M, from about $10^{-7}$ M to about $10^{-10}$ M, from about $10^{-7}$ M to about $10^{-7}$ M to about $10^{-7}$ M, from about $10^{-8}$ M to about $10^{-7}$ M, from about $10^{-7}$ M to about $10^{-8}$ M, or from about $10^{-7}$ M to about $10^{-8}$). In other embodiments, the antibody or antigen binding fragment thereof has a $K_D$ of about $10^{-7}$ M, about $10^{-7}$ M, about $10^{-8}$ M, about $10^{-9}$ M, about $10^{-10}$ M, about $10^{-11}$ M, or about $10^{-12}$ M. In some embodiments, the antibody or antigen binding fragment binds to one or more epitopes on MOSPD2. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with a $K_{on}$ of from about $10^3$ 1/Ms to about $10^6$ 1/Ms, or any range of values thereof (e.g., from about $10^3$ 1/Ms to about $10^5$ 1/Ms, from about $10^4$ 1/Ms to about $10^5$ 1/Ms, from about $10^4$ 1/Ms to about $10^6$ 1/Ms, from about $10^5$ 1/Ms to about $10^6$ 1/Ms, or from about $10^3$ 1/Ms to about $10^4$ 1/Ms). In other embodiments, the antibody or antigen binding fragment has a $K_{on}$ of about $10^3$ 1/Ms, about $10^4$ 1/Ms, about $10^5$ 1/Ms, or about $10^6$ 1/Ms.

In some embodiments, antibodies or antigen binding fragments of the invention bind to MOSPD2 with a $K_{off}$ of from about 10' 1/s to about $10^{-6}$ 1/s, or any range of values thereof (e.g., from about $10^{-3}$ 1/s to about $10^{-5}$ 1/s, from about $10^{-4}$ 1/s to about $10^{-5}$ 1/s, from about $10^{-4}$ 1/s to about $10^{-6}$ 1/s, from about $10^{-5}$ 1/s to about 10' 1/s, or from about $10^{-3}$ 1/s to about $10^{-4}$ 1/s). In other embodiments, the antibody or antigen binding fragment has a $K_{off}$ of about 10' 1/s, about $10^{-4}$ 1/s, about $10^{-5}$ 1/s, or about $10^{-6}$ 1/s.

In some embodiments of the methods, the inhibitor of MOSPD2 is an antibody or antigen binding fragment of an antibody, and the therapeutically effective amount is from about 1 µg/ml to about 10 µg/ml, or any range of values thereof (e.g., from about 2 µg/ml to about 10 µg/ml, from about 3 µg/ml to about 10 µg/ml, from about 4 µg/ml to about 10 µg/ml, from about 5 µg/ml to about 10 µg/ml, from about 6 µg/ml to about 10 µg/ml, from about 7 µg/ml to about 10 µg/ml, from about 8 µg/ml to about 10 µg/ml, from about 9 µg/ml to about 10 µg/ml, from about 1 µg/ml to about 9 µg/ml, from about 2 µg/ml to about 9 µg/ml, from about 3 µg/ml to about 9 µg/ml, from about 4 µg/ml to about 9 µg/ml, from about 5 µg/ml to about 9 µg/ml, from about 6 µg/ml to about 9 µg/ml, from about 7 µg/ml to about 9 µg/ml, from about 8 µg/ml to about 9 µg/ml, from about 1 µg/ml to about 8 µg/ml, from about 2 µg/ml to about 8 µg/ml, from about 3 µg/ml to about 8 µg/ml, from about 4 µg/ml to about 8 µg/ml, from about 5 µg/ml to about 8 µg/ml, from about 6 µg/ml to about 8 µg/ml, from about 7 µg/ml to about 8 µg/ml, from about 1 µg/ml to about 7 µg/ml, from about 2 µg/ml to about 7 µg/ml, from about 3 µg/ml to about 7 µg/ml, from about 4 µg/ml to about 7 µg/ml, from about 5 µg/ml to about 7 µg/ml, from about 6 µg/ml to about 7 µg/ml, from about 1 µg/ml to about 6 µg/ml, from about 2 µg/ml to about 6 µg/ml, from about 3 µg/ml to about 6 µg/ml, from about 4 µg/ml to about 6 µg/ml, from about 5 µg/ml to about 6 µg/ml, from about 1 µg/ml to about 5 µg/ml, from about 2 µg/ml to about 5 µg/ml, from about 3 µg/ml to about 5 µg/ml, from about 4 µg/ml to about 5 µg/ml, from about 1 µg/ml to about 4 µg/ml, from about 2 µg/ml to about 4 µg/ml, from about 3 µg/ml to about 4 µg/ml, from about 1 µg/ml to about 3 µg/ml, from about 2 µg/ml to about 3 µg/ml, or from about 1 µg/ml to about 2 µg/ml). In other embodiments, the inhibitor of MOSPD2 is an antibody or antigen binding fragment of an antibody, and the therapeutically effective amount is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml.

In some embodiments of the methods, the inhibitor of MOSPD2 is an antibody or antigen binding fragment of an antibody, and the therapeutically effective amount is from about 10 mg/kg to about 40 mg/kg, or any range of values thereof (e.g., from about 15 mg/kg to about 40 mg/kg, from about 20 mg/kg to about 40 mg/kg, from about 25 mg/kg to about 40 mg/kg, from about 30 mg/kg to about 40 mg/kg, from about 35 mg/kg to about 40 mg/kg, from about 10 mg/kg to about 35 mg/kg, from about 15 mg/kg to about 35 mg/kg, from about 20 mg/kg to about 35 mg/kg, from about 25 mg/kg to about 35 mg/kg, from about 30 mg/kg to about 35 mg/kg, from about 10 mg/kg to about 30 mg/kg, from about 15 mg/kg to about 30 mg/kg, from about 20 mg/kg to about 30 mg/kg, from about 25 mg/kg to about 30 mg/kg, from about 10 mg/kg to about 25 mg/kg, from about 15 mg/kg to about 25 mg/kg, from about 20 mg/kg to about 25 mg/kg, from about 10 mg/kg to about 20 mg/kg, from about 15 mg/kg to about 20 mg/kg, or from about 10 mg/kg to about 15 mg/kg). In other embodiments, the inhibitor of MOSPD2 is an antibody or antigen binding fragment of an antibody, and the therapeutically effective amount is about 10 mg/kg, about 15 mg/kg, about 20 mg/kg, about 25 mg/kg, about 30 mg/kg, about 35 mg/kg, or about 40 mg/kg.

In some embodiments of the methods, the inhibitor of MOSPD2 (e.g., an antibody or antigen binding fragment thereof) causes at least 10% (e.g., at least 20%, at least 30%, at least 40%, at least 50%, at least 60%, at least 70%, at least 80%, at least 90%, at least 95%, at least 99%, or higher) inhibition of one or more activities of MOSPD (e.g., human MOSPD2) (e.g., MOSPD2 expression, inflammatory cell migration (e.g., leukocyte or monocyte migration), chemotaxis (e.g., leukocyte or monocyte chemotaxis), a chemokine signaling pathway, EGF receptor phosphorylation, ERK phosphorylation and AKT phosphorylation. In some embodiments, administration of the MOSPD2 inhibitor to a human subject causes at least 10% (e.g., at least 20%, at least 30%, at least 40%, at least 50%, at least 60%, at least 70%, at least 80%, at least 90%, at least 95%, at least 99%, or higher) inhibition of one or more activities of a human MOSPD2.

In another aspect, administration of the MOSPD2 inhibitor (e.g., an anti-MOSPD2 antibody or antigen binding fragment thereof) causes from about 10% to 100%, from about 10% to about 99%, from about 10% to about 95%, from about 10% to about 90%, from about 10% to about 85%, from about 10% to about 80%, from about 10% to about 70%, from about 20% to about 99%, from about 20% to about 95%, from about 20% to about 90%, from about 20% to about 85%, from about 20% to about 80%, from about 30% to about 95%, from about 30% to about 90%, from about 30% to about 85%, from about 30% to about 80%, from about 40% to about 95%, from about 40% to about 90%, from about 40% to about 85%, from about 40% to about 80%, from about 50% to about 95%, from about 50% to about 90%, from about 50% to about 85%, from about 50% to about 80%, from about 60% to about 95%, from about 60% to about 90%, from about 60% to about 85%, or from about 60% to about 80% inhibition of one or more activities of MOSPD2, e.g., regulation of inflammatory cell migration, chemokine signaling pathways, growth factor signaling pathways, EGF receptor phosphorylation, ERK phosphorylation, AKT phosphorylation, and/or FAK phosphorylation.

In other embodiments of the methods, the subject is a mammal or a human.

In other embodiments of the methods, the inflammatory disease or disorder is an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, necrosis, an inflammatory implant-related disease or disorder, an inflammatory aging process, an immunodeficiency disease or disorder, or an inflammatory pulmonary disease or disorder.

In some embodiments, the hypersensitivity is Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, or TH2 lymphocyte mediated hypersensitivity.

In other embodiments, the inflammatory cardiovascular disease or disorder is an occlusive disease or disorder, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, or anti-helper T lymphocyte autoimmunity.

The other embodiments, the inflammatory cerebrovascular disease or disorder is stroke, cerebrovascular inflammation, cerebral hemorrhage, or vertebral arterial insufficiency.

In other embodiments, the peripheral vascular disease or disorder is gangrene, diabetic vasculopathy, ischemic bowel disease, thrombosis, diabetic retinopathy, or diabetic nephropathy.

In some embodiments, the autoimmune disease or disorder is chronic rheumatoid arthritis, juvenile rheumatoid arthritis, systemic lupus erythematosus, scleroderma, mixed connective tissue disease, polyarteritis *nodosa*, polymyositis/dermatomyositis, Sjogren's syndrome, Bechet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides, or heparin induced thrombocytopenia.

In some embodiments, the inflammatory glandular disease or disorder is a pancreatic disease or disorder, Type I diabetes, thyroid disease or disorder, Graves' disease or disorder, thyroiditis, spontaneous autoimmune thyroiditis, Hashimoto's thyroiditis, idiopathic myxedema, ovarian autoimmunity, autoimmune anti-sperm infertility, autoimmune prostatitis, or Type I autoimmune polyglandular syndrome.

In some embodiments, the inflammatory gastrointestinal disease or disorder is colitis, ileitis, Crohn's disease, chronic inflammatory intestinal disease, inflammatory bowel syndrome, inflammatory bowel disease, irritable bowel syndrome, chronic inflammatory bowel disease, celiac disease, ulcerative colitis, an ulcer, a skin ulcer, a bed sore, a gastric ulcer, a peptic ulcer, a buccal ulcer, a nasopharyngeal ulcer, an esophageal ulcer, a duodenal ulcer, or a gastrointestinal ulcer.

In some embodiments, the inflammatory cutaneous disease or disorder is acne, autoimmune bullous skin disease or disorder, pemphigus vulgaris, bullous pemphigoid, pemphigus foliaceus, contact dermatitis, or drug eruption.

In some embodiments, the inflammatory hepatic disease or disorder is autoimmune hepatitis, hepatic cirrhosis, or biliary cirrhosis.

In some embodiments, the inflammatory neurological disease or disorder is multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease or disorder, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis, multiple sclerosis, stroke, an inflammatory retinal disease or disorder, an inflammatory ocular disease or disorder, optic neuritis, spongiform encephalopathy, migraine, headache, cluster headache, or stiff-man syndrome.

In some embodiments, the inflammatory connective tissue disease or disorder is Duchenne muscular dystrophy (DMD), autoimmune myositis, primary Sjogren's syndrome, smooth muscle autoimmune disease or disorder, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease or disorder, or an autoimmune disease or disorder of the inner ear.

In some embodiments, the inflammatory renal disease or disorder is autoimmune interstitial nephritis.

In some embodiments, the inflammatory reproductive disease or disorder is repeated fetal loss, ovarian cyst, or a menstruation associated disease or disorder.

In some embodiments, the inflammatory systemic disease or disorder is systemic lupus erythematosus, systemic sclerosis, septic shock, toxic shock syndrome, or cachexia.

In some embodiments, the infectious disease or disorder is a chronic infectious disease or disorder, a subacute infectious disease or disorder, an acute infectious disease or disorder, a viral disease or disorder, a bacterial disease or disorder, a protozoan disease or disorder, a parasitic disease or disorder, a fungal disease or disorder, a mycoplasma disease or disorder, gangrene, sepsis, a prion disease or disorder, influenza, tuberculosis, malaria, acquired immunodeficiency syndrome, or severe acute respiratory syndrome.

In some embodiments, the inflammatory transplantation-related disease or disorder is graft rejection, chronic graft rejection, subacute graft rejection, acute graft rejection hyperacute graft rejection, or graft versus host disease or disorder.

In some embodiments, the implant is a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, or a respirator tube.

In some embodiments, the inflammatory pulmonary disease or disorder is asthma, allergic asthma, emphysema, chronic obstructive pulmonary disease or disorder, sarcoidosis, or bronchitis.

In other embodiments, the inflammatory disease or disorder is fibrosis.

In some embodiments, the inflammatory disease or disorder is vascular inflammation in a subject suffering from a chronic autoimmune or chronic inflammatory disease. In some embodiments, the chronic autoimmune or inflammatory disease is psoriasis. In some embodiments, the vascular inflammation is associated with a cardiovascular disease, a peripheral vascular disease, a coronary artery disease, a cerebral vascular disease, a renal artery stenosis, an ischemic disease, or an aortic aneurism. In some embodiments, the vascular inflammation is associated with an ischemic heart disease, atherosclerosis, acute coronary syndrome, unstable angina, stable angina, or stroke. In other embodiments, the vascular inflammation is inflammation of a carotid artery. In other embodiments, the vascular inflammation is inflammation of an aorta.

In some embodiments, the inflammatory disease or disorder is inflammation associated with an implant. In some embodiments, the inflammation associated with an implant is a local inflammation or a systemic inflammatory reaction. In some embodiments, the implant is a silicone, a saline, a metal, a plastic, or a polymeric implant. In some embodiments, the implant is a cosmetic implant, a prosthetic implant, a subdermal implant, a transdermal implant, a bone replacement implant, or a bone fracture repair device. In some embodiments, the implant is a drug delivery implant or a drug release implant. In other embodiments, the implant is an artificial joint, an artificial heart, an artificial heart valve, a testicular prosthesis, a breast implant, a dental implant, an ocular implant, a cochlear implant, a penile implant, a cardiac implant, a catheter, an implantable urinary continence device, a pacemaker, an electrode, a Hernia support device, or a respirator tube.

In other embodiments, the inflammatory disease or disorder is hepatitis or steatohepatitis. In some embodiments, the inflammatory disease or disorder is nonalcoholic steatohepatitis (NASH). In some embodiments, the inflammatory disease or disorder is glomerulonephritis. In some embodiments, the inflammatory disease or disorder is focal segmental glomerulosclerosis (FSGS).

Because inflammation exerts influence on bone turnover, inducing osteoporosis, osteoporosis is also an example of an inflammatory disease or disorder of the present invention. Accordingly, in some embodiments of the invention, the inflammatory disease or disorder is osteoporosis.

Methods of Inhibiting or Preventing One or More Cell Activities

Embodiments of the invention also relate to methods of inhibiting or preventing one or more activities in a cell comprising administering an inhibitor of MOSPD2. In some embodiments, the method comprises administering a therapeutically effective amount of an inhibitor of MOSPD2 to a subject in need thereof.

In some embodiments, the inhibitor of MOSPD2 is an antibody or antigen binding fragment of an antibody described herein. For example, the antibody or antigen binding fragment thereof can have an antibody-antigen equilibrium dissociation constant ($K_D$) of from about $10^{-7}$ M to about $10^{-12}$ M, or any range of values thereof (e.g., from about $10^{-7}$ M to about $10^{-12}$ M, from $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-7}$ M to about $10^{-11}$ M, from about $10^{-7}$ M to about $10^{-11}$ M, from about $10^{-8}$ M to about $10^{-11}$ M, from about $10^{-7}$ M to about $10^{-11}$ M, from about $10^{-10}$ M to about $10^{-11}$ M, from about $10^{-7}$ M to about $10^{-10}$ M, from about $10^{-7}$ M to about $10^{-10}$ M, from about $10^{-8}$ M to about $10^{-10}$ M, from about $10^{-7}$ M to about $10^{-10}$ M, or from about $10^{-7}$ M to about $10^{-7}$ M, from about 10' to about 10', from about $10^{-8}$ M to about $10^{-7}$ M, from about $10^{-7}$ M to about $10^{-8}$, or from about $10^{-7}$ M to about $10^{-8}$ M). In other embodiments, the inhibitor of MOSPD2 is an antibody or antigen binding fragment of an antibody having a $K_D$ of about $10^{-7}$ M, about $10^{-7}$ M, about $10^{-8}$ M, about $10^{-7}$ M, about $10^{-10}$ M, about $10^{-11}$ M, or about $10^{-12}$ M. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with a $K_{on}$ of from about $10^3$ 1/Ms to about $10^6$ 1/Ms, or any range of values thereof (e.g., from about $10^3$ 1/Ms to about $10^5$ 1/Ms, from about $10^4$ 1/Ms to about $10^5$ 1/Ms, from about $10^4$ 1/Ms to about $10^6$ 1/Ms, from about $10^5$ 1/Ms to about $10^6$ 1/Ms, or from about $10^3$ 1/Ms to about $10^4$ 1/Ms). In other embodiments, the antibody or antigen binding fragment has a $K_{on}$ of about $10^{-3}$ 1/Ms, about $10^{-4}$ 1/Ms, about $10^{-5}$ 1/Ms, or about 10' 1/Ms.

In some embodiments, antibodies or antigen binding fragments of the invention bind to MOSPD2 with a $K_{off}$ of from about 10' 1/s to about $10^{-6}$ 1/s, or any range of values thereof (e.g., from about $10^{-3}$ 1/s to about $10^{-5}$ 1/s, from about $10^{-4}$ 1/s to about $10^{-5}$ 1/s, from about $10^{-4}$ 1/s to about 10' 1/s, from about $10^{-5}$ 1/s to about 10' 1/s, or from about $10^{-3}$ 1/s to about $10^{-4}$ 1/s). In other embodiments, the antibody or antigen binding fragment has a $K_{off}$ of about 10' 1/s, about $10^{-4}$ 1/s, about $10^{-5}$ 1/s, or about $10^{-6}$ 1/s.

In some embodiments, the inhibitor of MOSPD2 is an antibody or antigen binding fragment of an antibody, and the therapeutically effective amount is from about 1 µg/ml to about 10 µg/ml, or any range of values thereof (e.g., from about 2 µg/ml to about 10 µg/ml, from about 3 µg/ml to about 10 µg/ml, from about 4 µg/ml to about 10 µg/ml, from about 5 µg/ml to about 10 µg/ml, from about 6 µg/ml to about 10 µg/ml, from about 7 µg/ml to about 10 µg/ml, from about 8 µg/ml to about 10 µg/ml, from about 9 µg/ml to about 10 µg/ml, from about 1 µg/ml to about 9 µg/ml, from about 2 µg/ml to about 9 µg/ml, from about 3 µg/ml to about 9 µg/ml, from about 4 µg/ml to about 9 µg/ml, from about 5 µg/ml to about 9 µg/ml, from about 6 µg/ml to about 9 µg/ml, from about 7 µg/ml to about 9 µg/ml, from about 8 µg/ml to about 9 µg/ml, from about 1 µg/ml to about 8 µg/ml, from about 2 µg/ml to about 8 µg/ml, from about 3 µg/ml to about 8 µg/ml, from about 4 µg/ml to about 8 µg/ml, from about 5 µg/ml to about 8 µg/ml, from about 6 µg/ml to about 8 µg/ml, from about 7 µg/ml to about 8 µg/ml, from about 1 µg/ml to about 7 µg/ml, from about 2 µg/ml to about 7 µg/ml, from about 3 µg/ml to about 7 µg/ml, from about 4 µg/ml to about 7 µg/ml, from about 5 µg/ml to about 7 µg/ml, from about 6 µg/ml to about 7 µg/ml, from about 1 µg/ml to about 6 µg/ml, from about 2 µg/ml to about 6 µg/ml, from about 3 µg/ml to about 6 µg/ml, from about 4 µg/ml to about 6 µg/ml, from about 5 µg/ml to about 6 µg/ml, from about 1 µg/ml to about 5 µg/ml, from about 2 µg/ml to about 5 µg/ml, from about 3 µg/ml to about 5 µg/ml, from about 4 µg/ml to about 5 µg/ml, from about 1 µg/ml to about 4 µg/ml, from about 2 µg/ml to about 4 µg/ml, from about 3 µg/ml to about 4 µg/ml, from about 1 µg/ml to about 3 µg/ml, from about 2 µg/ml to about 3 µg/ml, or from about 1 µg/ml to about 2 µg/ml). In other embodiments, the inhibitor of MOSPD2 is an antibody or antigen binding fragment of an antibody, and the therapeutically effective amount is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml.

In some embodiments, the inhibitor of MOSPD2 is an antibody or antigen binding fragment of an antibody, and the therapeutically effective amount is from about 10 mg/kg to about 40 mg/kg, or any range of values thereof (e.g., from about 15 mg/kg to about 40 mg/kg, from about 20 mg/kg to about 40 mg/kg, from about 25 mg/kg to about 40 mg/kg, from about 30 mg/kg to about 40 mg/kg, from about 35 mg/kg to about 40 mg/kg, from about 10 mg/kg to about 35 mg/kg, from about 15 mg/kg to about 35 mg/kg, from about 20 mg/kg to about 35 mg/kg, from about 25 mg/kg to about 35 mg/kg, from about 30 mg/kg to about 35 mg/kg, from about 10 mg/kg to about 30 mg/kg, from about 15 mg/kg to about 30 mg/kg, from about 20 mg/kg to about 30 mg/kg, from about 25 mg/kg to about 30 mg/kg, from about 10 mg/kg to about 25 mg/kg, from about 15 mg/kg to about 25 mg/kg, from about 20 mg/kg to about 25 mg/kg, from about 10 mg/kg to about 20 mg/kg, from about 15 mg/kg to about 20 mg/kg, or from about 10 mg/kg to about 15 mg/kg). In other embodiments, the inhibitor of MOSPD2 is an antibody or antigen binding fragment of an antibody, and the therapeutically effective amount is about 10 mg/kg, about 15 mg/kg, about 20 mg/kg, about 25 mg/kg, about 30 mg/kg, about 35 mg/kg, or about 40 mg/kg.

In some embodiments, the inhibitor of MOSPD2 (e.g., an antibody of antigen binding fragment thereof) causes at least about 10% (e.g., at least about 20%, at least about 30%, at least about 40%, at least about 50%, at least about 60%, at least about 70%, at least about 80%, at least about 90%, at least about 95%, at least about 99%, or higher) inhibition of one or more activities of MOSPD2 (e.g., human MOSPD2) (e.g., MOSPD2 expression, inflammatory cell migration (e.g., leukocyte or monocyte migration), chemotaxis (e.g., leukocyte or monocyte chemotaxis), a chemokine signaling pathway, EGF receptor phosphorylation, ERK phosphorylation, AKT phosphorylation and/or FAK phosphorylation. In some embodiments, administration of the MOSPD2 inhibitor to a human subject causes at least about 10% (e.g., at least about 20%, at least about 30%, at least about 40%, at least about 50%, at least about 60%, at least about 70%, at least about 80%, at least about 90%, at least about 95%, at least about 99%, or higher) inhibition of one or more activities of a human MOSPD2.

In some embodiments, the one or more activities is one or more of: MOSPD2 expression, migration of an inflammatory cell, chemotaxis, a chemokine signaling pathway, ERK phosphorylation, AKT phosphorylation and/or FAK phosphorylation. In some embodiments, at least two, at least three, at least four, at least five, or all of these activities are inhibited.

In some embodiments, at least leukocyte chemotaxis and a chemokine signaling pathway are inhibited. In other embodiments, the inhibiting of a chemokine signaling pathway is the inhibiting of ERK phosphorylation and/or AKT phosphorylation. In other embodiments, the chemotaxis is induced by more than one chemokine or chemokine receptor.

In some embodiments, the inflammatory cell is, for example, a leukocyte, granulocyte, neutrophil, basophil, eosinophil, monocyte, macrophage, or mast cell.

In other embodiments, the chemotaxis is associated with an inflammatory cell such as a leukocyte or monocyte.

In some embodiments, the chemokine is CCL14, CCL19, CCL20, CCL21, CCL25, CCL27, CXCL12, CXCL13, CXCL-8, CCL2, CCL3, CCL4, CCL5, CCL11, CXCL10, CCL7, CCL8, CCL13, CCL17 or CCL22. In other embodiments, the migration or chemotaxis is induced by one or more of RANTES, MCP-3, MCP-1 and SDF-1.

EXAMPLES

Reference is now made to the following examples, which together with the above descriptions illustrate some embodiments of the invention in a non-limiting fashion.

Materials and Methods

MOSPD2 Inhibition

The U937 monocytic cell line (CRL-1593.2) was obtained from the American Type Culture Collection (ATCC) (Manassas, VA). The cells ($2\times10^6$ in 2 ml) were placed in a 15 ml tube. Control Lenti-virus particles ($2\times10^5$ viral particles) (SHC202V, Sigma, Israel) or Lenti-virus particles containing MOSPD2 sh-RNA ($2\times10^6$ viral particles; Sigma) were applied to the cells, which were then centrifuged for 60 min at 2000 rpm, room temperature in the presence of 8 µg/ml polybrene (Sigma). Artificial shRNA hairpin sequences and their corresponding target sequences on MOSPD2 are provided in SEQ ID NOs:9-14. The cells were then seeded in a 6-well plate in RPMI medium containing glutamine, 10% fetal calf serum (FCS) and penicillin/streptomycin all from Biological Industries (Beit Haemek, Israel). After 72 hours, fresh medium containing puromycin (4 µg/ml, Sigma) was added for the selection of transduced cells.

Cell Migration Trans-Well Assay

To test for chemokine-induced cell migration, RANTES (CCL5, 100 ng/ml), MCP-1 (CCL2, 100 ng/ml), MCP-3 (CCL7, 100 ng/ml), or SDF-1 (CXCL12, 25 ng/ml) (Pepro-Tech, Israel) were dissolved in RPMI-1640 medium supplemented with 0.5% fetal bovine serum (FBS) and placed at the lower chamber of QCM 24-well, 5 mm pore, migration assay plates (Corning-Costar, Corning, NY). U937 cells ($3\times10^5$) were transduced with control Lenti-virus particles or Lenti-virus particles containing MOSPD2 sh-RNA (sh-MOSPD2) were seeded in the upper chamber and incubated for 2-4 hours. Subsequently, the number of cells which migrated to the lower compartment was determined by fluorescence-activated cell sorting (FACS).

Western Blotting sh-control or sh-MOSPD2 Lenti-virus transduced U937 cells ($10^6$) were starved for 3 hours in RPMI medium containing 0.5% FCS (Biological Industries, Beit Haemek, Israel) and then activated with RANTES (100 ng/ml), MIP-1α (100 ng/ml), MCP-3 (100 ng/ml) or SDF-1 (25 ng/ml) for 5 minutes. Cells were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto nitrocellulose membrane. Blots were blocked with 5% milk or bovine serum albumin (BSA) in Tris buffered saline and Tween 20 (TBST) for 1 hour, followed by incubation with primary and secondary antibodies. Membranes were developed using an ECL kit (Thermo Scientific). The following antibodies were used for immunoblotting:

Primary antibodies: anti-Tubulin (1:4000) and anti-phospho extracellular-regulated kinase (p-ERK1/2) (Thr 183 and Tyr 185, 1:4000) antibodies were purchased from Sigma (Israel). Anti-phospho-AKT (Ser 473, 1:1000) antibodies were purchased from Cell Signaling. Anti-heat shock protein 90 (HSP90) (1:1000) antibodies were purchased from Santa Cruz Biotechnology (Dallas, TX).

Secondary antibodies: Horseradish peroxidase (HRP) donkey anti-rabbit (1:5000) and HRP goat anti-mouse (1:5000) antibodies were purchased from Jackson ImmunoResearch (West Grove, PA).

Q-PCR

To determine MOSPD2 inhibition, RNA was extracted from U937 cells transduced with control Lenti-virus particles or Lenti-virus particles containing sh-MOSPD2 using an RNeasy mini kit (Qiagen, Valencia, CA). For cDNA preparation, 2 µg of RNA was combined with qScript reaction mix and qScript reverse transcriptase (Quanta Bioscience, Gaithersburg, MD). The reaction was placed in a thermal cycler (BioRad, Hercules, CA) and a run program was set according to the manufacturer instructions. Real-time PCR reactions were performed on an Applied Biosystems 7300 real time PCR system (Grand Island, NY) using sets of primers for human MOSPD2, 28S to normalize RNA levels (Biosearch Technologies, Petaluma, CA), and SYBR Green PCR Master Mix (Applied Biosystems, Warrington, UK).

MOSPD2 Tranfection

HEK293 cells were transfected for 48 hours with empty plasmid or plasmid encoding hemagglutinin (HA)-tagged human MOSPD2 using jetPRIME transfection reagent (Polyplus transfection, France). Transfection efficiency was determined by flow cytometry using anti-HA-PE (miltenyi Biotec, Germany) antibody.

Isolation of Human Monocytes

Venous blood samples were obtained from healthy male donors in compliance with the Institutional Review Board at the Sheba Medical Center, Ramat Gan, Israel. Peripheral blood mononuclear cells (PBMCs) were isolated on Ficoll-Paque PLUS (GE Healthcare, Sweden) using 50 ml Leucosep tubes (Greiner Bio-One, Germany). Cells were washed in phosphate buffered saline (PBS) (Beit Haemek, Israel), and incubated at 4° C. for 15 min in a buffer containing PBS and 0.5% bovine serum albumin (BSA) with human CD14 microbeads (Miltenyi Biotec, Bergisch Gladbach, Germany).

Sub-Cellular Fractionation

Fractionation of cellular compartments was performed using the Subcellular Protein Fractionation Kit (Thermo Fisher Scientific) according to manufacturer instructions.

Cell Proliferation

U937 cells transduced with control Lenti-virus particles or Lenti-virus particles containing sh-MOSPD2 were seeded in 6-well plates ($10^4$ per well) in RPMI medium containing glutamine, 10% FCS and penicillin/streptomycin all from Biological Industries (Beit Haemek, Israel). The cells were counted by FACS every 24 hours in triplicate wells for 3 consecutive days.

Example 1

MOSPD2 and Chemokine-Induced Monocyte Migration

To assess the role of MOSPD2 in monocyte migration, MOSPD2 expression was silenced in U937 cells as described in the Materials and Methods section using Lenti-virus particles containing sh-RNA directed against three different regions of MOSPD2 mRNA (sh-MOSPD2). MOSPD2 mRNA expression in the cells was assessed using quantitative PCR (Q-PCR) and normalized to (3-actin expression as control. FIG. 1 shows that all tested sh-MOSPD2 profoundly reduced mRNA expression levels of human MOSPD2. U937 cells transduced with control Lenti-virus particles or with sh-MOSPD2 Lenti-virus particles were then tested for migration towards the chemokine, RANTES, using a trans-well migration assay. FIGS. 2 and 3 show that cell migration induced by RANTES was significantly inhibited in sh-MOSPD2 transduced cells compared to cells in which MOSPD2 was not silenced.

Example 2

MOSPD2, ERK Phosphorylation and AKT Phosphorylation

Figure 4B:
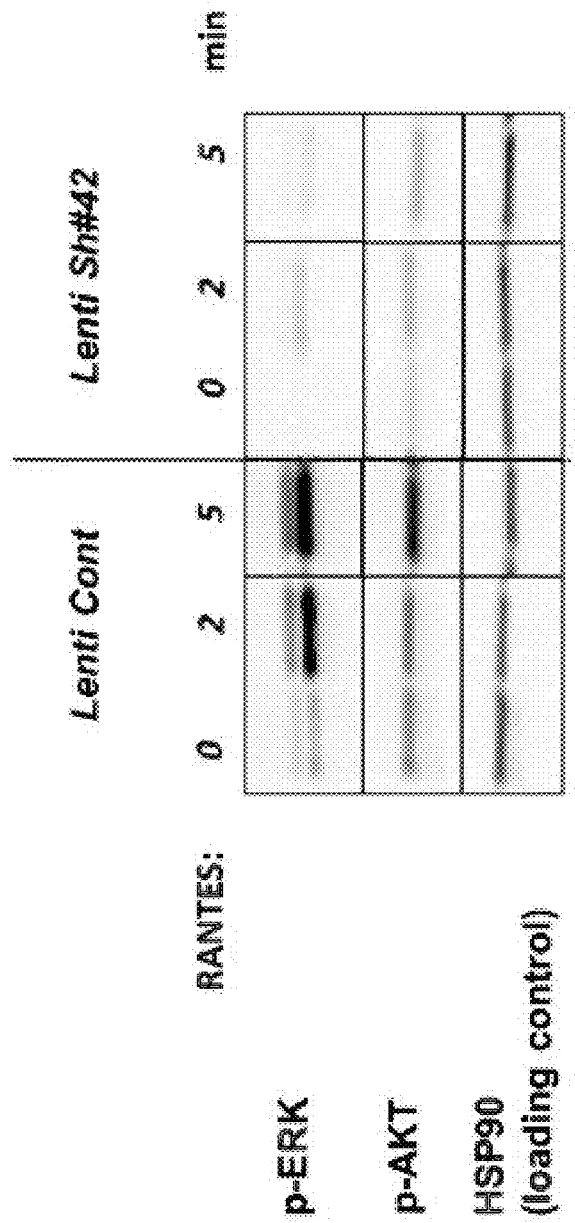

The effect of MOSPD2 inhibition on the activation of chemokine-induced signaling pathways was determined by testing the effects of MOSPD2 inhibition on phosphorylation of ERK and AKT. U937 cells transduced with control Lenti-virus particles or sh-MOSPD2 Lenti-virus particles were treated with RANTES for 2 or 5 minutes and then analyzed by western blot for phosphorylated ERK and AKT. Heat shock protein 90 (HSP90) was used as a loading control. FIG. 4A and FIG. 4B show that inhibition of MOSPD2 almost completely abolished RANTES-induced phosphorylation of ERK and AKT.

Example 3

MOSPD2 and Chemokine Receptor-Driven Signaling

Figure 5:
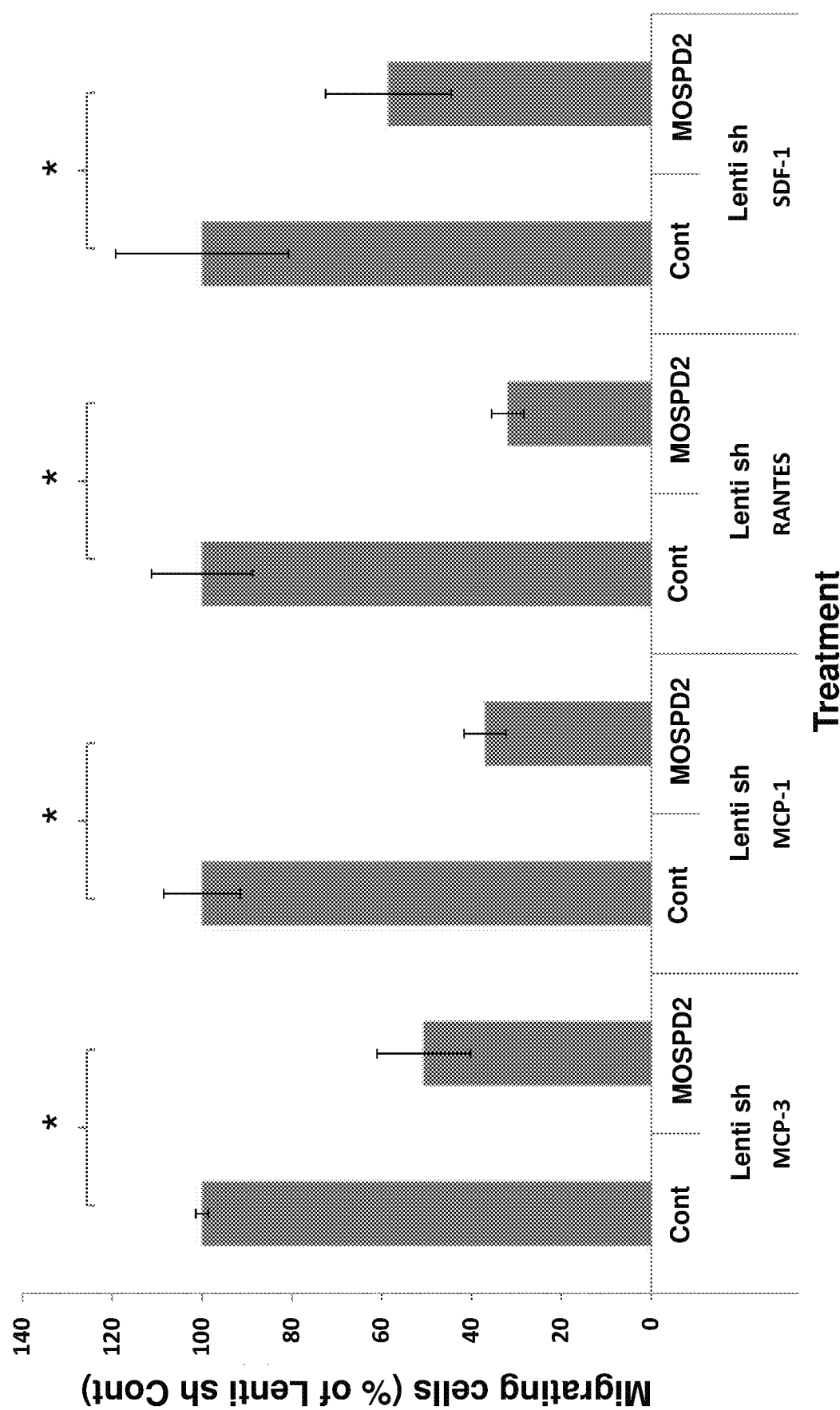
FIG. 5 shows the effect of MOSPD2 inhibition on chemokine-induced U937 cell migration. U937 cells transduced with control Lenti-virus particles (Lenti sh-Cont) or Lenti sh-MOSPD2 Lenti-virus particles (Lenti sh-MOSPD2) were tested for migration towards MCP-3, MCP-1, RANTES and SDF-1 in a trans-well assay. The results shown are the mean percentages of migrating cells±standard deviation of triplicate wells. *$p<0.05$.
Figure 6:
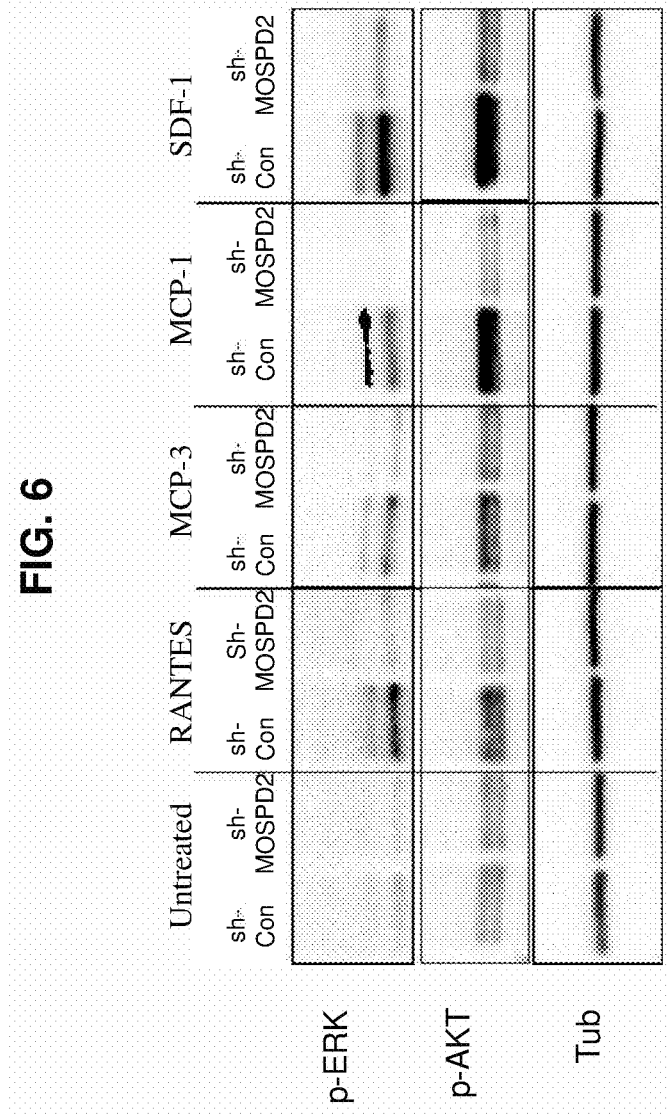
FIG. 6 presents images of Western blots showing the effect of MOSPD2 inhibition on phosphorylated ERK (p-ERK) and phosphorylated AKT (p-AKT) levels after activation with chemokines. U937 cells transduced with control Lenti-virus particles (sh-Con) or sh-MOSPD2 were treated with RANTES, MCP-3, MCP-1 and SDF-1. Expression of tubulin (Tub) is also shown as a loading control.

The effect of MOSPD2 inhibition on other chemokines was also tested. U937 cells transduced with control Lenti-virus particles or sh-MOSPD2 Lenti-virus particles were tested for migration towards MCP-3, MCP-1, RANTES and SDF-1 in a trans-well assay and for levels of phosphorylated ERK and AKT by western blot. FIG. 5 shows that MOSPD2 inhibition significantly inhibited cell migration induced by all the tested chemokines. Furthermore, FIG. 6 shows that inhibition of MOSPD2 almost completely abolished phosphorylation of ERK and AKT induced by all the tested chemokines. As such, the effects of MOSPD2 inhibition on migration and signaling are not limited to a single chemokine or chemokine receptor pathway.

Example 4

MOSPD2 and U937 Cell Proliferation

The effect of MOSPD2 inhibition on U937 cell proliferation was also tested. U937 cells transduced with control Lenti-virus particles or sh-MOSPD2 Lenti-virus particles were seeded as described in the Methods and Materials and counted every 24 hours for three consecutive days. FIG. 7 shows that MOSPD2 inhibition did not affect U937 proliferation, suggesting that the effects of MOSPD2 inhibition on migration and signaling occur by inhibition of intracellular processes downstream of chemokine receptors, and not by inhibiting monocyte activity in general.

Example 5

Anti-MOSPD2 Antibodies

Anti-MOSPD2 polyclonal antibodies were generated according to the following methods.

Materials and Methods

Production and Purification of Hemagglutinin MA)-Tagged Recombinant Human MOSPD2 (HA-rhMOSPD2)

Full length human MOSPD2 cDNA was inserted, using EcoRI and XbaI restriction sites, into the lentivirus plasmid vector pLVX-EF1α-IRES-Puro (Clonetech, CA). Oligonucleotide encoding the HA-tag (YPYDVPDYA; SEQ ID NO:15) was inserted into the N-terminal region of MOSPD2 with EcoRI restriction sites. For transduction, A2058 melanoma cells (ATCC CRL-11147, VA) were spun for 60 minutes at 2000 rpm at room temperature in the presence of 8 µg/ml polybrene (Sigma, Israel) and lentiviral particles containing HA-rhMOSPD2 expressing vector. The cells were then seeded in a 6 well plate. After 72 hours, fresh medium containing puromycin (4 µg/ml Sigma, Israel) was added for the selection of transduced cells. To purify HA-rhMOSPD2, A2058 transduced cells were lysed with M-PER mammalian protein extraction reagent (Thermo Scientific) and passed through anti-HA agarose beads (Thermo Scientific). Glycine or sodium thiocyanate was used for the elution of HA-rhMOSPD2 from the beads, followed by thorough dialysis against PBS.

Generation and Isolation of α-MOSPD2 Polyclonal Antibodies

Rabbits were immunized with approximately 0.5 mg of HA-rhMOSPD2 emulsified in complete freunds adjuvant followed by three boosts every three weeks with approximately 0.25 mg of HA-rhMOSPD2 emulsified in incomplete freunds adjuvant. Serum was collected one week after each boost to assess for antibody immunogenicity and titers. α-MOSPD2 antibodies were isolated from serum using protein A/G beads (SantaCruz, CA).

Results

Rabbit Polyclonal α-MOSPD2 Antibodies Detect and Precipitate Endogenous Human MOSPD2

Figure 8B:
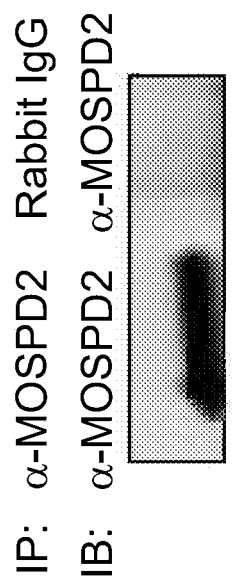
FIGS. 8A-8B present images of Western blots showing that isolated rabbit polyclonal α-MOSPD2 antibodies detect and precipitate endogenous human MOSPD2.
Figure 8A:
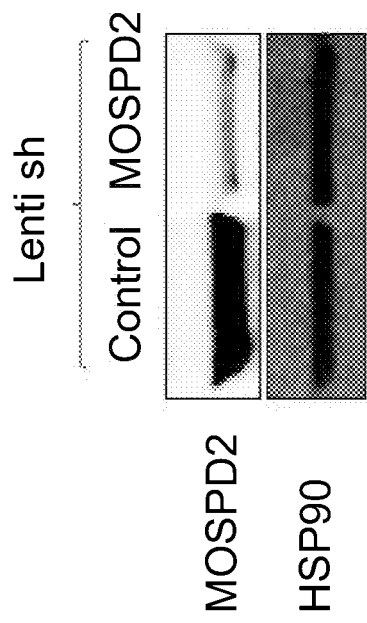

Isolated α-MOSPD2 polyclonal antibodies were evaluated for their ability to detect and precipitate endogenous MOSPD2. Cell lysate was prepared from U937 cells transduced with control or sh-MOSPD2 Lenti-virus particles. Samples were analyzed by Western blot using the isolated α-MOSPD2 antibodies (diluted 1:5000). Expression of HSP90 was determined as a loading control. Immunoprecipitation of U397 cell lysate was also performed using the isolated α-MOSPD2 antibodies or rabbit IgG (10 μg) as a control. The resulting precipitates were analyzed by immunoblot with the isolated α-MOSPD2 antibodies, followed by incubation with goat anti-rabbit antibody-HRP (1:5000). FIG. 8 shows that the isolated α-MOSPD2 antibodies readily detect (FIG. 8A) and immunoprecipitate (FIG. 8B) endogenously expressed MOSPD2 in U937 cells.

Example 6

MOSPD2 Subcellular Localization

Figure 9A:
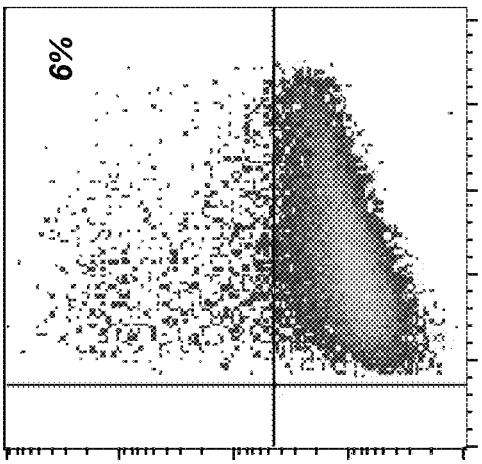
FIGS. 9A-9B present histograms showing that MOSPD2 is expressed on the cell surface of transfected HEK293 cells. HEK293 cells were transfected with empty vector (FIG. 9A) or HA-rhMOSPD2 plasmid (MOSPD2-HA)(FIG. 9B). The transfected cells were collected and stained with anti HA-PE antibody. Expression of MOSPD2 was assessed using FACSCalibur (BD Bioscience).
Figure 9B:
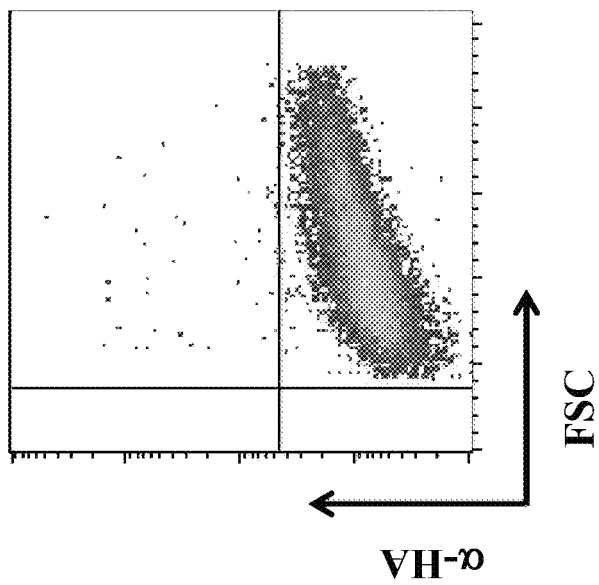
Figure 10:
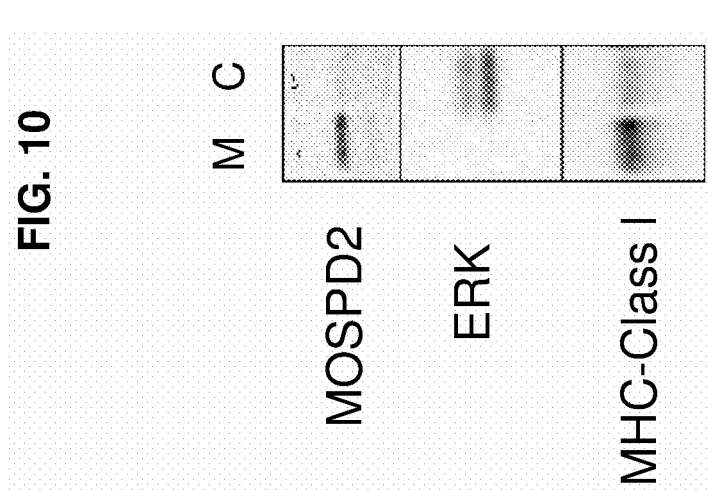
FIG. 10 presents an image showing that MOSPD2 is localized to the membrane fraction in human CD14 monocytes isolated from peripheral blood.

The subcellular localization of MOSPD2 was studied using HEK293 cells, which were transfected with empty or HA-tagged human MOSPD2 plasmids as described in the Methods and Materials. HEK293 cells were then stained with anti-HA antibody under conditions which allow surface staining only (no detergents). FIG. 9A-9B shows that cells transfected with HA-tagged MOSPD2 plasmid expressed the protein on the cell plasma membrane. To determine whether endogenous MOSPD2 can also be localized to cells membrane, subcellular fractions were isolated from primary human CD14 monocytes and tested for the presence of MOSPD2 (see Methods and Materials). The results in FIG. 10 show that MOSPD2 is found in the membrane and not in the cytoplasmic fraction. ERK and MHC Class I antibodies were used to demonstrate purity of cytoplasmic and membrane fractions, respectively.

Example 7

VB-201 Inhibits MOSPD2

Labeling of VB-201 and VB-221

VB-201 and VB-221 were labeled with biotin as follows. VB-201, VB-221 and ovalbumin (OVA, Sigma, Israel) were dissolved in 0.1M MES buffer (Thermo Scientific, Rockford, IL) and conjugated using EDC [1-ethyl-3-(dimethyl-aminopropyl) carbodiimide HCL] (Thermo Scientific) at a molar ratio of 100 (VB-201/VB-221):1 (OVA):240 (EDC) for 2-3 hr at room temperature. After which, samples were transferred to 10 kDa dialysis cassettes (Thermo Scientific) and dialyzed overnight against PBS. The ovalbumin bound VB-201 (OB201) and VB-221 (OB221) were then conjugated with amine-PEG2-biotin (in 0.1M MES buffer) using EDC at a molar ratio of 1 (OB201/OB221):100 (amine-PEG2-biotin):700 (EDC). The reaction was allowed to proceed for 2-3 hr at room temperature after which samples were again transferred to a 10 kDa dialysis cassette and dialyzed overnight against PBS.

VB-201 and VB-221 Cell-Surface Binding Specificity by Flow Cytometry

Streptavidin-APC (eBioscience, San Diego, CA) was used to detect binding of labelled VB-201 or VB-221 in flow cytometry experiments.

Precipitation

Cells were lysed using a 1% NP-40 lysis buffer containing 1:100 protease and phosphatase inhibitors, followed by 20 min incubation on ice and 15 min centrifugation at maximum speed. Samples were incubated overnight at 4° C. with solvent, OB201 or OB221 in a rotator. Streptavidin agarose beads (Sigma, Israel) were added for 2 hours. Protein elution was performed with lysis buffer without DTT for 10 min at room temperature. Sample loading, transfer and immunoblotting were performed as described above.

Results

VB-201 Binds Surface Expressed MOSPD2

It was previously shown that VB-201 inhibits migration of monocytes in vitro and in vivo. However, VB-221, a derivative of VB-201, did not inhibit chemokine-induced signaling and migration in human monocytes. Using labeled VB-201 and VB-221, proteins from human monocytes were precipitated and differential display by Mass-Spectrometry, was studied. The Mass-Spectrometry results revealed that MOSPD2 has a strong binding to VB-201 but not VB-221.

To further validate these results, labelled VB-201 and VB-221 were employed on cell lysates from human CD14 monocytes. Samples were then probed with anti MOSPD2 and TLR2. Whereas VB-201 and VB-221 precipitated TLR2 in a comparable intensity, VB-201 precipitated MOSPD2 markedly more intense than VB-221 (FIG. 11). These results also indicate that VB-201 binds MOSPD2.

Studies were also conducted to assess whether VB-201 can bind MOSPD2 in its native form, when expressed on the cell surface. Thus, HEK293 cells were transfected with a plasmid encoding HA-tagged human MOSPD2 and then stained with labelled VB-201 or VB-221. FIG. 12A-12C shows profound staining of labelled VB-201 to cells that express MOSPD2 (HA positive), while only weak staining was detected with labelled VB-221. Collectively, these results show that VB-201 can bind cell surface expressed human MOSPD2.

Example 8

Generation of Anti MOSPD2 (Fab)$_2$ Monoclonal Antibodies

Anti-MOSPD2 (Fab')$_2$ monoclonal antibodies (mAb) were obtained using the HuCAL PLATINUM® Platform (Bio-Rad AbD Serotec, GmnH) which contains a selection of phage displayed human Fab.

Briefly, recombinant protein of the extracellular region of MOSPD2 fused to human Fc was immobilized on a solid support. The HuCAL® library presented on phage particles was incubated with the immobilized antigen. Nonspecific antibodies were removed by extensive washing and specific antibody phages were eluted by adding a reducing agent.

Antibody DNA was isolated as a pool and subcloned into an E. coli expression vector to generate bivalent F(ab')₂ mAb. Colonies were picked and grown in a microtiter plate. The cultures ware lysed to release the antibody molecules and screened for specific antigen binding by ELISA and FACS. Unique antibodies were expressed and purified using one-step affinity chromatography, and then tested again by ELISA and FACS for specificity.

FIG. 13 lists 17 anti-MOSPD2 F(ab')₂ monoclonal antibody clones that were identified following a primary screen for binding to cells over-expressing MOSPD2. Further analysis of the clones for MOSPD2 binding with ELISA identified 12 clones having values greater than 5 times over background (* in FIG. 13).

Example 9

Anti-MOSPD2 Flab)₂ mAb Bind Human MOSPD2 Overexpressed on Cells

A2058 melanoma cells were transfected with HA-tagged human MOSPD2 to generate cells overexpressing MOSPD2.

Binding of the 12 antibody clones identified in Example 8 to MOSPD2 was then tested using flow cytometry with these cells. Specifically, $10^5$ cells were incubated with 2.5 µg of F(ab')₂ mAb at 4° C. for 1 hr in 100 µl of FACS buffer (PBS+2% FCS+0.02% sodium azide). Cells were then washed, resuspended in FACS buffer and stained for 30 min at 4° C. with Alexa-Fluor 647-conjugated (Fab')₂ goat anti-human IgG, F(ab')₂ 1:200 (Cat#109-606-097, Jackson Immunoresearch, PA). Cells were washed, resuspended in FACS buffer and analyzed on a FACS-Calibur device.

Figure 14A:
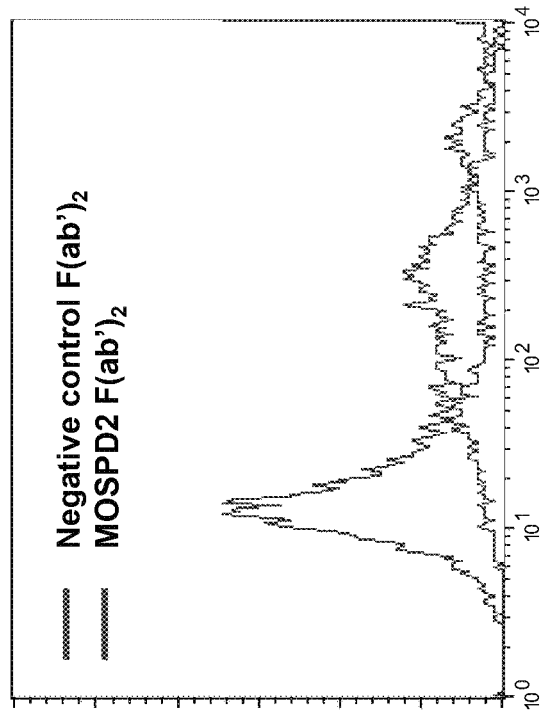
FIGS. 14A-14B show binding of two representative anti-MOSPD2 F(ab')2 mAb clones to cells overexpressing MOSPD2.
Figure 14B:
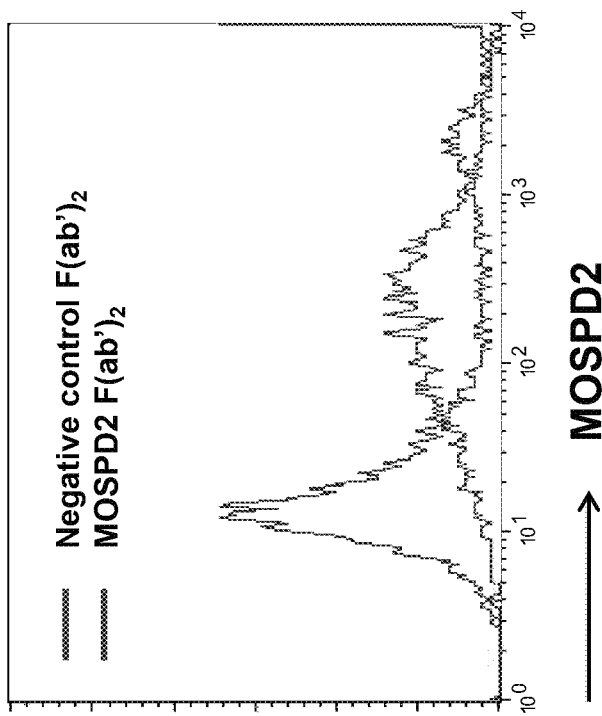

All clones positively stained the cells. Representative staining for 2 clones is shown in FIGS. 14A-14B. A clone that was not identified as a positive clone in Example 8 with ELISA was used as a negative control.

Example 10

Defining Cellular Expression Specificity and Localization of MOSPD2

Analysis of different immune cell subpopulations indicated that MOSPD2 is expressed predominantly in CD14+ monocytes over T and B lymphocytes (FIG. 15A). To determine MOSPD2 mRNA expression level, RNA was extracted from cells using RNeasy mini kit (Qiagen, ValenVBa, CA). For cDNA preparation, 2 µg of RNA was combined with qScript reaction mix and qScript reverse transcriptase (Quanta Bioscience, Gaithersburg, MD). The reaction was placed in a thermal cycler (BioRad, Hercules, CA) and a run was programmed according to manufacturer's instructions. Real-time PCR reactions were performed on an Applied Biosystems 7300 real time PCR system (Grand Island, NY) using sets of primers for human MOSPD2, 28S to normalize RNA levels (BIOSEARCH TECHNOLOGIES, Petaluma, CA) and SYBR Green PCR Master Mix (Applied Biosystems, Warrington, UK).

Figure 15B:
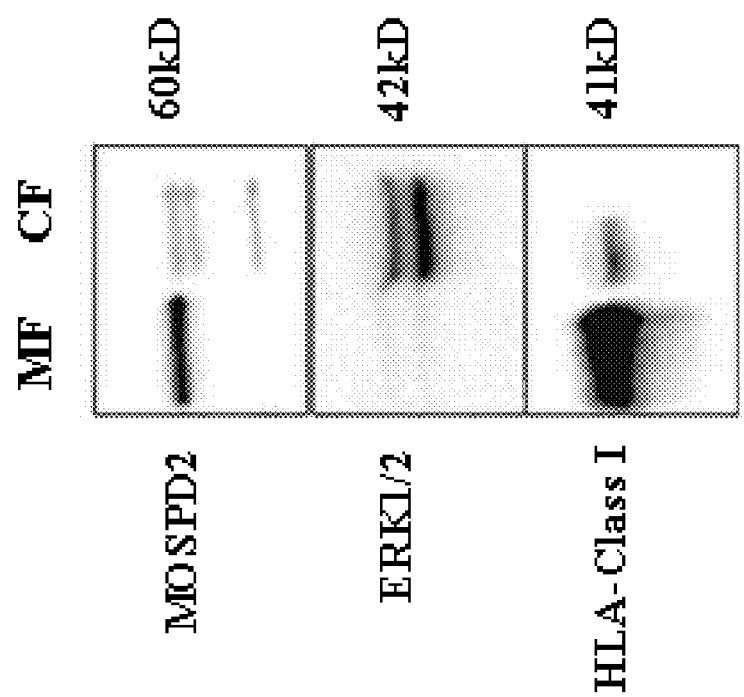
Figure 15C:
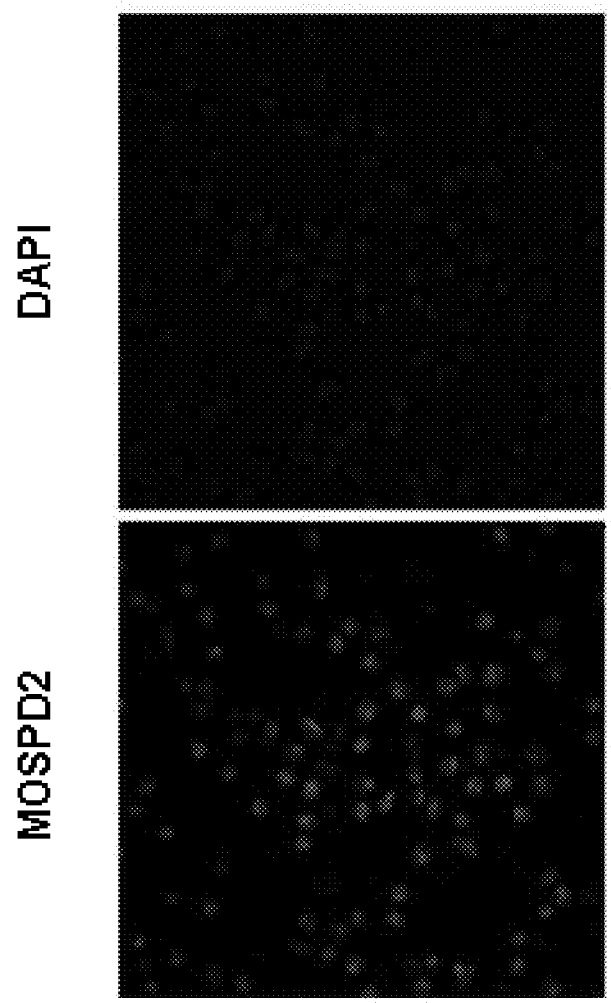
Figure 15D:
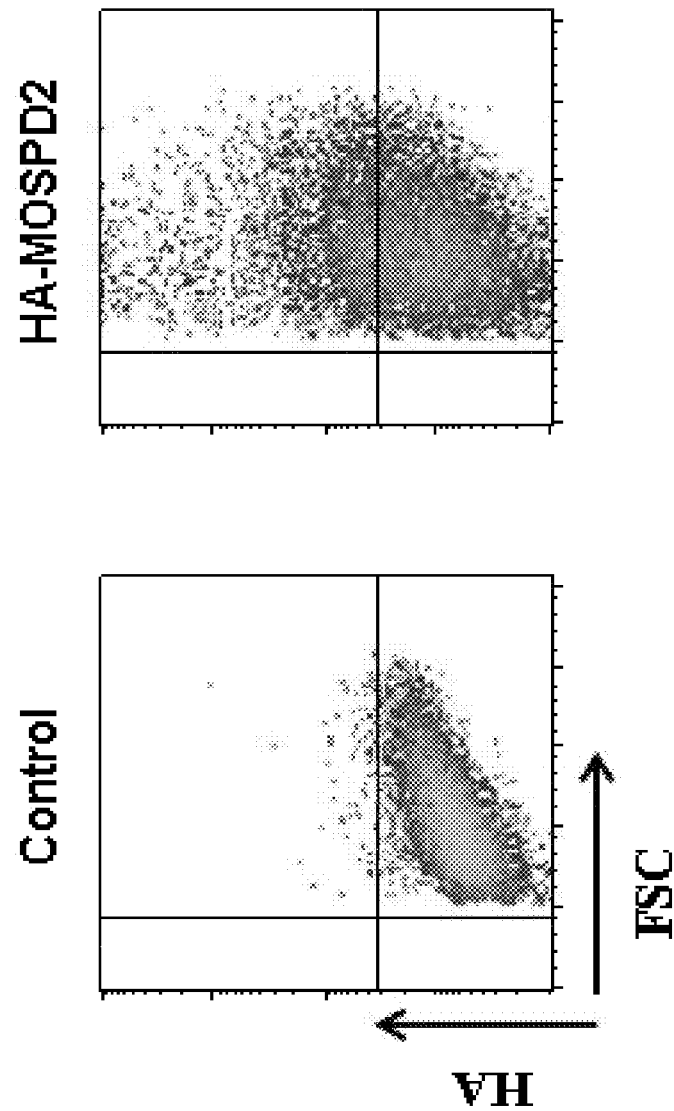

MOSPD2 is predicted to be a plasma membrane protein with one transmembrane region and one residue-long intracellular tail. Fractionation of cellular compartments, and immunofluorescence staining of human monocytes, and flow cytometry on HEK 293 cells transfected to overexpress HA-tagged MOSPD2 (performed according to the methods described above) revealed that MOSPD2 is a cell surface protein that is expressed on the plasma membrane of human monocytes (FIGS. 15B-15D, respectively).

Example 11

MOSPD2 is Expressed on Monocytes Infiltrated into Inflamed Tissues

Formalin-fixed tissues were dehydrated, embedded in paraffin, and sectioned at 4 µm. Immunostaining was fully calibrated on a Benchmark XT staining module (Ventana Medical Systems). After sections were dewaxed and rehydrated, anti-CD163 (Cell Marque, Rocklin, USA, MRQ-26) or anti-MOSPD2 diluted at 1:80 and 1:100, respectively, added rest for 40 minutes. Anti-CD163 staining was detected using UltraView universal Alkaline Phosphatase red detection kit (Ventana Medical Systems, 760-501) and anti-MOSPD2 staining was detected using UltraView universal DAB detection kit (Ventana Medical Systems, 760-500). When double staining was applied, MOSPD2 staining was performed first followed by CD163 staining. Slides were counterstained with hematoxylin (Ventana Medical Systems). After the run on the automated stainer was completed, slides were dehydrated consecutively in 70% ethanol, 95% ethanol and 100% ethanol for 10 sec each. Before cover slipping, sections were cleared in xylene for 10 sec and mounted with Entellan. MOSPD2 and CD163 stained slides were viewed using an Olympus BX51 microscope. Images were taken using a Nikon digital sight camera and NIS Elements Imaging Software.

As shown in FIGS. 16A-16C, MOSPD2 is expressed on monocytes infiltrated into a variety of inflamed tissues. FIG. 16A shows the staining of synovial membrane from a rheumatoid arthritis patient for CD163, MOSPD2, or both CD163 and MOSPD2. FIG. 16B shows the staining of atherosclerotic carotid tissue for CD163, MOSPD2, or both CD163 and MOSPD2. FIG. 16C shows the staining of infiltrating ductal carcinoma breast tissue for MOSPD2. Dark arrows indicate positive staining for tumor cells. Light arrows indicate staining of infiltrating monocytes.

Example 12

MOSPD2 does not Affect IFN-Gamma-Induced Activation or PKC-Mediated Activation

Figure 17A:
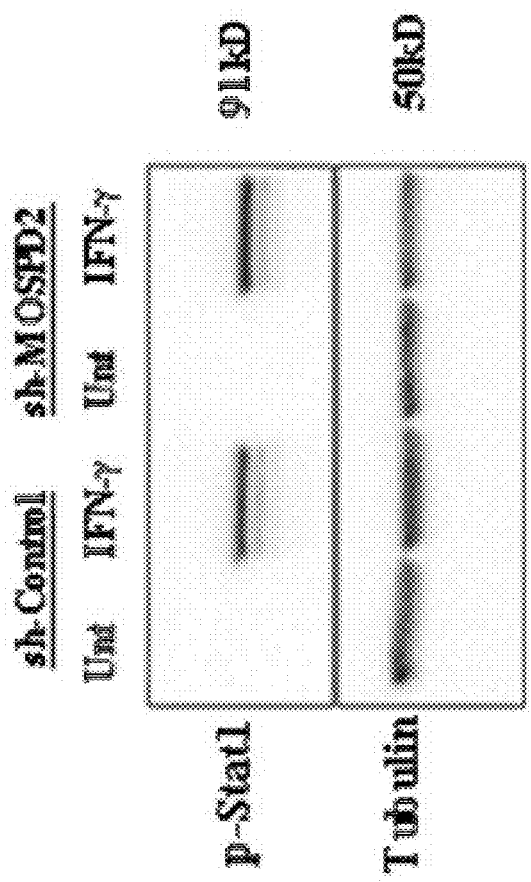
FIGS. 17A-17B show MOSPD2 does not affect IFN-gamma-induced STAT1 phosphorylation (p-Stat1) or PMA-mediated ERK1/2 phosphorylation (p-ERK1/2), respectively.
Figure 17B:
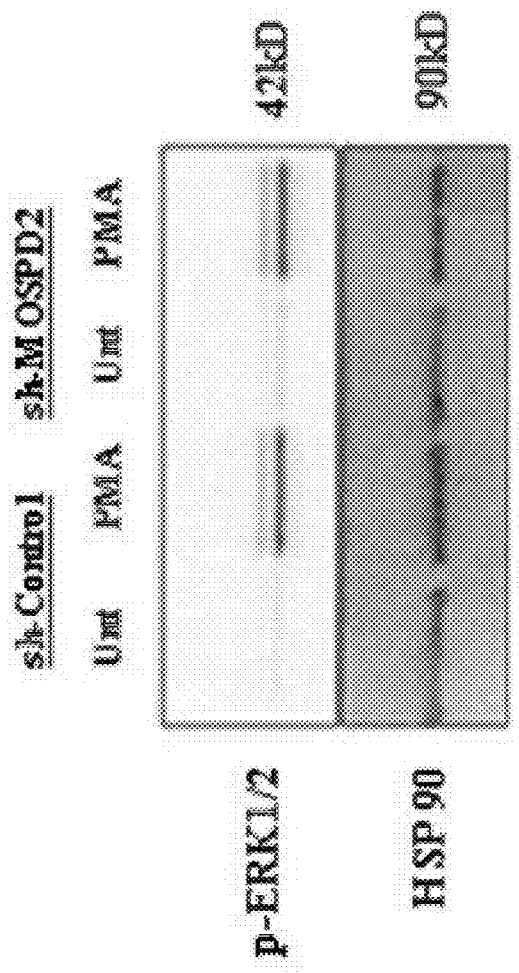

Targeting MOSPD2 did not compromise biological functions of monocytes other than migration. U937 monocytic line cells were transduced with sh-lenti control or sh-lenti MOSPD2 viral particles as described above and treated with IFN-gamma or with PMA. Western blot analysis of treated cells showed that silencing of MOSPD2 did not alter phosphorylation of downstream signaling markers by IFN-gamma or PMA (FIGS. 17A and 17B, respectively). These results suggest that MOSPD2 specifically promotes monocyte migration.

Example 13

Epitope Mapping of Anti-MOSPD2 Antibodies

To determine the epitope(s) that anti-MOSPD2 antibodies may specifically bind on human MOSPD2, binding affinities to various human MOSPD2 fragments are measured, as described herein, by capturing N-terminally biotinylated MOSPD2 fragments via a pre-immobilized streptavidin (SA) on a SA chip and measuring binding kinetics of anti-MOSPD2 antibodies titrated across the MOSPD2 surface (the BIAcore®3000™ surface plasmon resonance (SPR) system, Biacore, Inc., Piscataway NJ). BIAcore assays are conducted in HBS-EP running buffer (10 mM HEPES pH 7.4, 150 mM NaCl, 3 mM EDTA, 0.005% v/v polysorbate P20). MOSPD2 surfaces are prepared by diluting the N-biotinylated MOSPD2 to a concentration of less than 0.001 mg/mL into HBS-EP buffer and injecting it across the SA sensor chip using variable contact times. Low capacity surfaces, corresponding to capture levels<50 response units (RU) are used for high-resolution kinetic studies, whereas high capacity surfaces (about 800 RU of captured MOSPD2) are used for concentration studies, screening, and solution affinity determinations.

Kinetic data is obtained by diluting antibody G1 Fab serially in two- or three-fold increments to concentrations spanning 1 μM-0.1 nM (aimed at 0.1-10 times estimated Kd). Samples are typically injected for 1 minute at 100 μL/min and dissociation times of at least 10 minutes are allowed. After each binding cycle, surfaces are regenerated with 25 mM NaOH in 25% v/v ethanol, which is tolerated over hundreds of cycles. An entire titration series (typically generated in duplicate) is fit globally to a 1:1 Langmuir binding model using the BIAevaluation program. This returns a unique pair of association and dissociation kinetic rate constants (respectively, $K_{on}$ and $K_{off}$) for each binding interaction, whose ratio gives the equilibrium dissociation constant ($K_D = K_{off}/K_{on}$).

Anti-MOSPD2 antibodies may specifically bind to one or more of the following amino acid regions of human MOSPD2, numbered according to SEQ ID NO:1 (amino acid residues 1-518): 508-517, 501-514, 233-241, 509-517, 212-221, 13-24, 505-517, 505-514, 89-100, 506-517, 233-245, 504-514, 128-136, 218-226, 15-24, 83-96, 42-50, 462-474, 340-351, 504-517, 462-470, 327-337, 21-32, 217-226, 510-517, 178-190, 497-509, 504-516, 64-77, 504-515, 147-159, 503-315, 88-97, 208-218, 178-191, 502-515, 503-516, 497-505, 500-509, 189-202, 189-197, 505-516, 1-63, 82-239, 93-234, 327-445, 327-431, and 497-517.

Example 14

Additional Anti-MOSPD2 Antibodies

Additional anti-MOSPD2 antibodies are generated that recognize one or more MOSPD2 epitopes, following the methodology described in Example 5 (polyclonal antibodies) or Example 8 (monoclonal antibodies).

Briefly, portions of MOSPD2 identified in Example 14 as MOSPD2 epitopes are fused to human Fc and immobilized on a solid support. A HuCAL® library (HuCAL PLATINUM® Platform; Bio-Rad AbD Serotec, GmnH) presented on phage particles is incubated with the immobilized antigen. Nonspecific antibodies are removed by extensive washing and specific antibody phages are eluted by adding a reducing agent. Antibody DNA is isolated as a pool and subcloned into an E. coli expression vector to generate bivalent F(ab')$_2$ mAb. Colonies are picked and grown in a microtiter plate. The cultures are lysed to release the antibody molecules and screened for specific antigen binding by ELISA and FACS. Unique antibodies are expressed and purified using one-step affinity chromatography, and then tested again by ELISA and FACS for specificity.

All publications, patents and patent applications mentioned in this application are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A method of treating a chronic inflammatory disease or disorder in a subject, comprising administering to the subject an inhibitor of MOSPD2, wherein the inhibitor is an RNA silencing agent, and wherein the chronic inflammatory disease or disorder is rheumatoid arthritis, systemic lupus erythematosus, scleroderma, mixed connective tissue disease, polyarteritis nodosa, polymyositis/dermatomyositis, Sjogren's syndrome, Behcet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides, or heparin induced thrombocytopenia.

2. The method of claim 1, wherein the inhibitor is miRNA, siRNA, or shRNA.

3. The method of claim 2, wherein the inhibitor is shRNA.

4. The method of claim 1, wherein the subject is a human.

5. The method of claim 2, wherein the inhibitor is miRNA.

6. The method of claim 2, wherein the inhibitor is siRNA.

7. The method of claim 1, wherein the chronic inflammatory disease or disorder is rheumatoid arthritis.

8. The method of claim 1, wherein the chronic inflammatory disease or disorder is systemic lupus erythematosus.

9. The method of claim 1, wherein the chronic inflammatory disease or disorder is scleroderma.

10. The method of claim 1, wherein the chronic inflammatory disease or disorder is polyarteritis nodosa.

11. The method of claim 1, wherein the chronic inflammatory disease or disorder is multiple sclerosis.

12. The method of claim 1, wherein the chronic inflammatory disease or disorder is autoimmune diabetes.

13. The method of claim 1, wherein the chronic inflammatory disease or disorder is Hashimoto's disease.

14. The method of claim 1, wherein the chronic inflammatory disease or disorder is psoriasis.

15. The method of claim 1, wherein the chronic inflammatory disease or disorder is Behcet's disease.

16. The method of claim 1, wherein the chronic inflammatory disease or disorder is myasthenia gravis.

17. The method of claim 1, wherein the chronic inflammatory disease or disorder is chronic active hepatitis.

18. The method of claim 1, wherein the chronic inflammatory disease or disorder is vasculitides.

19. The method of claim 1, wherein the chronic inflammatory disease or disorder is idiopathic thrombocytopenia purpura.

20. The method of claim 1, wherein the chronic inflammatory disease or disorder is uveitis.

* * * * *